US012766710B2

(12) United States Patent
Bydlon et al.

(10) Patent No.: US 12,766,710 B2
(45) Date of Patent: Oct. 20, 2026

(54) SYSTEM AND DEVICE CONTROL USING SHAPE CLUSTERING

(71) Applicant: KONINKLIJKE PHILIPS N.V., Eindhoven (NL)

(72) Inventors: Torre Michelle Bydlon, Melrose, MA (US); Molly Lara Flexman, Melrose, MA (US); Ayushi Sinha, Baltimore, MD (US); Aleksandra Popovic, Boston, MA (US); Grzegorz Andrzej Toporek, Cambridge, MA (US); Alyssa Torjesen, Exeter, NH (US); Marcin Arkadiusz Balicki, Cambridge, MA (US); Vipul Shrihari Pai Raikar, Somerville, MA (US); Ahmet Ekin, Eindhoven (NL); Maha Shady, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 9 days.

(21) Appl. No.: 18/576,438

(22) PCT Filed: Jul. 4, 2022

(86) PCT No.: PCT/EP2022/068361
§ 371 (c)(1),
(2) Date: Jan. 4, 2024

(87) PCT Pub. No.: WO2023/280732
PCT Pub. Date: Jan. 12, 2023

(65) Prior Publication Data

US 2024/0383133 A1 Nov. 21, 2024

Related U.S. Application Data

(60) Provisional application No. 63/219,507, filed on Jul. 8, 2021.

(30) Foreign Application Priority Data

Sep. 28, 2021 (EP) .................................... 21199460

(51) Int. Cl.
*B25J 9/16* (2006.01)
*A61B 34/00* (2016.01)
(Continued)

(52) U.S. Cl.
CPC ............... *B25J 9/163* (2013.01); *A61B 34/20* (2016.02); *A61B 34/25* (2016.02); *A61B 34/30* (2016.02);
(Continued)

(58) Field of Classification Search
CPC .......... B25J 9/163; A61B 34/20; A61B 34/25; A61B 34/30; A61B 90/37;
(Continued)

(56) References Cited

U.S. PATENT DOCUMENTS

| | | | | |
|---|---|---|---|---|
| 6,618,612 B1 * | 9/2003 | Acker | A61B 90/36 128/899 |
| 2011/0319714 A1 * | 12/2011 | Roelle | A61B 1/0051 600/118 |

(Continued)

FOREIGN PATENT DOCUMENTS

| | | |
|---|---|---|
| CN | 112641515 A | 4/2021 |
| WO | 2013182953 A1 | 12/2013 |

(Continued)

OTHER PUBLICATIONS

Dipietro et al., "Unsupervised learning for surgical motion by learning to predict the future", Medical Image Computing and Computer Assisted Intervention—MICCAI 2018. 11073, pp. 281-288.

(Continued)

*Primary Examiner* — Sohana Tanju Khayer

(57) ABSTRACT

Computer implemented system (C-SYS) and related methods for controlling one or more devices in a procedure
(Continued)

performed in relation to a patient. A shape sensing system is used to acquire shape measurement data. A predictor logic (PL) predicts based on this shape measurements an anatomical location, procedure type, or phase of such a procedure. The System may support navigation of a device in the patient. No imagery need to be acquired during the procedure for navigation. The predictor logic (PL) may be based on a machine learning model. Systems (TS, TDS) and methods for training such as model and for generating training data are also described herein.

14 Claims, 21 Drawing Sheets

(51) Int. Cl.

| | |
|---|---|
| ***A61B 34/20*** | (2016.01) |
| ***A61B 34/30*** | (2016.01) |
| ***A61B 90/00*** | (2016.01) |
| ***G06N 3/045*** | (2023.01) |
| ***G06N 3/0455*** | (2023.01) |
| ***G06N 3/0464*** | (2023.01) |
| ***G06N 3/047*** | (2023.01) |
| ***G06N 3/088*** | (2023.01) |
| ***G06N 3/09*** | (2023.01) |
| ***G06N 20/00*** | (2019.01) |
| *G06N 3/0895* | (2023.01) |

(52) U.S. Cl.

CPC ............. *A61B 90/37* (2016.02); *G06N 3/045* (2023.01); *G06N 3/0455* (2023.01); *G06N 3/0464* (2023.01); *G06N 3/088* (2013.01); *G06N 20/00* (2019.01); *A61B 2034/2061* (2016.02); *A61B 2034/2065* (2016.02); *A61B 2562/0266* (2013.01); *G06N 3/047* (2023.01); *G06N 3/0895* (2023.01); *G06N 3/09* (2023.01)

(58) Field of Classification Search

CPC .... A61B 2034/2061; A61B 2034/2065; A61B 2562/0266; A61B 2034/301; A61B 2090/374; A61B 2090/376; A61B 2090/3762; A61B 2090/378; A61B 5/6847; A61B 5/7267; A61B 5/066; A61B 5/065; G06N 3/045; G06N 3/0455; G06N 3/0464; G06N 20/00; G06N 3/047; G06N 3/088; G06N 3/0895; G06N 3/09

See application file for complete search history.

(56) References Cited

U.S. PATENT DOCUMENTS

| | | | | |
|---|---|---|---|---|
| 2014/0088413 | A1* | 3/2014 | Von Bucsh | A61B 5/0084 600/424 |
| 2015/0109196 | A1* | 4/2015 | Grass | G06F 3/017 345/156 |
| 2015/0148690 | A1 | 5/2015 | Chopra et al. | |
| 2016/0101263 | A1* | 4/2016 | Blumenkranz | A61B 5/1076 600/117 |
| 2016/0302869 | A1* | 10/2016 | Chopra | A61B 5/066 |
| 2016/0324585 | A1* | 11/2016 | Noonan | A61B 90/37 |
| 2016/0349044 | A1* | 12/2016 | Marell | G01B 21/045 |
| 2017/0151027 | A1* | 6/2017 | Walker | A61B 34/37 |
| 2017/0157361 | A1* | 6/2017 | Barrish | A61B 17/00234 |
| 2017/0215973 | A1* | 8/2017 | Flexman | G01D 5/35358 |
| 2017/0273746 | A1* | 9/2017 | Flexman | A61B 5/1128 |
| 2018/0008352 | A1 | 1/2018 | Flexman et al. | |
| 2018/0137687 | A1* | 5/2018 | Katz | A61B 18/1492 |
| 2018/0228554 | A1* | 8/2018 | Strommer | A61B 5/7289 |
| 2018/0263716 | A1* | 9/2018 | Flexman | A61B 90/37 |
| 2018/0344204 | A1 | 12/2018 | Flexman et al. | |
| 2019/0307511 | A1* | 10/2019 | Ludwin | A61B 5/068 |
| 2020/0030575 | A1* | 1/2020 | Bogusky | A61M 16/0488 |
| 2020/0046431 | A1 | 2/2020 | Soper et al. | |
| 2020/0138334 | A1* | 5/2020 | Hill | A61B 5/6852 |
| 2020/0138525 | A1* | 5/2020 | Hill | A61B 5/6858 |
| 2021/0045814 | A1 | 2/2021 | Thompson et al. | |
| 2021/0401407 | A1* | 12/2021 | Yang | A61B 8/0841 |
| 2021/0401508 | A1* | 12/2021 | Zhao | G06T 3/153 |
| 2022/0096198 | A1* | 3/2022 | Lynch | A61B 1/0655 |
| 2022/0142713 | A1* | 5/2022 | Oren | A61B 5/287 |
| 2022/0354597 | A1* | 11/2022 | Kaouk | A61B 34/30 |
| 2023/0034112 | A1* | 2/2023 | Wang | G06T 19/003 |
| 2023/0091099 | A1* | 3/2023 | Wang | A61B 34/20 600/424 |
| 2023/0346479 | A1* | 11/2023 | Muller | A61B 34/20 |
| 2023/0414293 | A1* | 12/2023 | Farley | A61B 34/20 |
| 2024/0050162 | A1* | 2/2024 | Hendriks | A61B 5/062 |
| 2024/0060770 | A1* | 2/2024 | Ha | G01L 1/246 |
| 2024/0081921 | A1* | 3/2024 | Ben-Yishai | G06T 7/0012 |

FOREIGN PATENT DOCUMENTS

| | | | |
|---|---|---|---|
| WO | 2017030915 | A1 | 2/2017 |
| WO | 2018144636 | A1 | 8/2018 |
| WO | 2020173814 | A1 | 9/2020 |
| WO | 2022048984 | A1 | 3/2022 |

OTHER PUBLICATIONS

International Search report and Written Opinion of PCT/EP2022/068361, dated Sep. 22, 2022.

* cited by examiner

A)

B)

C)

SYSTEM AND DEVICE CONTROL USING SHAPE CLUSTERING

CROSS-REFERENCE TO PRIOR APPLICATIONS

This application is the U.S. National Phase application under 35 U.S.C. § 371 of International Application No. PCT/EP2022/068361, filed on Jul. 4, 2022, which claims the benefit of U.S. Provisional Application Ser. No. 63/219,507, filed on Jul. 8, 2021 and European Patent Application No. 21199460.3, filed on Sep. 28, 2021. These applications are hereby incorporated by reference herein.

FIELD OF THE INVENTION

The invention relates to a system for controlling operation of at least one device in a medical procedure, to a related method, to a method and system of training a machine learning module, to a method and system of generating training data, to a computer program element, and to computer readable medium.

BACKGROUND OF THE INVENTION

Minimally invasive surgery (also called "key-hole surgery") is advantageous for patients and health care providers alike. Instead of open surgery, interventional devices, such as catheters and surgical instruments are introduced into the patient at an entry points (often one or more tiny incisions). In a navigation phase, the interventional device is advanced inside the patient from the entry point to a lesion inside the patient for treatment and/or diagnosis. With minimally invasive surgery, as compared to traditional, invasive, open surgery, patients recover quicker, can be discharged earlier, and patient comfort in general is vastly increased.

The intervention, and especially the navigation phase, is generally done in an image-guided manner. Imagery of the patient's internal anatomy is acquired by an imaging apparatus during the intervention. The imagery may be acquired as a live stream. Ionizing radiation is often used by the imaging apparatus. Such imagery is useful but comes at a radiation dose cost for patient and interventionalist. Ionizing radiation is a health hazard and can cause a range of health problem, including cancer.

Shape sensing was described in US 2009/0137952 A1. Earlier, radio-opacity of certain interventional devices was harnessed as this allowed for detailed representation of such a device's current shape in projection imagery. During manipulation of the device, it's shape or state would often change, and this could be monitored by acquiring a stream of X-ray images. But as said, again, this comes at a radiation dosage cost. With the shape sensing device as described in US 2009/0137952 A1 as integrated into the interventional device, the current shape of the interventional device could be inferred from shape measurements by the shape sensing device without acquiring imagery.

SUMMARY OF THE INVENTION

There may be a need for additional support of procedures that include interventions.

An object of the present invention is achieved by the subject matter of the independent claims where further embodiments are incorporated in the dependent claims. It should be noted that the following described aspect of the invention equally applies to the related method, to the method and system of training a machine learning module, to the method and system of generating training data, to the computer program element and to the computer readable medium.

The systems and methods according to the invention are as per the appended claims.

The proposed systems and methods may be applied in a range of procedures such as interventions, including vascular (guidewire, catheters, stent sheaths, deployment systems, etc.), endoluminal (endoscopes or bronchoscopes), orthopedic (k-wires & screwdrivers) as well as non-medical applications. The proposed control system and method may assist in navigation and/or controlling a host of different devices to promote efficiency in procedures.

Shape sensing as used herein could be of any type or technology, preferably without use of ionizing radiation. For example, shape sensing could be based on Rayleigh scattering (enhanced and regular) or Fiber Bragg implementations of one or more shape sensing fibers. Specially, the shape sensing system may be based on continuously distributed shape sensing elements, or discrete sensing elements arranged along a deformable, preferably flexible, elongated portion or body, referred to herein as a "(shape sensing) arm". At least a part of the arm is inside the patient's body. Sensing discrete data points collected there may be interpolated by the system to result in instances of shape measurement data, or alternatively the sensing is continuously distributed along the interventional device. Preferably this shape sensing system is an optical shape sensing system comprising shape sensing elements provided on one or more optical fibers over at least a portion of the fiber's/arm's length. Such optical shape sensing elements may include Fiber Bragg gratings, whose optical properties change with strain or shape or temperature. They can be provided in optical fibers or in multicores of an optical fiber forming the said arm. The fibers or core(s) are arranged to retrieve shape of the interventional device (e.g. guidewire or catheter, or other such, generally elongated, device) in which the fiber(s) are integrated, attached to, or otherwise spatially associated to run alongside the arm. This arrangement may for instance include a central fiber or core and other fibers or cores may be angularly arranged and wound around the central fiber or core, as it is known in the art. Alternatively or in addition to such optical shape sensing, changes in resistance of piezoresistive flexible shape flexible sensors or changes in an electromagnetic field provided from electromagnetic sensors, may also be used to measure shape changes.

The shape measurement data may be generated in response to deformation of the said part of the arm, whilst the arm is moved inside the patient's body by a user or robot. The arm may be integrated or coupled to an interventional device. A part of the interventional device may deform with the arm. However, such an arm is not a necessary requirement herein and any other shape sensing technologies are also envisaged herein. The shape measurement data may include measurements of any one or more of curvature, stress, and strain along different positions of the arm for example. Measurement of other quantities representative of, or convertible into, shape of the arm/interventional device are also envisaged herein.

In a particular embodiment, the shape sensing interventional device (e.g. a guidewire run alongside the shape sensing arm) may be coaxially used within or around a non-shape sensing other interventional device or tool (e.g. a catheter, a sheath, other surgical tool). The shape of the non-shape sensing other interventional device may be reconstructed by a computing device, thanks to a registration of the two interventional devices together. Such a registration may be performed for instance via a hub receiving both devices or via any other coupling device capable to impart shape information. The use of shape data as proposed herein thus extends to even non-shape sensing interventional device(s), in case the latter is registered to the shape sensing interventional device.

The logic of the invention may be based on a trained model, such as machine learning model. The training is based on training data. The training may be a one-off operation, or, preferably is repeated in a dynamic learning approach where measurements encountered during deployment and are added to enlarge or build a training data set. Uncertainty values associated with the output or prediction may be used to decide which new measurements to add to the training data set. Interactive user interface options for deciding which measurements to so add are also envisaged herein.

The training data may or may not include image data. Preferably it does not. The logic is capable to compute a result based on the input shape measurement as sensed by the shape sensing system, and previous shape measurements and, optionally, contextual data. The shape measurements and the contextual data may together form "enriched data". Using such enriched data allows for more robust outputs or predictions. For example, variance of the training data set may be increased. The enriched data may provide better context to so support the training algorithm. The contextual data may be included as annotations or tags by annotator module ("annotator"). The annotator may be user operated through a suitable user interface, such as graphical user interface. Alternatively, the annotator is semi-automatic (so there may be some user input) or automatic (no user input).

The previous shape measurement data, on which operation of the logic is based (in addition to the current shape measurement data), may relate to one or more patients other than "the" current patient. The previous measurements may thus be drawn from eg, historical data from previous procedures collected from different one or more patients. The said previous data forms the training data on which the model of the logic was trained. The previous measurement data as training data, is not necessarily historical, but may instead be artificially generated as synthetic training data, by user or automatically by computer, image-based or not. The previous data may be exclusively historical, exclusively synthetic or is a mix of synthetic and historical.

In deployment, the "previous shape measurement data" may instead or in addition relate to earlier shape measurement data collected in the same procedure for same patient. So rather than basing the output or prediction by the logic on only the current shape measurement (which is also envisaged herein), the logic may co-process, with the current shape measurement, the previous (in time) n shape measurements, $n \geq 1$, preferably in the chronological order in which they were earlier acquired b the shape sensing system. The block or buffer-length n may be changed, to account for the initial part of the procedure. Buffer length n may be chosen smaller initially, and then enlarged further down the line in the procedure.

The predicted or output result includes an anatomical location, procedure type or phase of said procedure. The procedure is preferably medical, such as an intervention in relation to an organ or anatomy, lesion, target site, etc. The predicted or output anatomical location is an estimate of where in the patient body the arm or interventional device currently resides, or in which procedure type or phase thereof the arm/international device is currently used.

During deployment, the logic is cable of computing the output or prediction without use of image data. No acquired imagery (live or not) of the patient is required for operation of the logic in deployment. The logic may operate solely on shape measurement data, in particular at the exclusion of image data. X-ray dosage can thus be reduced or avoided altogether. The predicted or output result allows for example navigation without reliance on acquired imagery. The user is informed by the predicted or output result where the device/arm is and in which procedure or which phase of the procedure.

An indication, graphical or otherwise, of the output or predicted result and/or of the current shape measurement may be displayed on display device to assist the user in navigation. But controlling such display device is merely one example of how the predicted or output result may be used to control a device. Other control operations of one or more other devices are envisaged, in addition or instead of controlling the display device as described and claimed herein.

The control system with the logic may be coupled to a training system to retrain in dynamic learning the model based on the shape measurements encountered during deployment. A current training data set may be so enlarged with new data, and one or more training sessions may be re-run by the training system as requested by the user or triggered automatically, based on contextual data or prediction or output uncertainty.

The model may be one of clustering, trained and built on training data including historic and/or synthetically generated shape measurements. The categories predicted or output are hence presented by clusters in the training data. Training may be done independent from imagery such as X-ray imagery, but alternatively such imagery may still be used, in particular when generating synthetic trainings data by the training data generator system, as claimed and described herein.

Each category, such as a cluster, of shape measurements can be associated with anatomical features, or with a respective anatomical portion/location or a procedure type or phase which can be then retrieved without any additional information than the shape data, although, optionally, contextual data may still be used if desired. If a clustering approach is used, the current measurement may be displayed concurrently with a graphical rendition of some or all clusters. The models envisaged herein for the logic are however not confined to cluster type models. Other (machine learning) models, such as artificial neural networks, encoder-autoencoder, and other still, are also envisaged herein in embodiments. In other words, the predicted or output category is not necessarily indicative of a cluster in the training data, but may relate instead to classifier results, etc. Graphical indications of the said classes may also be displayed.

In order to boost performance, training and/or deployment may not necessarily be based on raw shape measurements (although this can still be done), but the raw measurements are transformed first into new representations. The training/deployment may then based on the shape measurements so transformed. A "representation" as used herein relates to systems, parameters, quantities that are used to describe or express the shape measurements. A change of representation may involve changing number and/or nature of such systems, parameters, and quantities. A change of representations may include coordinate transformations, change of basis elements, dimensional reduction, sparsity changes relative to a set of basis elements, etc. The transformation may map elements of one parameter space (such as a vector space) into elements of another space, or a sub-space, etc. Such a transformation may help reduce return time of the logic, may make training and/or deployment more robust, and/or may reduce memory requirements.

The interventions supported herein include manual and/or robotic manipulation of interventional devices.

As said, although not required herein, the proposed systems and methods can still be used in combination with any imaging system, including x-ray, ultrasound, MRI, CT, OCT, IVUS, endoscopy, etc. As an option, the predicted or output category may be used to decide whether or not to register the international device/arm P with a given image.

"User" relates to a person, such as medical personnel or other, operating the imaging apparatus or overseeing the imaging procedure. In other words, the user is in general not the patient.

In general, the term "machine learning" includes a computerized arrangement (or module) that implements a machine learning ("ML") algorithm. Some such ML algorithms may use explicit modeling. They operate to adjust a machine learning model. The model may comprise one or more functions with parameter(s). Parameters are adjusted based on training data. The adjusting of the parameters may be guided by an objective function defined on parameter space. The model is configured to perform ("learn") a task. Some ML models, such as in implicit modelling, include the training data. This adjusting or updating of training data corpus is called "training". Use of a trained model to process data to perform the task is referred to herein as deployment or inference. Training may be a one-off operation or may be done repeatedly after different deployments. In general task performance by the ML module may improve measurably, with training experience. Training experience may include exposure to suitable training data. Training may be supervised or unsupervised. Task performance may improve when the data better represents the task to be learned. "Training experience helps improve performance if the training data well represents a distribution of examples over which the final system performance is measured". The performance may be measured by objective tests based on output produced by the module in response to feeding the module with test data. The performance may be defined in terms of a certain error rate to be achieved for the given test data. See for example, T. M Mitchell, "Machine Learning", page 2, section 1.1, page 6 1.2.1, McGraw-Hill, 1997.

The terms "labelling"|"annotating"|"tagging" are used largely interchangeably herein and relate to associating additional/contextual data with shape measurements, in training or during deployment. The term labelling is mainly (but not exclusively) used herein in relation to training data, in particular relation to supervised learning arrangements. where the label relates to the respective target.

The term "anatomical location" is not necessarily a point location but may include a region or may pertain to an anatomical feature.

The term "category" is the predicted or output result as predicted/computed by the logic. This category may relate to cluster or class label more generally. The category is associable with the anatomical location, procedure type, or phase of procedure. Whilst in the examples/embodiments described herein main reference is made to the category being indicative to an anatomical location, this is not limiting herein. Specifically, each reference in this disclosure to "anatomical location" may be construed instead or in addition as a reference to the said "procedure type" or "phase of procedure".

"interventional device", any, preferably. medical device, tool, instrument or implement having a generally elongated shape or such portion for at least partial introduction into a patient. Preferably, such interventional device is used together with the shape sensing arm of the shape sensing system.

"Contextual data" as used herein refers to data contextual to the shape measurements. This includes data that affect the shape measurements (and hence the predicted or output category) and/or describe the manner in which the shape measurements are collected. Contextual data may be used herein to improve performance of the logic.

"predict" as used herein refers to computation or computing by a logic (e.g. computing means or computer program) of input data in order to output results based on a model.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
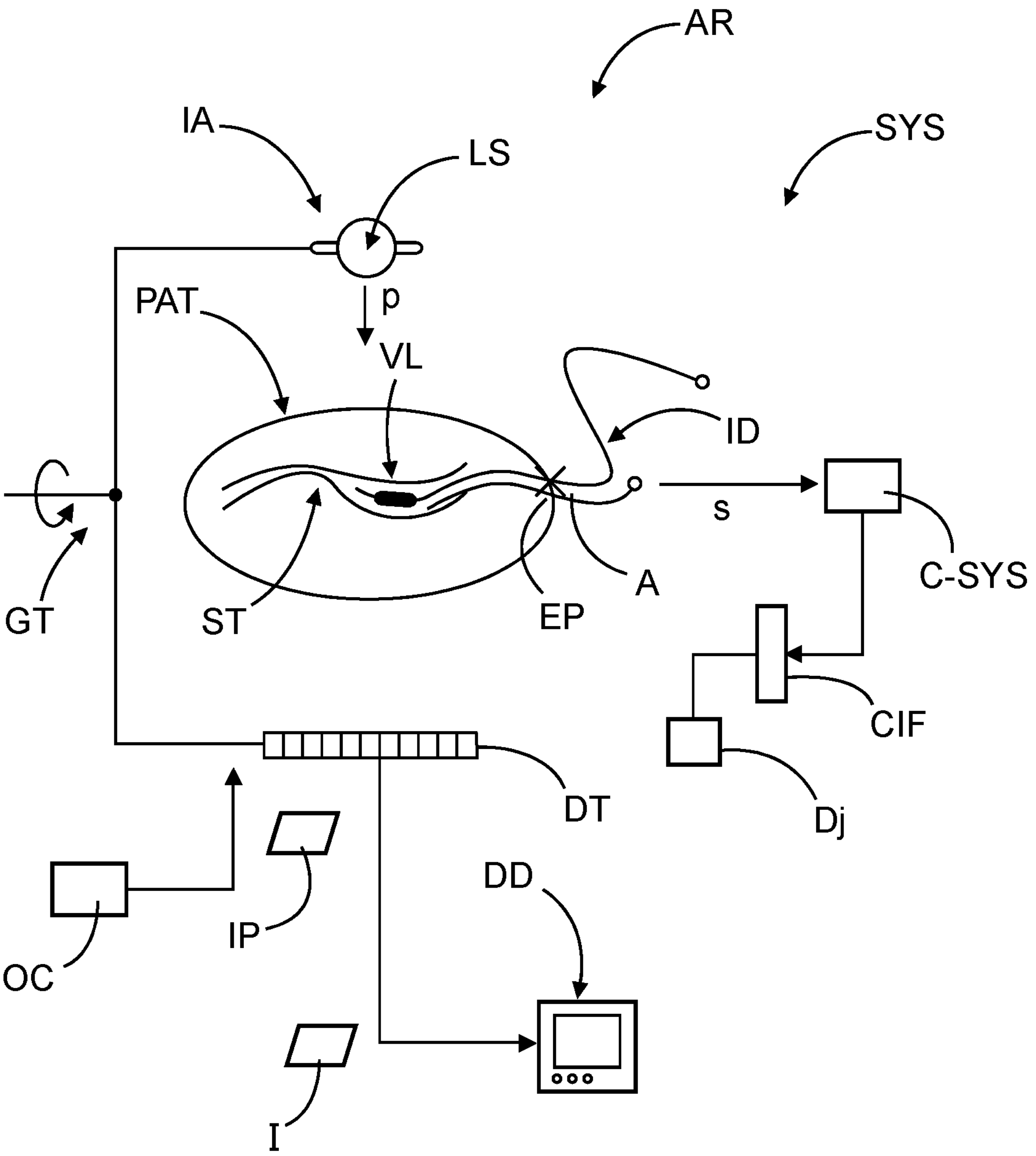
FIG. 1 shows a block diagram of an arrangement supporting an intervention.

With reference to FIG. 1, this shows a block diagram of an arrangement that may be used to support a medical intervention or other medical procedure. The arrangement includes an imaging apparatus IA (sometimes referred to herein as "the imager") and a computer-implemented system SYS to process certain data that is generated during the intervention.

The supported intervention may be one of treating a stenosis in a human or animal patient using a medical tool or implement such as a balloon catheter CB. Other catheter types, or other medical interventions or procedures in which different tools are used are also envisaged herein, such a mitral valve repair procedures, etc.

The imaging apparatus is preferably an X-ray imaging apparatus that produces a single x-ray exposure, such as in radiography, or, as in fluoroscopy or angiography applications, a sequence of X-ray exposures at a suitable frame rate as a real-time moving picture. Still imagery is also envisaged. Contrast agent may be administered through an injector to boost contrast of the imagery. The imagery produced by the imager IA may be displayed on a display device DD to assist a medical user, such as an interventional cardiologist, in performing the intervention.

Online support by the computer system SYS during the intervention is envisaged herein in the main, but the computer system SYS may also be used instead for pre-intervention or post-intervention investigation. For example, the system SYS may be used to prepare or plan an intervention or may be used to analyze data generated during previous one or more interventions to plan or inform follow-up treatments, interventions or other measures. Thus, the computer system may be a standalone system, not necessarily coupled to any imaging apparatus, and the processed data may not necessarily be live data but may instead be historic data, retrieved from a database or other storage.

Broadly, the system SYS may include a (sub-)-system C-SYS for controlling certain devices/systems Dj that are used during a medical procedure. In some medical procedures, such as interventions, certain tool(s) or device(s), referred to herein as "interventional device ID" may be used. The one or more interventional device ID is introduced at least partly into the patient to perform therapy or diagnosis. The introduced part of the device ID is occluded so in general there is no or very limited line of sight. The introduced part of the device needs to be navigated to a target within the patient in a navigation phase of the intervention. The control C-SYS system may provide information to support the user during navigation or during other phases of the medical procedure. The control system C-SYS (sometime referred to herein as the "controller") may use machine learning.

Before explaining the control system C-SYS in more detail, some exemplary medical procedures and the imaging apparatus IA will be described in more detail first to better illustrate operation of the proposed control system C-SYS.

Turning now first to the imaging apparatus IA, this is preferably of the X-ray type and is configured to acquire X-ray projection image(s). The image may be a single still image, such may be acquired in radiography, or may be part of a stream of images ("frames") that is used to display a video feed such as in fluoroscopy. The still image or stream may be displayed on a display device DD.

The imaging apparatus IA includes an X-ray source XS and an X-ray sensitive detector D. The imaging apparatus IA preferably allows acquiring imagery from different projection directions d. The imaging apparatus may include an optional gantry GT to which the X-ray source XS and/or the detector D are connected. The projection imagery may be acquired along different projection directions by rotation of the gantry (and with it, of the source XS and detector D) around the lesioned site ST or ROI. Such gantry-based imaging apparatuses include C- or O-arm systems and are mainly envisaged herein, but so are (CT) computed tomography scanners. Non-gantry based imaging solutions are also envisaged, such as mobile or portable imaging devices, where there is no, or no permanent, physical connection between detector D and radiation source XS. The imagery I to be processed by the system SYS may be projection imagery in projection domain as recorded by the detector D, or may comprise reconstructed imagery in image domain obtained by a computed tomography algorithm.

In more detail, during imaging, the X-ray source XS emits an X-ray beam which propagates along projection direction d to interact with patient tissue and/or the balloon catheter or other medical device BC, to cause a modified X-ray beam to emerge at the far end of the patient, and be detected at detector D. Data acquisition circuitry (not shown) of the detector D converts the received modified radiation into a set of numbers ("pixel values"), preferably stored in a respective matrix per frame/image, with respective rows and columns. The rows and columns define a size of the image/frame. The pixel values represent detected intensities. The pixel values per frame/image can be used by a visualization component VC to effect display of the image on the display device DD during the intervention. In the following we will no longer distinguish between frame and still image, and simply use the term "image/imagery" as a generic reference to both.

Operation of the imaging apparatus, in particular image acquisition, is controlled by the user from an operator console or control unit OC. Operator console may be arranged as a dedicated computing unit communicatively coupled to the imaging apparatus. The operator console may be situated in the same room as the imager IA or in an adjacent "control room". Remotely controlled imaging systems IA connected through a suitable communication network to a control unit OC, located possibly remotely from the imaging apparatus, is envisaged herein in embodiments. Autonomous imaging system are also envisaged herein, where the control unit OC operates fully or semi-autonomously, without or with little user input.

The imaging control unit OC controls the imaging operation by setting certain imaging parameters IP. The imaging parameters determine or at least influence the contrast mechanism and hence the image quality of the produced imagery to be processed by the system SYS. The intensity values (and hence the pixel values) as captured in the recorded imagery can be influenced by changing the parameters and this is frequently done because different phases of the medical procedure may call for different imaging settings as usually described by medical imaging protocols. In X-ray imaging, the imaging parameters include for instance settings of the imaging geometry. The imaging geometry describes the spatial relationship between the imaged patient or at least a region of interest ("ROI"), and the X-ray source and/or a plane of the detector D. The imaging geometry thus determines in particular the projection direction d. The imaging geometry determines the current FOV. The imaging geometry and thus the FOV may change dynamically during the intervention as requestable by the user setting different imaging parameters. Other imaging parameters of the imaging geometry may include a collimation parameter. A collimation parameter pertains to a collimator (not shown) of the imaging apparatus IA. The collimator may comprise a number of X-ray opaque blades which can be adjusted through the operator console OC by setting the collimation parameters to so define an aperture of a desired shape and/or size. Controlling shape/size of the aperture allows restricting or widening the X-ray beam thus further defining the FOV.

The control unit OC may also allow user operation of certain robots that can help in moving or operating the interventional devices over-the-wire such as through a process chain of actuators and end-effectors. An extremely steady hand may be required for certain critical phases of the intervention. Whilst trained surgeons are often very good at this, robots can still assist here especially on days where a large number of patients are treated or in very stressful situations.

The imaging parameters may also influence the very nature of the X-ray beam and hence the manner in which the radiation interacts with patient tissue thus influencing contrast in the captured imagery. The nature of the x-radiation may be determined in particular by settings of the X-ray source XS. In embodiments, the X-ray source XS is an X-ray tube ("tube" for short) including a cathode and an anode. One such imaging parameter may pertain to the amperage and/or voltage of the X-ray tube. Imaging parameters for the tube operation are collectively referred to herein as (X-ray) source parameters. The X-ray source parameters may prescribe in particular the energy of the X-ray beam. Source parameters may depend on the specific imaging protocol or modality. In embodiments, the main application envisaged herein is fluoroscopic X-ray imaging. A C-arm or U-arm imaging system IA as sketched in FIG. 1 may be used for fluoroscopy. In fluoroscopy, the envisaged beam energy is usually in the range of 50-60 keV. Other applications may call for other energy ranges.

One type of (medical) interventions that uses medical devices reside in the imager's field of view (FOV), at least at times, is treatment of cardiac stenosis, or balloon angioplasty, also known as percutaneous transluminal angioplasty (PTA). The FOV is the portion of space that is being imaged by the imaging apparatus. The stenosis may be treated by advancing a distal portion of the balloon catheter BC through the patient (from an entry point EP) to the lesioned site such as the strictured site ST, a portion of a lesioned blood vessel. The distal portion is formed as an inflatable balloon portion. Upon arrival at the target region (where the stenosis is located), the balloon is inflated to treat the stenosis. Caused by the inflating balloon, a force is exerted on the vessel wall VL to broaden the stricture. A guide wire GW may be used to navigate and push the catheter's distal treatment portion to the site ST. A range of different types of balloon catheters are envisaged herein including those of the over-the-wire (OTW) type or rapid exchange (RX) type, or others still.

Other medical procedures or interventions, all envisaged herein, may call for other medical devices, such as in transcatheter aortic valve replacement (TAVR) or transcatheter aortic valve implantation (TAVI) interventions. In these or similar procedures, one or more tools/devices may be resident at least at times in the FOV of imager IA. Some of the tools/devices may be movable and/or may be capable of assuming different shapes/states.

As briefly mentioned above, the (medical) procedure often relies on interventional devices that are used at least during parts of the intervention. Such interventional devices ID may reside at least partly and at times within the patient's body. Such interventional medical devices ID may be introduced from the outside into the patient during the intervention such as the mentioned balloon catheter, guide wire, guiding catheter, microcatheter, introducer sheath, pressure guidewires, robotically steered guidewires and instruments, sensing catheters, imaging systems such as transesophageal echocardiography (TEE) probe or intravascular ultrasound (IVUS) or an optical coherence tomography device, any catheter with sensing capabilities e.g. spectral sensing, a laser atherectomy device, a mechanical atherectomy device, a blood pressure device and/or flow sensor device, needles, ablation electrodes, cardiac electrophysiology mapping electrodes, balloons, endographs, stents, stent retrievers, aneurysm coils, and a plethora of other therapeutic or diagnostic tools such as mitral-valve clips, pacemakers, implants, other artificial heart valves, blood vessels, etc.

The imaging apparatus IA and the computer implemented system C-SYS together form an image guided therapy or diagnosis system that supports user in performing therapy and/or diagnosis intervention in relation to a patient.

An example of such an intervention includes treatment or diagnosis of coronary artery diseases as described above. Other inventions in relation to the heart include implanting of cardiac devices such as pacemakers, for example. Other types of vascular inventions relate to the peripheral vasculature, such as treatment of thrombosis or varicose veins. However, interventions around the circulatory and/or vasculature system are not at the exclusion of other inventions such as bronchoscopy for diagnosis of treatment of lungs, interventions for treatment or diagnosis of biliary ducts or urological system, and others still.

A medical intervention is a medical procedure. Medical procedures differ in type and may be made up of a number of different phases, such as the navigation phase. Different phases may call for a different type of medical instruments or implements to be used, may call for administration of different type of medication, scheduling and logistic to manage the medical procedure by summoning suitable staff with the requisite medical expertise, allocating resources of follow-up treatment or diagnosis, etc.

Operation of the imaging apparatus IA ("imager") may be controlled from the operator console OC by adjusting certain imaging parameters that influence the type and quality of the imagery acquired. For example, the imaging apparatus may allow adjustment of its imaging geometry to so acquire images at different FoV that are best suited for a specific type and/or phase of the medical procedure. For example, at different phases of the medical procedure, a pose in 3D space of the detector D and/or the source SS may be changed relative to at least a part of the patient so imagery along different projection directions p can be acquired. Adjustment of the imaging geometry, and hence of the FOV, may be automatically requested by the control system C-SYS, or may be controlled by a robot or by a human operator. X-ray imaging of the projection or tomographic type such as CT or radiography respectively are not the only imaging modalities envisaged herein. Other imaging modalities may include ultrasound, MRI and nuclear imaging.

The image-guided support allows acquiring live imagery of the internals of the patient and thus monitoring the position of the device ID inside the patient in relation to surrounding anatomy and the target site, such as lesion or other specific area for the intervention. As mentioned, a stream of such imagery may be acquired to support navigation of the device ID to the lesion for example. Such type of imagery represents image-guided-support of the intervention. Whilst image-guided support for minimally invasive type interventions such as the ones mentioned above are useful, this may come at a cost. Imaging equipment is expensive, complex, need maintenance to absorb wear-and-tear effects during extended use. Cathode disks in X-ray tubes sources SS ("tubes") of X-ray type imagers for example are repeatedly subjected to extremely high temperatures and temperature gradients, and need replacement. In addition, some type of imaging modalities, such as X-ray and nuclear, use ionizing radiation, thus incurring a radiation dosage cost for patient and staff that needs to be balanced against the benefits. Patients may sometimes require a contrast agent to be injected to boost contrast in the images, but this can have negative health implications for patients. For example, contrast can damage the kidneys.

In order to reduce reliance on imaging equipment IA, the computer implemented support system SYS includes a control component SYS that facilitates, navigation of an interventional tool IT within the patient without the use of imaging equipment and imagery. No image needs to be acquired to learn about a location of the medical device ID. As will become apparent shortly, instead of or in addition to navigation support, the control component SYS may be used to control other types of system of device Dj preferably during the medical procedure. Whilst in principle the proposed control system C-SYS could replace imaging entirely, this is not necessarily envisaged herein in all embodiments. That is, a co-operation of the imager IA and the newly proposed control system C-SYS is envisaged herein to help reduce the frequency of use of the imager IA and reliance on imagery during the medical procedure.

Broadly, the proposed control system C-SYS may gather non-image-based information about the anatomical location where the interventional device currently resides. This information may be rendered into a graphic display and can be displayed on the display device to the user as an indication of a current location of the interventional device ID. In addition or instead, based on the so gathered location, the system may control other aspects of the medical procedure, such as controlling any one or more of the devices or systems Dj as may be called on at different phases of the medical procedure.

To achieve this non-image-based location information gathering, the control system C-SYS may include, or is at least co-operative with, a shape sensing system SSS. The distributed sensing system SSS is configured for shape sensing without using ionizing radiation. The shape sensing system SSS may include preferably a device (referable herein as the "(shape sensing) arm A") of elongated shape as indicated schematically in FIG. 1. The arm A, as will be explained in more detail below, allows measuring its own shape as it deforms during navigation within the body. The arm may be coupled to the interventional device ID so it deforms, when the device is used or moved during the intervention. Specifically, in some embodiments the shape sensing system measures deformations along the length of its elongated arm A to reveal a 3D curve as a geometrical indication for the arm A's current shape. The 3D curve is represented by shape measurements generated by the arm A as a result of its deformation. In simpler embodiments of the shape sensing system SSS, measurements of a mere 2D curve may be sufficient. The nature of the shape measurements, denotable herein as italicized "s", will be explained in more detail below. It has been found that the spatial information, as captured in the shape measurements, representable by a 3D curve, can be correlated to the respective anatomical location where the arm A currently resides. The shape measurements themselves may be correlated. The anatomical location inferable from the shape measurements s can be used to control the said other devices $D_j$, including the display device DD where an indication on the current anatomical location $LA_i$ may be indicated graphically, textually, or both. Control by the control system based on the current shape measurement s of the device(s) Dj may be through a suitable control interface CIF.

As briefly mentioned earlier, in use, the shape measurement collecting arm A may be integrated, or at least attached to, an elongated portion of the interventional device ID to run alongside it, so that both are deformed in the same manner during the intervention. In response to the deformations, different shape measurements are acquired over time and are analyzed by the newly proposed control system C-SYS to infer the current anatomical location of the arm A/interventional device ID, based on which the one or more support devices/systems $D_j$ may be controlled. As in most embodiments, the arm A and the interventional device are so coupled, so that a reference to shape or deformation of the arm A may also be read as such as a reference to the associated interventional device ID, or vice versa. The shape sensing arm A us preferably arranged to run alongside an elongated interventional device. The shape sensing arm A when used together with interventional device, thus makes the interventional device into a shape sensing interventional device. The use of shape data as proposed herein may be "extended" to additional (as such non-shape sensing) interventional device(s) by suitable coupling devices, such as a hub device described in WO 2017/055620 or WO 2017/055950. The two interventional device may be registered with respect to each other. Such a registration may be performed for instance via the said hub device that is configured to receive at least parts of both interventional devices, In this manner the shape data is imparted on two or more interventional devices. Thus, the shape sensing arm may be directly or indirectly coupled to one or more interventional devices. However, use of the shape sensing arm A in combination with one or more such interventional device does not exclude herein a possible use scenario, for example during exploration, that the arm A may be used on its own, without an associated interventional device ID.

The shape measurements s may be stored in a database DB as will be described in more detail below. The newly proposed shape measurement-based control system C-SYS may be beneficially implemented by a machine learning module MLM.

Figure 2:
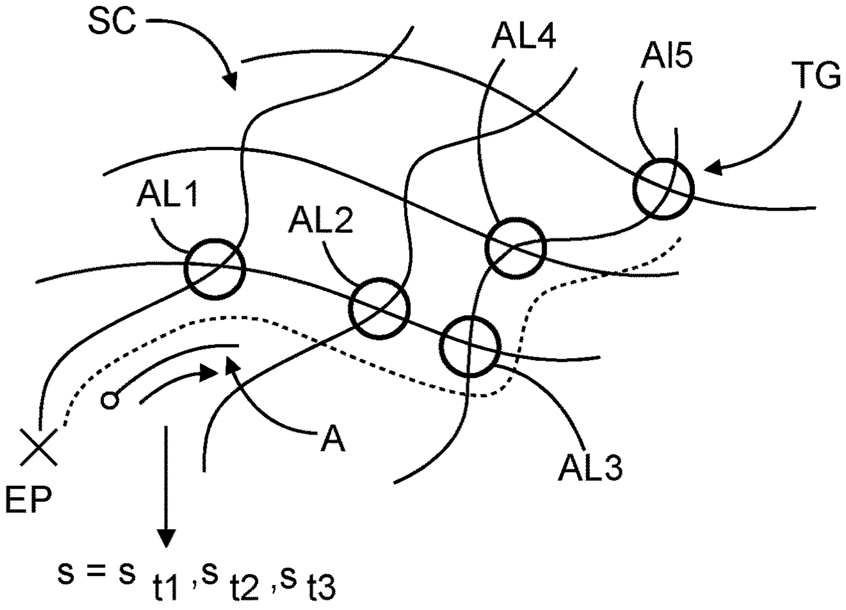
FIG. 2 illustrates operation of a shape sensing system as may be used in the arrangement of FIG. 1.
Figure 2:
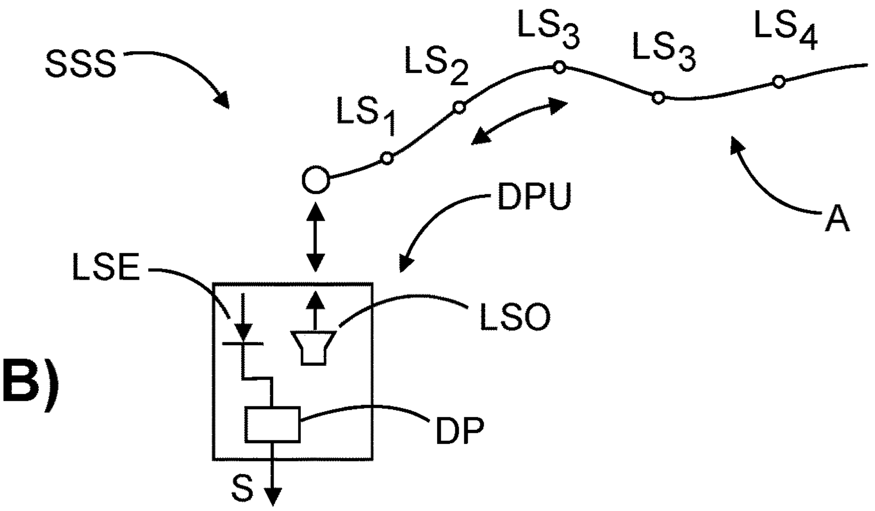
Figure 2:
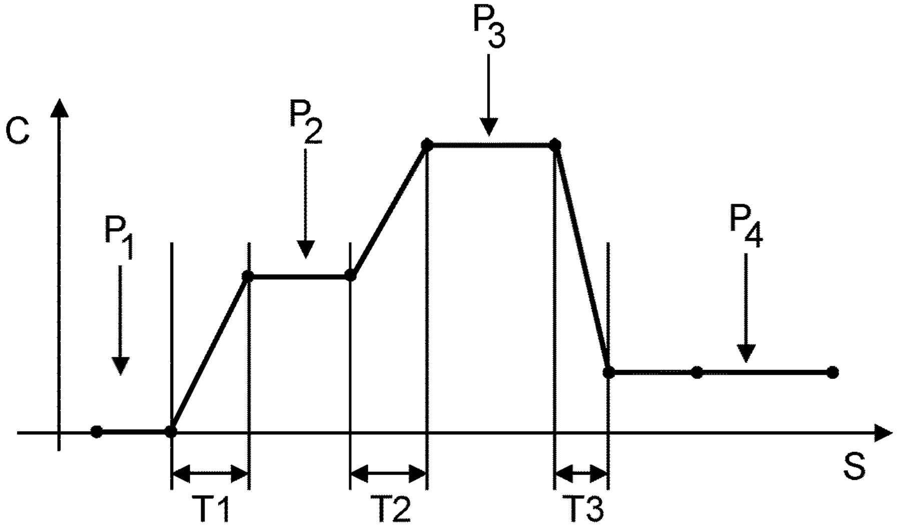

FIG. 2 is an illustration of a principal of operation of the proposed shape sensing control system C-SYS.

A common feature of the above described medical procedures is illustrated in the diagram of FIG. 2A. The above described vascular, bile duct, or urological interventions can be understood generally and as a task of exploration of a complex system of cavities SC. In a simplified and highly schematic manner, the system CS is indicated in FIG. 2 as a system of intersecting lines. The system of cavities SC and as sketched in FIG. 2A, may be thought of a network of interconnected tubes, with junctions. The task for the interventionist is to advance the interventional device ID, such as a catheter, from an entry point EP to the target position TG along a path (shown in dashed line type). For ease of representation, the path in FIG. 2A is shown to run alongside the system CS—it being understood that the arm A's path runs within the system CS. The entry point may be a natural orifice or may be created via an incision in the body. During navigation, the interventional device ID is threaded along the tubular structures. Tubular junctions, indicated as simple intersections of the lines in FIG. 2A, will need to be navigated successfully in order to arrive at the target location TG, such as a stricture in a given artery or vein of the patient's heart. Not all of the intersections or branch points may necessarily be simple bifurcations but may be multifurcations that fork into multiple tubes making the navigational challenge even harder. However, for simplicity we will refer to the bi- or multifurcations as junctions herein with the understanding that more than two tubes may intersect at the said intersections.

The interventional device on its passage from the entry port EP to the target TG will pass a number of anatomical locations AL1-4. For illustration, only four are shown, but there may be more or fewer. By taking the "right" turn at each junction, the arm A/device ID arrive at the target. Some or each such junction may be representative of a respective different anatomical location. By taking the right turn for a given medical procedure, the interventional device is forced to assume a certain shape in order to conform to the curvature and course of the tubular structure and junction thereat. Because the distributing shape sensing arm A is attached to or integrated with the interventional device, the arm A likewise experiences the same deformation which will elicit different shape readings at different time instances T1, T2, T3, during the passage towards the target TG at different such locations AL1-3. The shape measurements $s_j$ can hence be seen to be correlated to respective ones of the anatomical locations $AL_j$ as shown in FIG. 2A.

FIG. 2B provides more details on the shape sensing system SSS as envisaged herein in some embodiments. In some embodiments, but not necessarily all embodiments, along the length of the deformable arm A there are arranged local shape sensors $LS_j$ at suitable increments ΔL. The local sensors $LS_j$ of arm A are in wired or wireless communication with a data processing unit DPU of the shape sensing system SSS. The data processing unit, or interrogator, may comprise or may communicate with a light sensor LSE and a light source LSO. The source LSO is operable to transmit light signals to the local shape sensors LSj and the light sensor LSE captures the respective light contributions reflected off by the localized shape sensors LSj, or otherwise caused by the localized shape sensors LSj. A data processor component DP, preferably including a A2D (analog-to-digital) conversion stage, processes the reflected lights signals into numbers that represent the shape measurement s.

The arm A may include one or more optical fibers with integrated fiber Bragg gratings (FBGs) used as strain sensors for detecting shape information and providing shape sensing data indicating the shape of the shape sensing device, as is well known to one of ordinary skilled in the art. For example, the shape sensing system SSS may be implemented using Fiber Optic Real Shape (FORS) technology, in which case the shape sensing data comprises FORS data that includes but is not limited to the 3D shape of the shape sensing device 140, curvature, and axial strain. As an alternative to fiber-optic Bragg gratings, and envisaged herein in embodiments, the inherent backscatter in conventional optical fiber can be exploited. One such approach is to use Rayleigh scatter in standard single-mode communications fiber. In alternative embodiments, the shape sensing system SSS may be implemented using shape sensing technology other than optical shape sensing. For example, the shape sensing system SSS may include transducers, electrodes and/or electromagnetic sensors, such as piezo-electric sensors, arranged along at least a portion of the arm A, such that the sensing system SSS is capable of determining shape of arm A. For example, if three or more electromagnetic sensors are attached to the arm A, then a shape may be determined from the three positions, thus providing a location and orientation for the arm A and hence for the device ID associated with the arm A. Generally, the more sensors there are arranged on the arm A, the better shape resolution and accuracy. FIG. 2B shows a sensing system SSS with a single arm A, but other multi-am systems with more than one such elongated arms are also envisaged to capture more complex shapes. The shapes measurements may then be represented as curves with bi- or multifurcation(s). Shape sensing sheets instead of the elongated (non-imaging) probe/arm are also envisaged herein, to capture shape measurements as surfaces rather than as lineal curves parameterizable by a 1D parameter.

It will be understood that whilst the arm A is usually attached or integrated into a respective interventional device ID this may not necessarily be so in all embodiments. In some alternative embodiments, the arm A may be used on its own advancing through the patient although this may be of a lesser interest herein for most medical applications. However, it may still be considered for exercise of pure shape exploration for diagnostic purposes. Such shape explorations may be of interest also in the non-medical fields, for example in exploration of plumbing system of cable/hosework in machinery, such as engines, or hydraulic systems of ships, airplanes or motorcars, etc. In such stand-alone embodiments, but also in those wherein the arm A is attached to the interventional device ID, the elongated deformable arm A may be formed from a bio-compatible material, such as a polymer of suitable stiffness, with the FBG sensors or any other sensors embedded therein and arranged along the length of the arm A.

Whilst a number of embodiments of the arm A/shape sensing system SSS has been described above, any shape sensing technology is envisaged herein, so long as it allows determining the shape of the device ID/arm A by measuring shape quantities such as strain, curvature, bending, twisting, etc., of the device ID/arm A, or any other quantity representative of such (geometrical) shape.

Referring now to FIG. 2C, this shows a qualitative diagram that illustrates the relation between the different anatomical locations ALj and shape measurement readings s shown along respective axes of the diagram in FIG. 2C.

The respective anatomical locations will be identified mostly by characteristic curvature patterns that are recorded by the shape measurement arm A as it advances either with or without the interventional device through the tubular system of interests such as through the patient's vasculature for example.

The interventional device ID plus the arm A associated therewith is moved in certain increments, preferably small, through the tubular system of interest, as this has to be done carefully by the interventional robot or user, in order to avoid injury. The arm A also has a certain length, say 10-30 cm, and it can be seen in conjunction with FIG. 2A that not all consecutive shape measurement readings relate to different anatomical locations of interest. Some measurements, especially those taken consecutively, may relate to the same anatomical location ALj as shown by the plateaus of Pj of the measurements graph of FIG. 2C.

As the arm A is made to snake its way from a given anatomical location to the next, once certain characteristics of the shape measurements changed sufficiently, this may then indicate arrival at the said next anatomical location encountered in the arm A's passage through the patient. This change occurs gradually. Therefore there will be certain transition regions T1-T3 between the plateaus P1-5 where the measurements will not yet correspond (fully) to either of the anatomical locations, the one it just transited, and the one the arm A will arrive at next. Whilst not excluded herein, it can thus be appreciated that the term "anatomical location" as used herein will not in general indicate a point location but may indicate a range or region of locations that give rise to certain characteristic shape measurement readings, as recorded by the arm A as it passes through the said location.

Considering FIGS. 2A-C as a whole, it becomes apparent that there is a latent relationship or mapping between, on the one hand, the different anatomical locations, and the time series of shape measurements collected by the arm A during use. It is this latent relationship or correlation that the proposed system C-SYS is configured to harness. It will be difficult to model this latent relationship between anatomical location versus shape measurement exactly and analytically. However, it has been found herein that machine learning approaches do not require such analytically exact modeling but are capable of ascertaining at sufficient accuracy the said latent relationship based on training data.

The training data TD preferably includes previous shape measurements collected from a suitable wide range of patients in respective interventions conducted in the past. The training data may hence represent historic shape measurements collected for different patients of different bio characteristics. In some cases, it has been observed that historic measurements for a single or very few, such as 5 or fewer patient(s), may be sufficient training data. The training data should represent shape measurements collected for the medical procedure of interest but may also relate to different procedures involving the same anatomical regions, such as cardiac vasculature etc. In other embodiments, the previous shape measurements may relate to shape measurements collected for the same patient in earlier medical procedures, or in fact to shape measurements collected at earlier time points in the current procedure. This later embodiment is particularly useful in connection with the paradigm of dynamic learning as will be expanded upon more fully below. In addition, in any of the above-described embodiments, the previous measurements may not necessarily stem from previous in-situ measurements conducted in real medical procedures, such as in the described interventions, but may have been in fact synthesized by the user automatically via computer simulations or laboratory in-vitro (phantom) or in-vivo (animal model) setup. Again, this later aspect of synthetic training data generation will be explored in more detail below.

In machine learning ("ML"), the training data can be collectively analyzed to ascertain the latent relationship of anatomical locations versus shape measurements. Thanks to this analysis, ML is capable of predicting the anatomical location given a new shape measurement not taken from the training data, but newly measured in a given future or new intervention where the shape sensing arm A is used.

Figure 3:
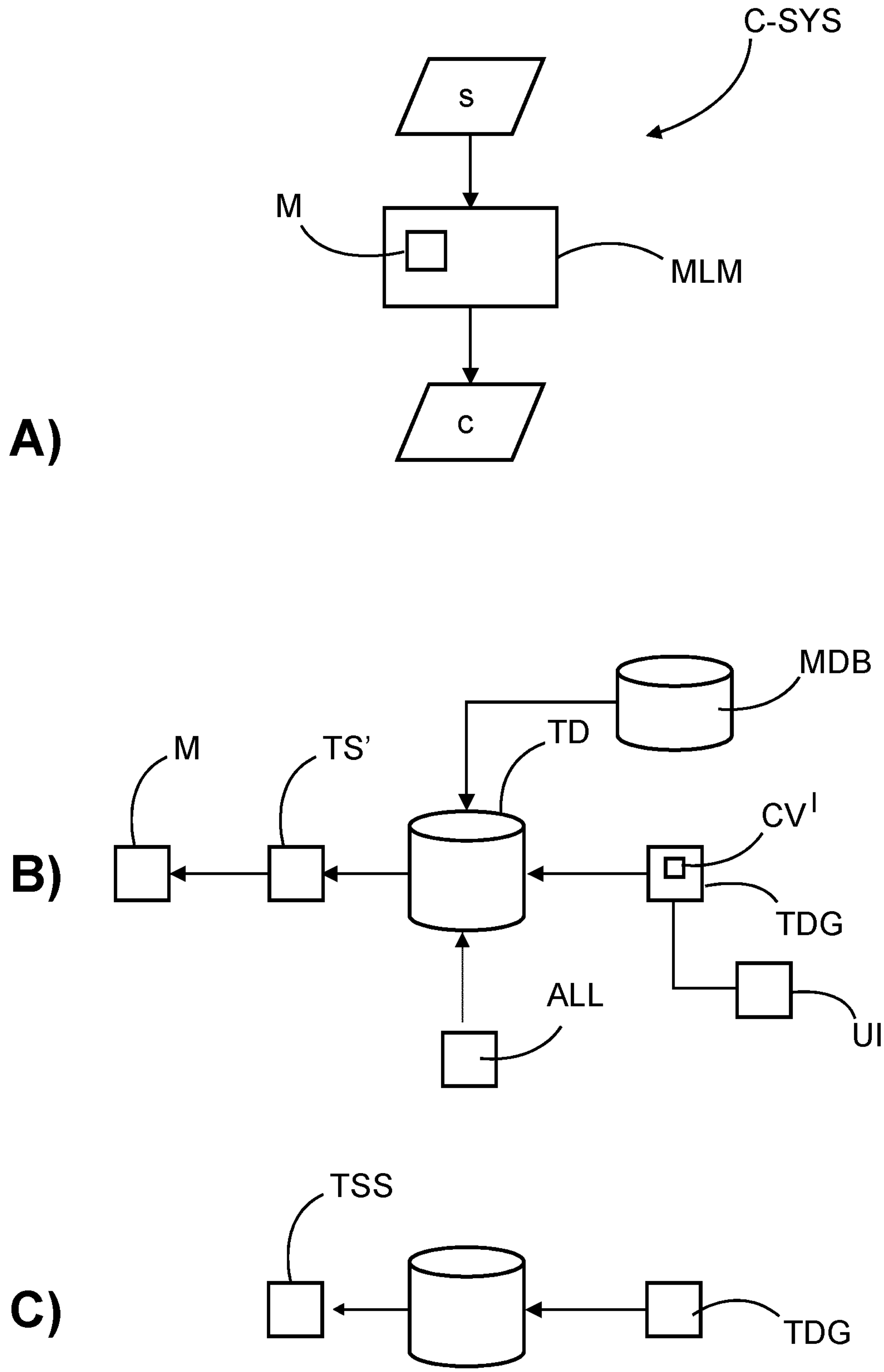
FIG. 3 shows a block diagram of a control system as may be used in the above arrangement and capable of processing shape measurements and of a training system for training a machine learning module.

Reference is now made to FIG. 3A which shows a block diagram of the control system C-SYS envisaged herein.

As mentioned, the system CSYS is based on machine learning and includes a trained machine learning module MLM. The module may employ a machine learning model M that has been processed in a training or learning procedure (which will be described further below). Once sufficiently trained, the system CSYS is ready for deployment and can take in new shape measurements as collected during a given intervention to predict the anatomical location during clinical use.

In deployment, a current (new) shape measurement is processed by the trained machine learning module, for instance is applied to the model, to yield a result such as a category c. In other words, the machine learning module may attempt to categorize the new shape measurement into a category from plural categories $c_j$. Each category c is preferably associated or related to a given respective anatomical location ALj. The category result c so computed may either be used directly as it is, or may be converted or mapped into another information item or result of interest, such as an indication of the procedure type or phase. The conversion by a converter CV may be done by non-ML means such as by a table or database look-up or LUT. The category c or converted into result CV(c) may then be used to control any one or more of the mentioned devices Dj, such as a monitor or display device DD or an augmented reality headset etc. The anatomical location, type or phase of procedure may be visualized as a graphics display and displayed on the monitor or in the headset. Other applications of the categories computed by the machine learning module will be discussed in more detail further below.

The computerized system, and in particular the machine learning module, may hence be understood to be operable in at least two stages or phases such as a learning/training phase or a deployment phase. Generally, the training phase involves computational processing of the training data in order to learn the above mentioned latent relationship, such as correlations between anatomical locations versus shape measurements.

If a sufficiently large and representative training data set is used that exhibits sufficient variants that allows capturing this latent relationship, the machine learning model may be considered sufficiently trained at the end of the training phase, and is then ready for deployment as shown in FIG. 2A. Relatively large training data (for example, N>>100, depending on application) that encompass a wide range of experiences (for example, patients with different anatomy, users that manipulate interventional devices ID differently, or different interventional devices ID, shape sensing equipment with different degree of wear and tear, quality of calibration) will improve the performance of the training model and will represent the expected scenarios likely to be encountered during clinical use well.

Preferably, the learning is not a one-off operation (although this may still be so in some embodiments) but is rather repeated one or more times at certain intervals/rate during deployment. The learning may be retriggered if a new category of shape measurement is encountered in deployment, that is either not at all, or not sufficiently well represented in by the original training data set. This type of dynamic learning allows an on-going adaptation of the machine learning module MLM, in light of new data that comes before it during deployment.

The block diagram in FIG. 3B is an illustration of the training phase as opposed to the deployment phase in FIG. 3A. A computerized training system TSS is used that computationally processes the training data including in particular, historic shape measurements, as held in the (one or more) training database TD. The training data may relate to the same patient in a current or earlier medical procedure, or to one or more different patients from earlier medical procedures, as described above in connection with FIG. 2. In dynamic learning embodiments in particular the control system C-SYS for deployment and the training system TSS may be integrated into common system, implementable on a single or plural computing systems, or as a part of federated learning framework. If the latter, preferably the computing systems should be communicatively coupled in a communication network. Alternatively, in particular when the training is envisaged as a one-off, or if it is anticipated that training will be rarely done, the control system C-SYS and the training system may be run on separate computing systems. The trained model M may then be ported by data transfer though a network (or by using a portable storage means, etc.) to the computing system of a medical facility where the control system is to be deployed and run in clinical use.

The training data can be retrieved and accessed from medical databases such as PACS or other medical/patient records MDB. The training data may be sourced manually. Alternatively, a computerized search may be formulated by using a database language or scripting language.

It may not always be possible to source a sufficiently large and/or representative number of training data specimens. In such cases, a training data generator TDG is envisaged herein which allows artificially or synthetically generating previously non-existing training data specimens. This can be done either fully automatically or can be done by involvement of the user through a suitable user interface UI as will be described in more detail further below.

The training system TSS applies a training/learning algorithm to the training data to adjust a model M. More specifically, the adjustment of the model based on the training data may be referred to herein as training or learning.

FIG. 3C shows a diagram of the described training data generator TDG. An existing training data set is topped up by synthetically generated training data specimen. In other words, artificially generated shape measurements are added to an existing stock of "real" historic shape measurements or the training data set TD is built up from scratch entirely from such synthetically generated measurements.

Once a sufficient number, with suitable variation, of such shape measurements has been obtained, either by artificial generation or by retrieval from historic, existing shape measurements from medical databases, these can be passed on as training data to the training system TSS. The training system TSS processes the training data to adjust the model as mentioned above in FIG. 3B. Training and generation of training data will be revisited in more detail below.

Figure 4:
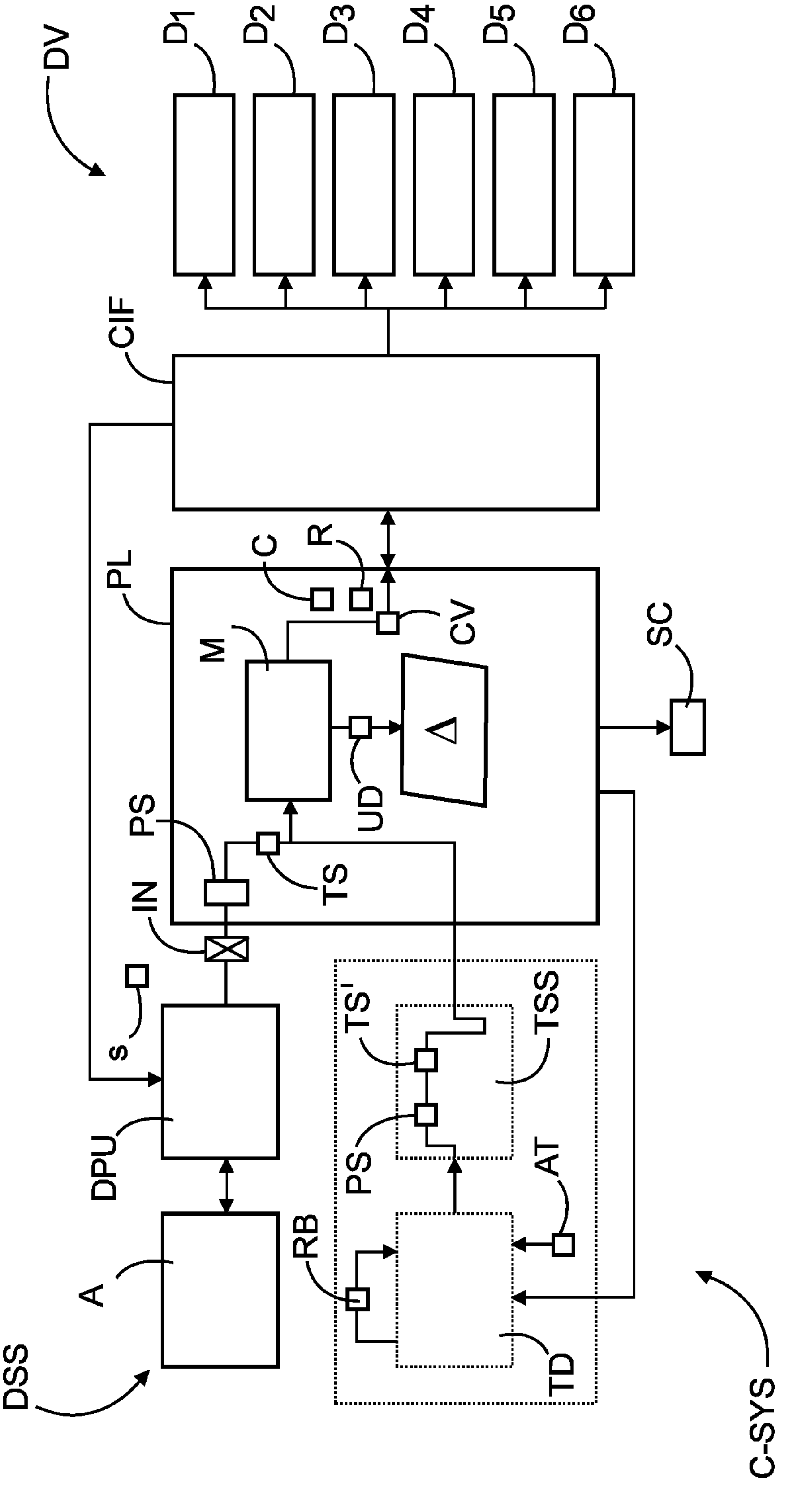
FIG. 4 shows a more detailed block diagram of the control system including a trained machine learning module.

Reference is now made first to the block diagram in FIG. 4 which shows in more detail components of the proposed control system C-SYS.

During deployment, the deformable shape sensing arm A of the shape sensing system SSS is deformed and generates the above-mentioned stream of signals issued by the local sensors LS along the arm A. The stream of signals may then processed by the data processor DPS of the shape sensing system to produce shape measurement s at certain times. The shape measurements s are received at the input interface of the system C-SYS.

Operation on per shape measurement instant is envisaged in one mode, and so is aggregated per-block-operation mode, in which shape measurements collected in a certain time period are buffered and then passed on, as a block, for processing by the control system C-SYS. Unless described otherwise herein, no specific distinction will be made herein in respect of the two modes. A reference to shape measurement s may hence be construed as a reference to a single measurement datum at a given time instant, or to multiple such measurements for multiple time instants.

The control system C-SYS includes a predictor logic PL. The predictor logic PL includes the trained machine learning module MLM which receives through the interface the shape measurements s. The machine learning model M is applied to the shape measurement to yield as output the category c which is indicative of a respective anatomical location, a phase of the procedure, or a type of procedure.

The predictor logic P1 may not necessarily use only ML-based logic to process the shape measurement s into predicted categories. The system C-SYS may further include one or more auxiliary logics to process contextual data κ, in particular to resolve ambiguities or uncertainty in relation to the ML predicted categories. The predictions can thus be made more robust. Alternatively, it is the ML-based logic PL that processes both, shape measurements into the predicted categories.

The concept of contextual data κ will be explored in more detail below. One particular type of contextual data is time, in particular the chronological order in which the categories are predicted ("prediction time") in the course of the intervention. The order of previous predictions in a current intervention can be used to inform the next prediction. The processing of the time information, in particular the order of earlier predictions (prediction time), can be done by the machine learning model in conjunction with the current shape measurement to predict the next category. Alternatively, the mentioned auxiliary logics compare the order of the predicted categories against an expected order stored as a look up table. Operation of the aux logic may thus nor necessarily involve ML but may be done by look up operations, interpolations. etc. Only when there is conflict between what the ML-based prediction logic PL predicts and what the auxiliary logic expects, is the remedial action taken, such as updating the training database, e.g. opening of a new category, or re-learning the model M, etc., as will be described herein in more detail.

If desired, and as briefly mentioned earlier, the conversion stage CV may convert the predicted category c into another result R, CV(c), such as into the applicable phase of the medical procedure or indeed may indicate the type of medical procedure as desired. The converted result R or the category C may be output suitably coded such as numbered data which may then be forwarded to the control interface CIF. The control interface CIF may include middleware which allows controlling one or more of the devices or systems Dj={D1-D6} as exemplary shown on the right-hand side of FIG. 4. The middleware may map the predicted category c/result into suitable control commands. A lookup table or other structure may be used.

The devices Dj may include visualizer module D1 that effects displaying a graphics display/visualization of the result or category graphically, textually or both on the display device such as a monitor in an operating theatre and/or a projection on a screen, or the control of the augmented reality headset which is worn by the user during the intervention.

Visualization module D1 may generate a graphics display based on prediction result, including current anatomical location, type of procedure or phase thereof. The interface CIF controls video circuitry to effect display of the graphics display on the display device DD (or on a different display device). The graphics display so generated is dynamic corresponding to the dynamic nature of the predictor logic: the graphics display is adapted based on the stream of the predicted categories, as the arm A acquires a stream of shape measurements whilst being moved in the intervention. When the predicted categories are indicative of the respective anatomical locations, position of a graphical widget in the graphics display may be updated with each newly predicated category. For example, a cursor widget, such as a circle, hair-cross symbol or other, may be displayed against a graphical rendition of patient anatomy, such as an anatomical atlas or similar, to indicate the anatomical location in context. Purely textual information, or textual information in addition to graphical, such as a textbox including a string, for example "current anatomical location: inferior aorta", is also envisaged. The current shape measurement may also be rendered in a graphical view on the same or a different graphics display in a different view pane. The user may be able to switch between different such panes. Specifically, as a visual check aid, the current shape measurement may be visualized versus a graphical rendition of the training data clusters, similar to FIG. 5. The current shape measurement may be displayed in association with its predicted cluster, with other one or more clusters also displayed in other parts of the graphic display. User can hence check visually very quickly whether the predicted cluster is sound. A planned path for the procedure may also be displayed, if required. If the predicted category is indicative of the procedure type or phase instead of anatomical location, the graphics display may include a time line or time diagram with portions indicative of the phase. The graphics display is dynamically updated so that the graphical widget appears to visually progress or "move" along the line/diagram to indicate the current phase, in response to the predictor logic predicting the categories over time. In yet other visualization embodiments, the graphics display may include a virtual image of a reconstructed shape of the shape sensing device, optionally together with a virtual and/or imaged representation of the anatomical location. The virtual representation may include computer graphics elements, CAD elements or other. In addition or instead, a virtual and/or imaged representation of a next anatomical location likely to be passed or entered into by the shape sensing device is included in the graphics display. Optionally, a navigation path of the shape sensing device A,ID is represented in the graphics display. Optionally, and possibly in addition, the current and/or next anatomical location is represented in association with the said path, such as a dynamic widget superimposed on the path rendition, the widget apparently moving along or on the path as the predictions are updated by logic PL. In yet another embodiment, in combination with any of the aforementioned embodiments, a representation of the planned path of the navigation is included in the graphics display, as may be known a priori, or derived by the logic PL from earlier predicted results. In some embodiments, the graphics display includes an indication of a newly predicted anatomical location, possibly associated with a new associated organ entered into by the shape arm A. The said next anatomical location and the newly entered into location/organ, phase or type or procedure may be obtained by analysis by logic PL of the time behavior of the stream of earlier predictions and/or certain changes in characteristic of the computed categories, such as in the shape measurement clusters as will be explained in more detail below.

Other devices envisaged to be controlled include the imaging system D2 such as the imaging apparatus IA, whose imaging parameters are changed in response to the computed category and/or result. The FOV may be changed according to the current phase the procedure is in or according to the current anatomical location, etc.

The one or more controllable devices Dj may include a monitoring device D5. The monitoring device D5 may monitor for vital signs of the patient. An operation mode of the monitoring device D5 may be changed, based on the predicted category c. For example, the sampling rate of the monitoring device D5 may be adjusted, or any other setting. The medical device may include instead or in addition a database module D4. The controllable devices may include the interventional device D3=ID itself. For example, the power supplied to the interventional device ID may be controlled as function of the category c predicted by logic PL. The powered interventional device ID may be an atherectomy catheter where the laser power may be adjusted. Another example may be for tuning imaging parameters for imaging catheters; for example, in IVUS (intravascular ultrasound) or ICE (intracardiac echo) catheters.

The controlled device D6 may include a management device to direct or manage clinical workflow, such as a communication device that pages or otherwise transmits a message to clinical personnel based on the result, category c predicted.

Whilst processing by the logic PL of the shape data s as raw data, as is envisaged in some embodiments, this may prove inefficient to process. For instance, the data may include noise contributions or may be otherwise difficult to compare. To improve processing, a data preparation stage PS may be provided, that pre-processes the shape measurements to thus facilitate efficient processing. For instance, the preparation stage PS may be configured for filtering, such as noise filtering, or may be configured to perform a normalization operation to normalize the data s as will be described in more detail below.

In addition, or instead, the data s may be too high dimensional, where several dimensions of data may be redundant or may not contain task relevant information. High dimensional data may also cause the processing logic PL to consume excessive computational or memory resources. To boost computational efficiency and/or usage of memory resources, a data transformation stage PS may be provided, that transforms the shape measurements into a representation that facilitates more efficient processing. For example, the transformation stage may be employed to reduce the dimensionality of the data s, thereby using only the most relevant aspects of the data and to so foster more efficient operation. For example, a principal component analysis (PCA) or other factor analysis algorithm may be used in transformation stage TS to simplify representation of the shape measurements s. The shape measurements acquired over time may be conceptualized as several discrete elements ("points") of a high dimensional space such as a vector space having coordinates relative to a basis made up of basis vectors. In dimensional reduction ("DR") techniques of the projection-based such as is PCA or other factor analysis techniques, said points are projected onto a lower dimensional sub-space that allows a simpler representation, such as in terms of fewer coordinates relative to new, smaller basis with fewer basis vectors. Other types of dimensionality reduction techniques are also envisaged herein such as various PCA-variants (kernel based, graph-based etc.), but also others, such as statistical techniques for example LDA ("linear discriminant analysis"). LDA finds linear combinations of features to separate the underlying set of training data specimens into components to achieve simplified representation and hence computer-implementation advantages. However, the paradigm of "simplification by projection" that underlies at least some aspects of some of the foregoing DR techniques is not necessarily required in all implementations envisaged herein. For example, DR techniques of the feature selection type are also envisaged herein, where certain members from the set or certain properties ("features") thereof are designated as representatives and further processing is then based on those representatives. Such feature selection regimes may be driven by information theoretic quantities, such as mutual information, Fisher information, or others. Transformation into representations of smaller or greater sparsity is also envisaged herein in embodiments, sparsity being yet another example of a different representation of the data.

The above being said, it may be worthwhile pointing out that such change of representation algorithm as implemented by the transformation state TS is not necessarily of the dimensional reduction type. For example, whilst processing of the shape measurements in time or spectral domain is mainly envisaged herein, the transformation stage TS may support transformation into frequency domain by suitable Fourier or Wavelet operation. The transformation stage TS will be described in more detail below. In general then, the transformation stage TS may be implemented by any algorithm that transforms the set of shape measurements s into representations that confer an implementational advantage for the predictor logic PL, such as more efficient processing (e.g., quicker, low latency turnaround, etc.) and/or conservative memory usage.

The machine learning module may operate as mainly envisaged herein, as a multi-class categorizer that categorizes the shape measurements into one of a number of categories for the different anatomical locations of interest $AL_j$. Each category $c_j$ represents a different, given anatomical location of interest $AL_j$. Some machine learning models may allow computing an uncertainty or prediction error Δ associated with some or each of the computed category c. The system may thus include an uncertainty determiner UD. The mapping between category and anatomical location is achieved in some embodiments by training, for instance by using suitably labeled shape data in a supervise training scheme. For example, the early mentioned synthetically generated or sourced historical training data may be assigned by a human expert with a label that indicates the respective anatomical location. A visualization of shape measurements as 3D curves may allow an experienced user to guess the respective anatomical location such as the iliac-aorta transition or other portion of interest of the human or mammal vasculature.

Computation of the prediction error Δ by uncertainty determiner UD is particularly useful in conjunction with the dynamic learning embodiment briefly described above. In dynamic learning the training phase is not done as a one-off operation once before deployment, but the training phase is rather conceived as an on-going operation during deployment and is based on the new data the system encounters during deployment. In this optional dynamic learning/training embodiment, the system C-SYS may further comprise the training stage TS in co-operation with the prediction logic PL. In one example, if the prediction error returned by uncertainty determiner is high, for instance higher than a certain threshold, a warning signal is issued to the user. Alternatively or in addition to issuing such a warning, if the prediction error exceeds a certain threshold, the currently processed shape measurement s that caused the high uncertainty is excluded from the dynamic training and passed on to the training system TSS. Whilst reference is herein made mainly to uncertainty value Δ with increasing magnitude indicative of higher uncertainty, this is not at the exclusion of an equivalent quantification of prediction error in terms of a confidence value. A low confidence value corresponds hence to high uncertainty, and it will be understood that the above described thresholding over Δ will need to be reversed if Δ codes for confidence values rather than uncertainty.

High prediction error may be indicative that a new category of data was encountered, not represented by the training data that was used so far to train the model. In such a situation, a new category may be opened, and the current shape measurement is added to the training memory TD as a new training data specimen for this new category. An automatic or user operable annotation tool AT may be used to annotate the respective shape measurement that caused the logic PL to compute the high uncertainty category. The newly opened category may be representative of a new anatomical location, or an unusually shaped known anatomical location, or indeed may merely represent a transition region between two anatomical locations $AL_j$ $AL_{j+k}$, (k≥1) of interest as described earlier in connection with FIG. 2C. Such category for an "in-between location" that is the transition region, whilst not of interest as such a priori for the task at hand, may still be used with benefit to update the system so that the logic PL can better localize where in the patient body the arm A currently resides. A localization categorization based on the new category that the arm A is currently in between two $AL_j$ $AL_{j+k}$, locations may still be of benefit to the user in terms of navigation. By adding more and more of such transition region categories, the spatial resolution capability of the prediction logic PL can be refined down to any desired granularity. The uncertainty values may be used to assign a measurement to more than one category. The uncertainty values may thus be used to measure and quantify membership to the categories.

The training system TSS may likewise include optionally pre-processing PS' and/or transformation stages TS' corresponding to the pre-processing and transformation stages PS, TS of the prediction logic PL. The operations are preferably identical.

Multiple machine learning techniques are envisaged herein including neural networks and others and these will be discussed in more detail below.

In certain types of machine learning techniques such as in clustering, a re-balancing component RB may be used to rebalance or change the sizes of the clusters so far encountered. This may ensure that the clusters on record are representative enough for the respective locations encountered by the system. Having clusters of sizes big enough so that each or most include sufficient number of different representatives, may result in more robust performance of the machine learning module MLM.

Before turning in more detail to machine learning model implementations of the predictor logic, it may be useful to describe characteristics of shape measurement data s in more detail. Based on the nature of the shape measurements as illustrated in FIG. 2 above, it is apparent that the shape measurements s are spatial-temporal quantities. The shape measurements collectively may be written as $S=(s^j)=(s^j(x^j,t^j))$.

In this notation, index j represents the respective patient of whom the measurements have been taken but this index can be dropped herein. Index x indicates the spatial increment along the arm A where the respective local sensor $LS_x$ is located and where the respective shape measurement has been recorded. Index t indicates time and refers to the different shape readings acquired over time as the arm A is being advanced by user or robot through the patient. However, such indexing by location x is not necessarily required herein, as the shape may instead be defined by a single quantity at a given time t for the whole of the arm A globally, such as by an average value, for example average strain, curvature, etc, or other such global quantity.

The shape measurement $S=s^j(x^j,t^j)$ may comprise any form of measurements obtained by the arm A. For example, the measurements may be obtained from the respective optical fiber of the arm A. The measurements may include, but is not limited to, the curvature, axial strain, twist, or 3D shape of the arm A. The 3D shape may be indicated by a set of spatial 3D coordinates $(X,Y,Z)^x$, indexable by location x along arm A and relative to some coordinate system. For present purposes it is immaterial whether the shape measurement, (the s-values), are represented as spatial coordinates, curvature, strain, or the like and any such semantic format is envisaged herein.

Referring now in more detail to the operation of the predictor logic PL, this can be implemented by machine learning techniques mainly envisaged herein. Some such machine learning techniques use models on which the prediction is based.

The model is a data structure, function or system of functions that allow(s) applying thereto shape measurement data so as to compute the prediction result, for example the category c.

In training phase, the model is adapted or adjusted given the training data. The training data includes synthetically or historic shape measurement data. The outcome of the prediction by the predictor logic PL is preferably one of multi-categorization. That is, in deployment, a newly observed shape measurement collected during an intervention for example, is categorized into one of plural categories. Each category represents a respective anatomical location, a procedure type, or phase of the procedure.

Given a current shape measurement measured by arm A at a given time, the prediction logic PL can hence predict at which of the plural anatomic locations the shape measurement arm A is currently located. In most cases, and given the above described explanation (at FIG. 2) of the characteristics of the shape measurements data being spatially distributed, the term "location" will be understood to mean that the shape arm A extends across the respective anatomical location predicted by the predictor logic PL. If more detailed localization is required, the measurements can be calibrated to respective reference points along the length of the arm A, for example, a middle portion or preferably the end portion of the shape measurement arm A and/or of the respective interventional device ID the arm A is integrated or associated with.

In the training phase, a training or learning algorithm is applied to or in respect of the currently held training data in memory TD. Once training has been completed, during deployment phase a predictor algorithm may use the model to apply the same to deployment phase measurement data. The predictor algorithm processes the adjusted model and newly received shape measurements to produce the prediction result, that is the category of the anatomical location.

The training algorithm may be supervised or unsupervised. In supervised training, each training specimen or shape measurement is associated with previously known anatomical location to which it pertains. In unsupervised learning no such (explicit) labeling (or at least no explicit labelling) is required. Both variants, supervised or unsupervised learning, are envisaged herein. Such examples will be discussed further below and are envisaged in embodiments.

In general, two cases may be distinguished herein, namely that of explicit or implicit ML modeling. Common to both is a model M that maps $s \rightarrow c_j$ shape measurements to a category representative of anatomical location $AL_j \leftrightarrow c_j$. The model is generally one of a multi-categorizer/multi-biner, but a binary categorizer is not excluded herein such as when the objective of the logic is merely to establish or "test" whether the arm A is located at a predefined anatomical location or not.

In some embodiments, the model is a binary or multiclass classifier, where each category represents a classification label c (we use the same notation in this case). However, in other embodiments the model may be one of a cluster or of plural clusters $c_j$, where each category $c_j$ corresponds to a cluster. Each cluster is a respective subset of the training data $c \subset S'$.

From now on, uppercase S' will be used to designate the set measurements $s' \in S'$, and the prime "'" designator will indicate a reference to the training data set S' or specimen s' therefrom. Notation "s" (without the "'" designator), is hence by definition $\notin S'$ and, thus a reference to a shape measurement received post-training, during deployment.

In implicit modeling, it is the training data itself that constitutes the model, optionally including a description function(s) D that describes the specimens s' or subsets $S'_j$ of S', M=(S', D( )). Clustering algorithms envisaged herein in some embodiments as mentioned above, are one example of implicit modelling.

In explicit modeling, the model is represented as one or more parameterized function or a system of functions $M=M^{\Theta}(\ )$ forming a different computational entity from the set of training data S itself. In some embodiments, some or all of the function(s) $M^{\Theta}(\ )$ may have their input and/or output connected by functional composition, such as the nodes in neural network type models, where output from one function is provided as input to one or more other functions, etc. The function(s) $M^{\Theta}(\ )$ map from training set (space) S to the space of categories $C=\{c_j\}$. Other types of explicit modelling envisaged herein include decision trees, random forests, but also statistical techniques such a mixture models, in particular with Gaussian components, referred to as Gaussian mixture models ("GMM").

In explicit modeling, the training algorithm amounts to adjusting the parameters θ of the model function(s) $M^{\Theta}(\ )$, based on the training data S'. In some such embodiments, the training algorithm may be formulated as an optimization process where one or more objective functions F are used to guide the adjustment of the parameters of $M^{\Theta}(\ )$. The model M is deemed sufficiently trained once a pre-defined objective measured by objective function F has been achieved. Objective function may be one of a cost function or a utility function. For example, when formulating the optimization in terms of cost function the objective is to minimize the cost function or at least to adjust the parameters so that the cost falls below a pre-defined threshold:

$$\theta^* = \text{argmin}_\theta \sum_{s' \in S'} F\left(M^\theta(s')\right) \tag{1a}$$

Objective function F is some function, such as distance function, that measures the objective, or cost. The total cost over all or some subset of the training data S' is considered as indicated by the summation. In the context of supervised multiclass or binary classification, (1a) may be expressed more specifically as:

$$\text{argmin}_\theta F = \sum_k \left\| M^\theta(s'), c_k \right\| \tag{1b}$$

$\|.\|$ is some distance or similarity measure/function, configured for classification tasks, such as mean square error ($L^2$ norm) or mean absolute error ($L^1$ norm), or any other. The parameters may be parameters of probability distributions, and in which case $\|.\|$ is chosen as some statistical similarity measure. The notation $\|.\|$ is used in a general sense herein, so is not restricted to $L^p$ norms, but includes more generally similarity measures, such as may be defined in terms of cross-entropy or Kullback-Leibler ("KL") divergence, or others still.

In explicit modelling, following on from (1a,b), the trained model $M^{\theta*}$ may be used to formulate the predictor algorithm as:

$$M^{\theta^*}(s) = c \in \{c_j\} \tag{1c}$$

In implicit modelling, the training algorithm may be formulated in terms of the training set S' as follows:

$$\Pi^* = \text{argmin}_{\Pi} \sum\nolimits_{\Pi} F(\Pi)\ \Pi = \bigcup S'_j,\ S'_j \subset S' \tag{2a}$$

$\Pi$ is some partition which may be defined by the above-mentioned descriptor function $D(S'_j)$ of the subsets of $S'_j$ of S'.

However, some embodiments of learning in implicit modelling may simply involve storing a new category such as in clustering, to simply add a new set $$\prod^{+} = \prod \bigcup S'_k,\ k \neq j.$$

The new category $c_k$ represented by $$S'_k$$

may be a singleton. It may be derived from one (or more) new measurement(s) s encountered during deployment $$S'_k = \{s\}.$$

In addition, in some embodiments the learning phase in implicit modeling may involve no more than storing training data specimens s'∈S', such as in k-nearest neighbors ("k-NN") algorithm as envisaged in some embodiments.

The predictor algorithm may be configured to assign each s to its cluster based on the following optimization:

$$S'^*_j \text{argmin}_{S'_j} \sum\nolimits_{S'_j} F(s, D(S'_j)) \tag{2b}$$

$$\text{and } M(s) = c, \tag{2c}$$

with c being associated with the cluster $$S'_j *$$

as per (2b).

Clustering type machine learning algorithms have been found to be particularly useful for categorizing the shape measurements. Clustering type machine learning approaches are examples of the above-mentioned implicit modeling in ML. Broadly, in such clustering algorithms as envisaged herein, the training data S' set is broken up into sub-sets or clusters that may or may not overlap. This represents a partition operation as per (2a). The clusters $S'_j$ may be described by the descriptor function DO, such as centroids or other characteristic features of each of the clusters $S'_j$. A training data specimen s' of the training data set S' is said to be a representative or member of the cluster to which it belongs, with the centroid $D(S'_j)$ being the respective prototype.

In deployment, the predictor logic PL implements the predictor algorithm to find (2b) the one or more clusters into which a given new measurement s can be said to fall. Each cluster constitutes a category c, and is thus indicative of the respective anatomical location. Hard or soft membership may be used in the objective function F in (2b) to compute the score for the respective membership when applying the prediction algorithm.

The earlier implemented k-nearest neighbor algorithm may be implemented in a supervised fashion, each measurement specimen s' having its label c. The prediction algorithm in deployment for new measurement s is then categorized by majority voting among the s'∈S, based on D( ) and some proximity function. For example, s may be assigned the cluster $S'_j$ whose centroid $D(S'_j)$ is closest to s, or to those clusters whose centroids are within a certain neighborhood of s.

In general, in order to solve (1a-c), (2a-c), gradient based techniques may be used where a gradient of the objective function F is computed, and the parameter adjustment is based on said gradient that defines a direction in parameter space Θ∋θ. Backward propagation algorithms for neural network type models are one example and are envisaged herein in embodiments. One or more forward passes may be used to compute variables that may be used in the back-propagations. Solving (1a-c) depends on which numerical solver algorithm is used, and may give rise to an iterative updating procedure, according to which the parameters are updated in one or more iteration cycles i:=i+1 to arrive at the solution θ*. The numerical solver algorithm may be based on any one or more of the following techniques: gradient descent, stochastic gradient, conjugate gradient, Nelder-Mead expectation maximization (EM), maximum likelihood methods, or any other. An updater UP module may implement the updating procedure. In the above mentioned GMM example, an EM-type algorithm may be used as a training algorithm. Non-gradient-based approaches are not excluded herein.

Whilst the above optimizations (1a-c), (2a-c) have been formulated as minimization problems, this is not limiting herein as respective dual formulation in terms of utility functions are also envisaged herein and the optimization at (1a-c), (2a-c) is one of maximization. Also, whilst the above eq (1a-c), (2a-c) pertain to optimizations, this should not be construed as an exclusive quest for absolute and strict minima or maxima. This is indeed not necessarily envisaged herein and for most practical purposes it will be sufficient to run the iterations until the cost drops below a quality threshold E in order to consider the minimization problem (1a-c), (2a-c) solved. Also, the minima or maxima so attained within E may be local minima or maxima and these may be sufficient in some application scenarios.

As earlier mentioned, preferably in conjunction with the classification result, there is also an uncertainty result computed A by u-determiner UD to quantify the uncertainty of the computed categorization. If the uncertainty is higher than a set threshold, the currently processed shape measurement s may be indicative of a new class not yet accounted for in the current model. The uncertainty could also be presented to the user rather than automatically rejected by the system. The uncertainty values Δ ("Δ-value") may be computed by Bayesian analysis across some or all parameters of the model M, as described elsewhere. In implicit modeling for example, this new shape measurement data as identifiable by its Δ-value may be added to the existing training data set S' thus updating the model. In some embodiments, the clustering algorithm (2b) may need to be re-run to account for the newly added one or more shape measurements to define new clusters or to assign the newly one or more shape measurements to an existing cluster. In other embodiments, such an in k-NN, the training algorithm may amount to no more than adding the allegedly new specimen s (that attracted the high uncertainty value Δ) to the training set S'. In explicit modeling (1a-c), such as neural network type models, support vector machines ("SVM"), decision trees, etc., the parameters of the model may need to be re-adjusted based on the now enlarged training data set including the newly added shape measurements found during deployment.

Figure 5:
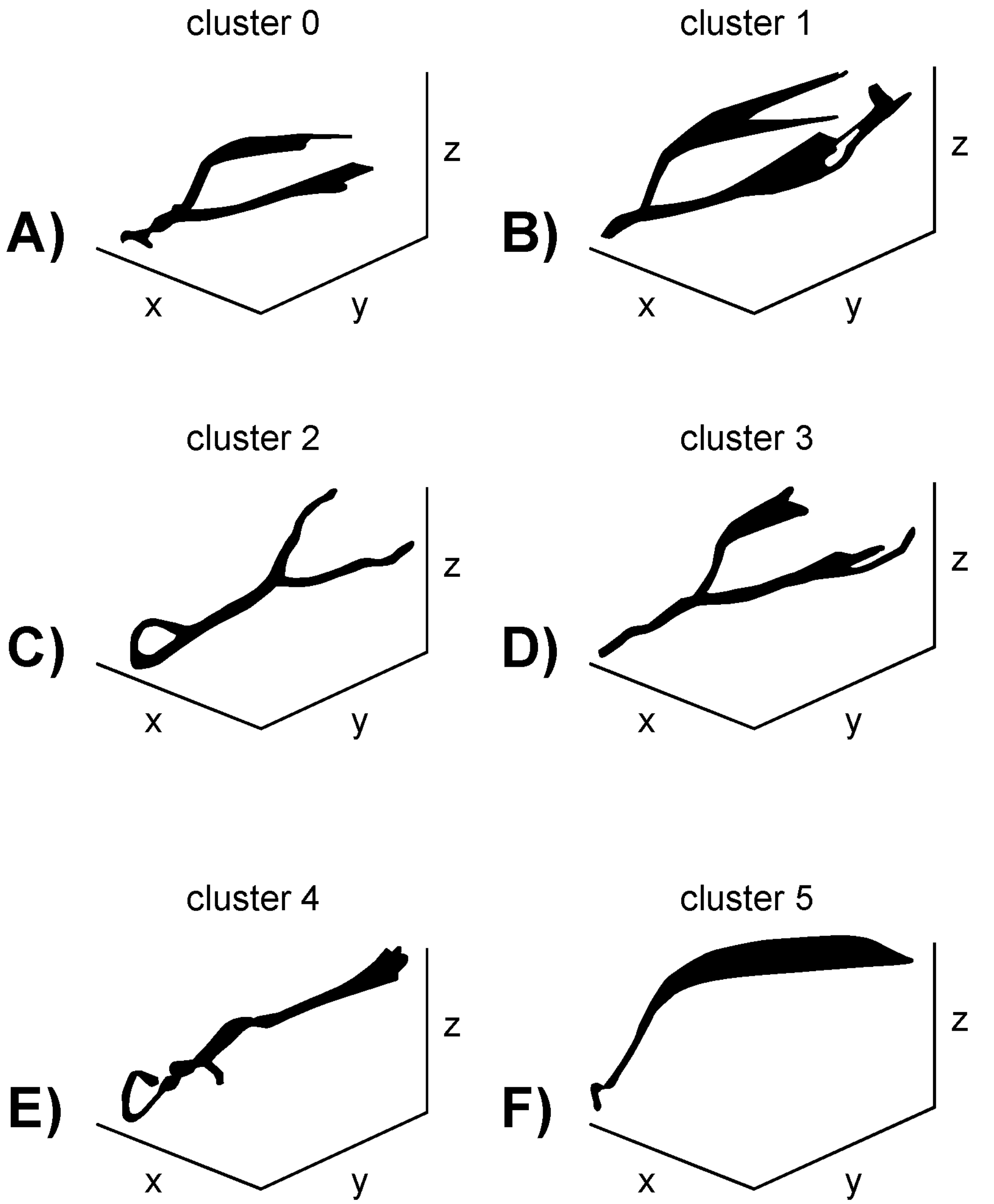
FIG. 5 illustrates exemplary shape measurements defining clusters representative of anatomical locations.

The usefulness of clustering type algorithms for the categorization of shape measurements is illustrated by the set of diagrams of FIG. 5 to which reference is now made. FIG. 5 shows exemplary shape measurement data collected from plural patients. Each shape measurement specimen for a given patient is represented in spatial domain as a 3D curve in X,Y-Z-coordinates each. Other representations in terms of curvature, axial strain etc. could have been equally used instead. As earlier indicated, instead of spatial domain representation as in FIG. 5, representation and processing in frequency domain is also envisaged herein in embodiments. Each diagram FIG. 5A-F represents measurements taken for a specific anatomical location such as for the mid-aorta in pane A. Measurements in pane B are indicative of the inferior aorta, in pane C of the aortic arch, in pane D of the superior aorta, in pane E of the side branches, and in pane F of the Iliac aorta transition. Despite the shape measurement having been taken from a number of different patients, the respective shape measurements for each anatomical location show a remarkable structural similarity which can be leveraged herein for clustering and, more generally, for any type of machine learning approach where such latent structural similarities can be successfully harnessed. The black portions in the panes A-F represent clusters or "bundles" of shape measurements s. The shape measurements are represented as 3D curves. The black portions may be interpreted as geometrical envelopes of the curves that make up each cluster.

Figure 6:
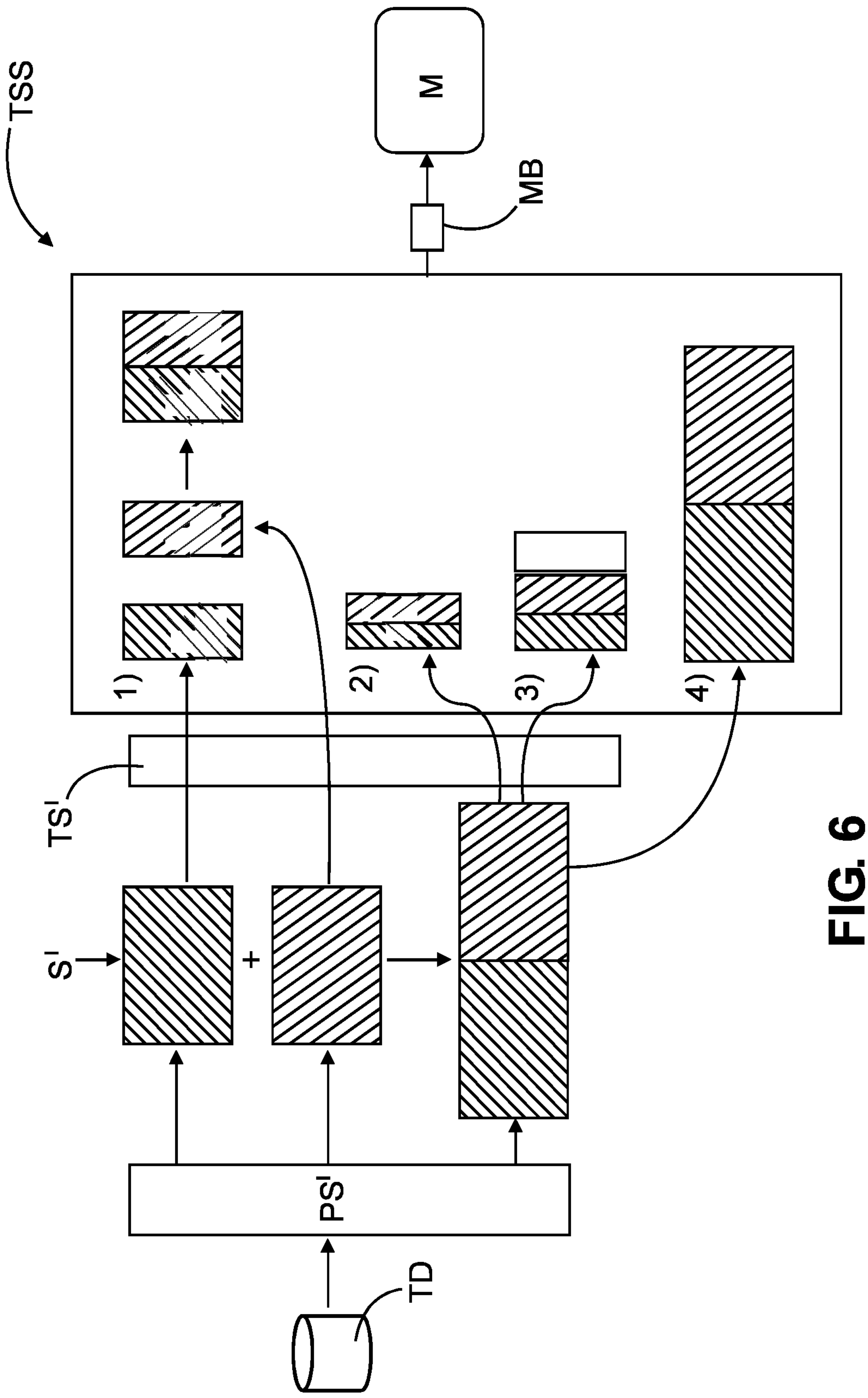
FIG. 6 shows a block diagram of a training algorithm for training a machine learning model for categorizing shape measurements.

Referring now to FIG. 6, this shows a block diagram of a training arrangement for unsupervised learning. Broadly, FIG. 6 shows an embodiment of an above-mentioned clustering type algorithm. The shape measurement data S' are illustrated in squares of different shading, one square representing spatially resolved curvature measurements the other spatially resolved strain measurement. The spatial resolution is along the length of the arm A, indexable by x. However, spatial coordinates such as in FIG. 5 may be used instead of in combination.

For computational efficiency such as to support parallel processing, the training data input s may be stored as matrices of two or higher dimensions (tensors) as schematically indicated by the said squares. The training system TSS and/or the predictor logic PL may be implemented by hardware that supports such parallelized processing such as processors of multi-core designs. This may include graphical processor units (GPU) or tensor processor units (TPU) or some such. One dimension (row or column) may include the shape measurement per increment x along arm A, and another dimension may index time t. A third dimension may index patients j. A further dimension may index contextual data κ as obtained from suitable tagging or annotation as provided by the annotator AT.

The contextual data provided by annotator AT as tags/annotations may include any event or clinically relevant patient parameter during the procedure. For e.g. blood pressure level, hemodynamics, level of sedation, need to induce cardiac pacing, etc. The annotator may obtain this from an intra procedural health record log or EMR. The contextual data may also include settings or parameters of the (interventional) imaging system, or of any one or more of the other devices Dj.

The historic or user generated shape measurements S' as held in training memory TD may be pre-processed optionally by the earlier mentioned pre-processing stage PS' for the purposes of filtering and/or normalizing the raw shape measurements. Filtering, such as smoothing or de-noising the signal may be helpful to improve the prediction accuracy of the model M. The normalization is to make the shape measurements from different patients more comparable. For example, the arm A may be used in different patients, and although a calibration may already be taken into account in the raw measurement process, small adjustments or normalizations across arms A may still be helpful for the model M. Normalization may be through statistical analysis, such as scaling by standard deviation across the set S, and/or shifting by population mean, etc.

In the notation herein we shall not distinguish between such pre-processed and raw shape measurements and will refer to each with lower s' or collectively as S', as defined before.

The shape measurements S, pre-processed or not, may be arranged in matrices such as in rows and columns, although this may not necessarily be required. The curvature and strain parts of the shape measurements may be processed separately as shown in the upper portion of FIG. 6 or may be processed in a combined manner by consolidating curvature and strain measurements into a single concatenated matrix shown in the bottom part of FIG. 6.

The shape measurements, separately or combined, are then passed through the optional transformer stage TS'. The transformation stage TS' transforms the shape measurement data S to a representation more favorable for processing. In embodiments this includes processing by a dimensional reduction algorithm. Alternatively, and in addition, such processing may include other types of processing, for instance to transforming from a sparse representation into a denser (less sparse) one. Alternatively still, or in addition, a Fourier or Wavelet transformation is used at stage TS's, if processing in frequency domain is desired.

In embodiments of dimensional reduction, principal component analysis PCA is implemented by the transformation stage TS'. Different modes of operation are envisaged herein as indicated by items 1)-4) in the large rectangle in the center part of FIG. 6. For example, the curvature and strain data matrices may be processed into principal components separately and the principal components so obtained are then combined into a single training data matrix as shown at 1).

Alternatively, as shown in 2) and 3), a concatenated matrix is formed first and is then processed by principal component analysis as a whole. The first k principal components may be retained, such as shown at 2), 3) for the case of the top 2 or top 3 principal components, respectively. k larger than 3 is also envisaged.

The so transformed training data matrices are then passed to a model builder MB that implements the training algorithm to compute the machine learning model M. In embodiments this can be done by k-means algorithm where the transformed data is partitioned into sub-sets, each representing a respective cluster, as described above at (2b) for implicit ML modelling. Descriptors D( ) for each cluster may be computed, such as respective centroids.

In alternative embodiments, the transformation stage TS' is omitted and the data is directly passed to the model builder stage MB. This is indicated in item 4) of the large rectangle.

When no transformation stage TS' is used, the respective shape measurement parts of curvature and strain may be passed separately to the model builder MB, rather than in concatenated form as shown at 4). The pre-processing stage PS', such as noise filtering or normalization may also be omitted, as processing of raw data is also envisaged herein. Whilst the pre-processing PS' and representation transformation TS' have been explained in context of the training system TSS, the same implementation is used upstream the predictor logic PL during deployment, the predictor logic implementing the predictor algorithm. Preferably, the stage(s) PS, TS are used in cooperation with the predictor logic PL if they have been used in the training system TSS. Otherwise, the stage(s) PS, TS may be omitted.

Whilst the clustering scheme as in FIG. 6 or similar is unsupervised as the clusters are not known-a-priori, the number of clusters (in general a hyperparameter K) is pre-defined and likely informed by clinical knowledge. The clustering may be computed by model builder MB using any known clustering algorithm such as Voroni-cell based tessellation algorithms (Lloyd's algorithm), the Hartigan-Wong method, or others still. The assignment between clusters and anatomical locations c↔AL may be done by a human expert, supported by a graphical rendering of the computed clusters similar to FIG. 5. Instead of the curve envelopes as in FIG. 5, the curves themselves may be displayed in clusters. The clusters may be rendered in the spatial domain on a display device DD in respective different panes or in sequence. User may use an annotation tool AT to tag the respective cluster upon visual inspection with an identifier of the anatomical location.

It has been found that the training system TSS in FIG. 6 resulted in distinct curvature, strain, and shape profiles. Using both axial strain and curvature data in the model resulted in better prediction and separation of clusters. A PCA run on the curvature matrix and strain matrix separately led to better performance than reducing the combined matrix.

Once a new shape is provided (e.g. test data, data obtained during clinical procedure), its weights along each of the PCA dimensions is computed, and a distance (or other similarity metric) between its weights and the centroids of some or all previously identified clusters is calculated. The new shape belongs to a specific cluster only if the distance is lower than a pre-defined threshold. Otherwise, a new sample may be an outlier or a part of a completely new unidentified cluster, which is communicated to the user via a dialog message on the user interface. Alternatively, shape data can be considered a mixture of multiple clusters. This is especially the case when the arm A acquires measurements whilst it is being navigated from one anatomical position to another. Definitions of the earlier mentioned transition regions may thus emerge in the acquired data. To support such cases, instead of a hard cluster membership, soft membership function can be used in the clustering function. In the literature, this is known as fuzzy clustering, or soft k-means.

K-means algorithms (with hard or soft membership function) guarantee convergence. However, k-means type algorithms do not seem to generalize well to highly imbalanced data and become computationally expensive when the dimensionality of data increases. To avoid loss of information attributed to dimensionality reduction methods, such as PCA, neural network based deep learning methods could alternatively be used. In this embodiment, we propose two deep learning methods for shape data classification: supervised and unsupervised methods. Both will now be described in more detail.

Figure 7:
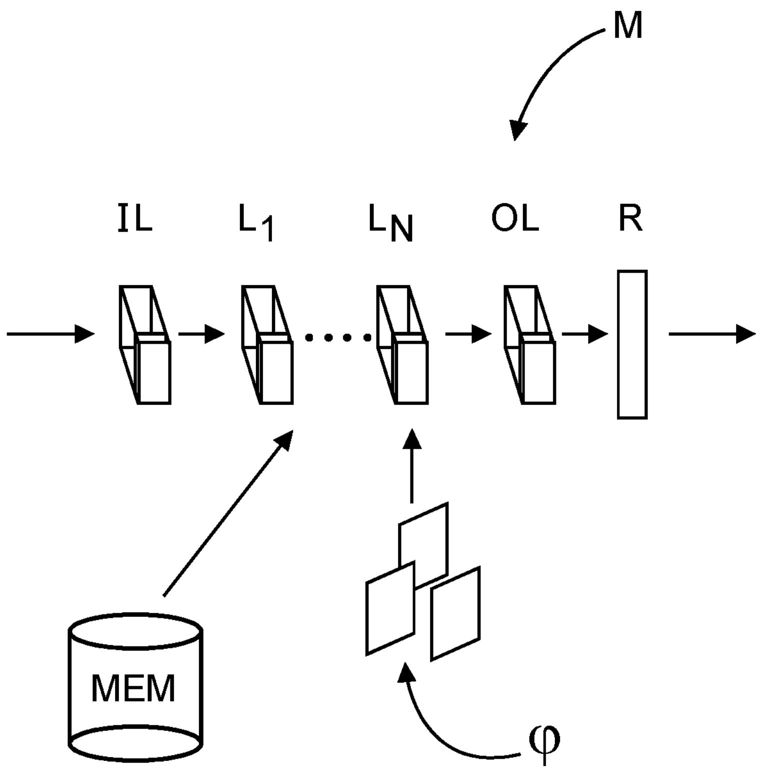
FIG. 7 shows an architecture of a neural network type machine learning mode.

Specifically, reference is now made to FIG. 7 which shows a block diagram of a neural network type model, representative of one embodiment for explicit ML modeling of the supervised learning type.

The neural network ("NN")-type architecture M may represents a multiclass single-label supervised learning classifier to classify shape measurements s into one of multiple (K) known categories cj 1≤l≤K, as mentioned above.

The classifier may be arranged in convolutional neural network ("CNN") architecture as schematically shown in the operator-diagram FIG. 8A) as network g, a special case of the more generic NN diagram of FIG. 7. Because the shape measurements are like to exhibit spatial correlation, such CNN architecture may be beneficial herein.

As any NN, a CNN comprises computational nodes (functions) arranged in cascaded layers. The layers may comprise a single or a plurality of intermediate ("hidden") layers $L_j$ in between input layer IL and output layer OL. The output layer OL may also be referred to as the task layer. Nodes in a given layer process output received from nodes in the preceding layer, to produce output for the nodes of the next layers, etc. The output of each layer is also referred to as a feature map φ. The number of layers (that is, the "depth" of the network) depends on the complexity of the data or the task (e.g. length of the shape, number of clusters, range of clinical sites, etc.). In a CNN, some or each intermediate layer comprises a convolution operation and a non-linear activation function (e.g., ReLU, Leaky ReLU, sigmoid, hyperbolic tangent, etc.) to process output of the convolution operation into feature map values. Optionally, there are, per layer, one or more additional operators including any one or more of: batch normalization, dropout, spatial pooling.

Feature map(s) generated from the last intermediate layer $L_N$ is reshaped into a low-dimensional representation. Global average pooling may be used for this reshaping. The reshaped output may be processed by a single or plural task layers OL. For present purposes, the task layer(s) is a classification layer. The classification layer may be implemented by a softmax-activation function. The output produced by the output layer OL may be presented by a classification vector, each entry of which represents the probability for the respective class, and hence anatomical category/location. Instead of using a CNN, an at least partly fully connected network may be used.

An NN or CNN-based classifier (g may be trained by training system TSS using a stochastic or mini batch training approach using single or plurality of training instances ($s'_i$, $c_i$) randomly selected from the training data set S'. This training data may represent a large patient population N (e.g., N>>100), with a reasonable coverage of different types of the medical procedures of interest (such as vascular procedures, etc.), surgical sites, anatomies, and interventional devices ID associable with the arm A, such as FORS-enabled guidewire types, etc.

To expand variation in the training data, data augmentation techniques, such as smoothing the shape data with variable window sizes, geometric deformation of data, and noise addition, can be applied.

The training data S' may be organized and processed in training as continuous data such as multi-column/multi-row shape data instances $H_i \subset s'_i$, made up of values of any one or more of: curvature, strain, twist/torsion, normalized position and/or rotation, etc. as mentioned above. For example, the values in a matrix $(a_{ij})$ may represent the curvature and/or strain values at some or each point along the arm A, as the device is navigated. One index i iterates over points along the arm A, and the other, eg j, iterates over time as the wire navigates through anatomy over time.

Optionally, contextual data κ is combined with the (purely) shape measurement data to obtain enriched data $H_i$. Such enriched data may also represented in multi-index structure such as a tensor, with additional dimension(s) to accommodate the contextual data κ. Combining may include adjoining and/or compacting the shape measurements and the contextual data into such a tensor/matrix structures. Using such multi-index structures may allow efficient processing of the shape measurements alongside the contextual data to boost learning and performance. Other manners of combining contextual data with shape measurements are also envisaged. That being said, the processing of the enriched data in training and/or deployment separately, in different data structures, is not excluded herein and envisaged in alternative embodiments. The contextual data κ may include any one or more of temperature, acquisition time, or other annotations/label assigned by annotator AT. The training data $H_i$ may be labeled by experts into several of the categories, in this case classes $c_i$. The classes serve as the target or ground truth. The above-described use of matrix or tensor representation may also be used during deployment, where the shape measurements over time are stored in such a matrix or tensor.

In some embodiments, the contextual data includes one or more earlier predictions computed in the given (current) procedure for the same patient. This can help make the training and performance more robust and reliable, as the chronological order of the previous prediction may provide further clues on the next prediction. In embodiments, it is only the immediately preceding prediction $c_{t-1}$ that is processed with the current measurement $s_t$ to compute the current category $c_t$ or, as in a recurrent neural network ("RNN"), one or more preceding measurements are processed with the current measurement to compute the current category. In a refinement of this, it is only a subset of the one or more latest prediction results that are used for computing the current prediction, namely the subset of those prediction results that correctly/reliably predicted the respective different anatomical locations. This allows excluding transition region predictions or other measurements/predictions that are unreliable or of lesser interest. The uncertainty Δ or similarity-based filtering may be used to decide which single one or more of the earlier predictions to use. Processing only one or few earlier predictions (rather than all or a large number) allows for faster low-latency processing and/or lower memory requirements.

Network g may be trained in an iterative process, in which predicted (training output) labels $\hat{c}_t$ are compared to the ground-truth labels $c_i$ using a cost function F, such as cross-entropy loss, log loss, etc. Training continues in multiple iterations until convergence is achieved, i.e., predictions match the ground-truth (within a pre-define margin), where $c_i$, $\hat{c}_t \in \{1 \ldots K\}$, and K denotes the number of classes.

Instead of using the raw measurements, the transformation stage TS', TS and the so transformed data are used instead as input to the network g. PCA may be used for example as explained above. It may be the case that the transformed features when used instead of the raw measurements, allow achieving sufficient accuracy. In such cases, lightweight model M can be trained and deployed in system parts with less compute power. For example, the number of intermediate layers may be reduced as compared to the number or intermediate layers that may be used for processing the higher dimensional batch of raw measurements. Alternatively, the transformed data TS'(S'), such as PCA features, are adjoined with the original raw measurement data for training.

It will be appreciated, that the CNN network acts itself as a dimensionality reducer, irrespective and in addition to optional upstream transformer stage TS', TS (if any). In other words, the in general high dimensional measurement input $H_i$ is transformed into a single classification vector of length K. This dimensionality reduction effect by the CNN is indicted by the turned triangle-operator symbol "“▷”" in FIG. 8A) and in the remaining FIGS. 8B)-C).

Classifiers other than of the NN/CNN-type are also envisaged herein such as any one or more of: support vector machine (SVM), decision tree (random forest), multilayer perceptron (MLP), or multivariate regression (weighted linear or logistic regression).

Figure 8:
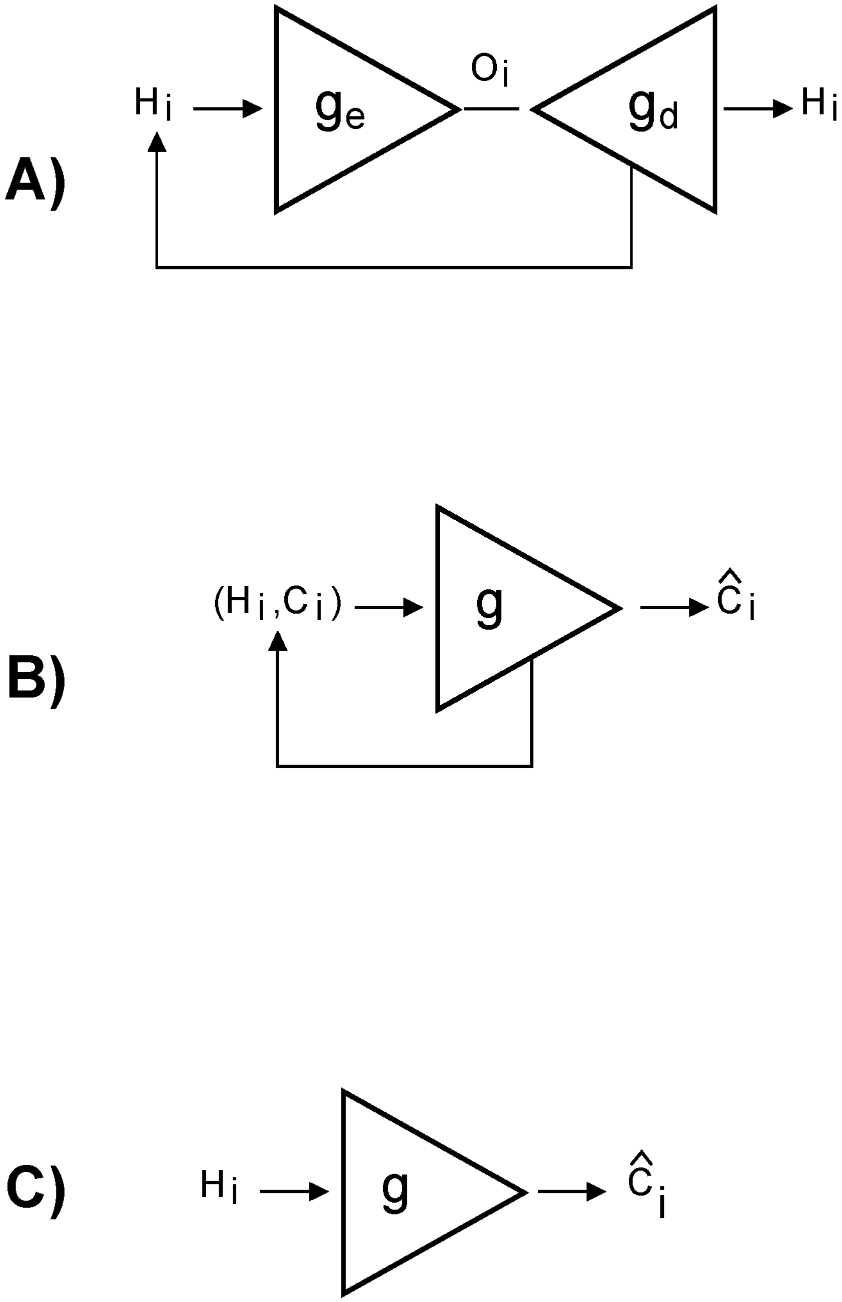
FIG. 8 shows encoder-decoder type networks as may be used in embodiments herein to learn representations of shape measurements.

More detailed reference is now made to FIG. 8A) which shows further embodiments of the transformation stage TS', TS. As per FIG. 8 embodiments, the transformation stage TS', TS may itself be implemented by machine learning. In embodiments the transformation stage TS, TS' may be implemented by certain neural network type architectures which allow learning favorable feature representation. One such class of neural networks includes auto-encoders or autoencoders of the variational type, or more generally encoder-decoder-type architectures. In General, encoder-decoder-("A/D")-type architectures are of the CNN type with a bottle neck structure as shown in FIG. 8A).

Specifically, such ("A/D")-networks are configured to reduce the dimensionality of the shape input data to a latent representation $o_i$ in the contracting path ($g_e$, encoder), and reconstruct back in the expansive path ($g_d$, decoder), from the latent representation $o_i$, the input data shape. The latent representation $o_i$ may be a vector. The ("A/D")-network, such as an autoencoder or variational autoencoder network, is trained on a preferably large dataset S' of shape data, by using any one of the training algorithms and setups describe above, except that the training algorithm is now one of regression rather than classification. A suitable distance function ||.|| for the cost function F is the squared Euclidean distance or mean squared error (L1 norm) for example and, additionally, KL-divergence in variational autoencoders that allow the network to additionally learn a distribution over the latent representations.

FIG. 8B) illustrates training of a model, such as CNN, using the representation learned by an autoencoder (as in FIG. 8A) to classify data into classes $c_i$.

FIG. 8C) is a diagram showing a trained CNN during deployment, where one or more "live" shape measurements $s \subseteq H_t$ at time t are represented in matrix or tensor form.

A dimensionality reduction algorithm, such as of the ("A/D")-type, learns to extract most relevant features, thus allowing it to reconstruct the input from the lower dimension latent representation, such neural network-based dimensionality reduction algorithms incorporate complex multidimensional data. The size of the latent representation (eg, a vector) may be pre-defined but is best chosen in view of the complexity of the shape data. During training of such an A/D-network, the size of the latent representation $o_i$ can start off small and be increased in increments during training, until the difference between the input and the reconstruction at $g_d$, evaluated on some validation data, is smaller than some threshold. The threshold may be set by the user. If the dimension of latent representation is still too large, an additional non-ML dimensionality reduction method can be applied. Typical dimensionality reduction methods known in the art are the said PCA-method, independent component analysis (ICA), t-distributed stochastic neighbor embedding (t-SNE), etc.

Alternatively, meaningful representations for the shape measurements can be learned by combining shape measurements with acquisition or prediction time as contextual data, and using the time dimension in the training. Thus, the ("A/D")-type network is trained to predict future shape measurements from earlier ones. That is, instead of learning a latent representation, $o_i$, that can reconstruct the input shape, a latent representation, $\hat{o}_i$, can be learned from shape at time t such that it can reconstruct the shape at time t+1. The encoder-decoder network can also take in shape data during time interval [t, t+n] and learn a latent representation that can reconstruct the shape data during a future time interval, [t+n+1, t+m]. It has been shown that learning more complex tasks, like predicting the future, allows the network to learn more meaningful and separable latent representations. Separable latent representations show more separation between clusters that correlate with different labels (e.g., anatomical location) when the latent representation is projected onto a lower dimension using, for example, t-SNE. More separation means less overlap between clusters, which reduces errors or ambiguities in assigning data to clusters.

The main drawback of both k-means and supervised machine learning approach as described above is that the number of clusters/classes (K) needs to be known in advance so that training data can be labelled. Alternatively, if the number of clusters is unknown or labelled and/or training data is unavailable or cannot be generated, then in this case an unsupervised feature learning method can be used. The following describes one embodiment of an unsupervised learning approach. Preferably, the above described ("A/D")-type network-based transformer stages TS, TS' are used. Broadly, a trained ("A/D")-type network-based transformer stage TS' is used to transform training set S' into a more favorable representation. Only the encoder stage $g_e$ of the trained ("A/D")-type network is used by the transformer stage TS'. The so transformed representations are then clustered by any clustering algorithm for which knowledge of K is not required. A prediction algorithm is then used in deployment that identifies the relevant cluster for a shape measurement s, based on a distance measure. In more detail, a latent representation (vector) $o_i$ given a shape data as input using a pretrained encoder network $g_e$ is extracted. The decoder network can be excluded at this stage. This is done for all, or for a predefined number of, training data specimens s'. The latent space so obtained may then be clustered. Suitable clustering algorithms that do not require a priori knowledge on the number of clusters K include any one of hierarchical clustering (agglomerative, divisive), model-based clustering (Mixture of Gaussians), or density-based spatial clustering of applications with noise (DBSCAN). The clustering definitions so obtained, including their descriptors D( ) (if any) are stored in memory MEM. Once a new shape s is provided during deployment, a distance (or other similarity metric) between the latent representation of the new sample as computed by deployment transformer TS and descriptors (such as centroids) of all previously identified clusters is calculated. The new shape s belongs to a specific cluster only if the distance is lower than a predefined threshold. Otherwise, in a dynamic learning setup, the new sample s may be an outlier, or a part of a completely new, as yet unidentified, cluster such as for a transition region. The new measurement s may be representative of the above-described transition region for example. This fact may be communicated to the user via a dialog message on the user interface. If such an outlier is detected, re-training routine is triggered, and model M is newly adapted as will be discussed below in more detail at FIG. 10 in connection with dynamic learning.

As a refinement of any of the above, it is not necessary to explicitly cluster learned representations using one of the methods specified above. For example, assuming that the unsupervised learning method is capable to learn a representation that is well separable, the problem reduces to identifying the clusters (e.g., how many, extent of each cluster, etc.) and labelling each cluster with a meaningful label (e.g., particular anatomical location). This can be achieved by one-shot or few-shots learning approaches.

In this approach, it is assumed that there is at least one labelled data. In this case, this may require as few as a single finely labelled procedure, with information about anatomical location of the device at each frame. This labelled data set, the "prototype set", is not used for training, but for identifying clusters within the learned representations. This may be implemented by an auto-labeler ALL functionality, as shown above in FIG. 3B.

In embodiments, the auto-labeler ALL is operable to interface with the transformer stage TS' to obtain the latent representation of some or each frame or interval of frames (windows) s of the labelled data of the prototype set. For example, a trained encoder $g_e$ may be used, and the auto-labeler ALL computes a distance measure between some or all frames/windows within a known label, and some or all encoder generated representations of the unlabeled training data. One suitable distance measure may be the cosine similarity, or squared Euclidean distance (L2 norm), or other.

The auto-labeler ALL then proceeds by logging the minimum of the distance measure (or maximum of a similarity measure) on a per-frame/window basis, to so compute the strongest response for some or all encodings of the training data for that particular label. The auto-labeler ALL may then cycle through some of all labels to assign to each of the training data the respective label that elicited the strongest response. Thus, the auto-labeler ALL allows propagating the labels from the prototype set to the entire training set. The number of clusters will be defined by the number of labels in the prototype set. Cluster centers can now be found, and the latent representation of any new unlabeled data can be compared to the cluster centers to assign it to a particular cluster.

Figure 9:
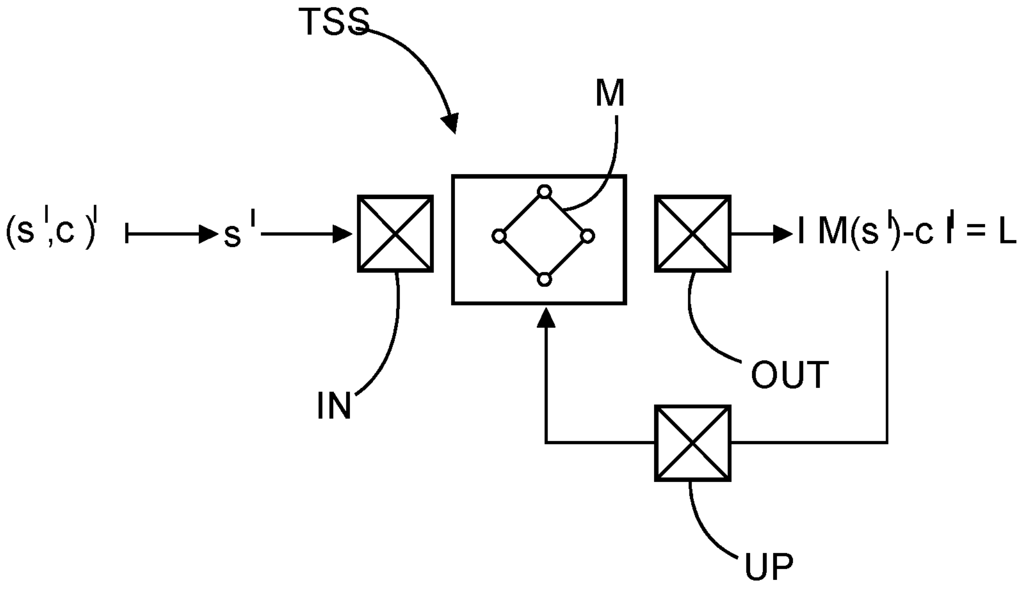
FIG. 9 shows a training system for training a machine learning model.

Reference is now made to FIG. 9 which shows a bock diagram of the training system TSS. The training system is configured to solve the applicable one of the above-mentioned learning algorithms for explicit and implicit modeling, eqs (1a-b), (2a-b). The optimization process may be guided by improving the mentioned objective function F. The function F is improved by adjusting training parameters $\theta$ of model $M^{\theta}$ in explicit modeling, or by storing and processing sets of training data as in implicit modeling, such as in clustering-type algorithms. The system TS may cooperate pre-processing PS' and/or transformation TS' stages PS of any of the above-described embodiments.

The training system may be used as a one-off or in dynamic learning repeatedly once new training data emerges. The running of the training system TSS may be triggered by user or automatically, once a sufficient number of new training data specimens $s^{+'}$ has been accumulated.

For example, in the above-described architectures for CNN-type models M or for the transformer stages TS, the training parameters may comprise weights Wand, optionally, biases for all convolutional/deconvolutional filter kernels of the CNN model. The weights may differ for each layer, and each layer may include plural convolutional operators some or each having a different set of kernels. It is in particular these weights Wj that are learned in a training phase, where index j runs over layers and convolutional operators therein. Once the training phase has concluded, the fully learned weights, together with the architecture in which the nodes are arranged, can be stored in one or more data memories and can be used for deployment. The training system TSS may be applicable for other neural network-type models, or indeed for non-neural network type M models, such as SVM, random forests, or any model of the above-mentioned type.

In explicit modeling of the supervised type, the training data comprises k pairs of data ($x_k$, $y_k$). The training data comprises for each pair k, training input data $s'_k$ and an associated target $c_k$. The training data is thus organized in pairs k in particular for supervised learning schemes as envisaged herein in embodiments. However, it should be noted that non-supervised learning schemes are not excluded herein. The $s'_k$ represents historic shape measurements s' and the $c_k$ indicates the associated category ck representative of a respective anatomical location $AL_j$.

The training input data $s'_k$ may be obtained from historical data, acquired in a Cath lab, and stored in medical repositories, e.g., in a HIS (hospital information system) for instance or patient database system, etc. The targets $c_k$ or "ground truth" may represent classification labels, in particular for classification type models M.

Such labels may be retrieved from the medical data repositories or may be assigned later by medical experts. The respective labels may be found in header data or could be inferred from inspecting the medical records and notes for the historic data. The labels $y_k$ for training a classification type model may include any indications of the respective anatomical location.

If training is to include contextual data $\kappa$, there is in general no corresponding contextual data included in the target $c_k$ for a given pair k. In other words, for learning with contextual data the pairs may in general have a form (($s'_k$ $\kappa$), $c_k$), with context data $\kappa$ only associated with the training input $s'_k$, but not with the target $c_k$.

In the training phase, an architecture of a machine learning model M, such as the shown CNN network in FIGS. 7,8 is pre-populated with initial set of weights. These can be chosen randomly. The weights $\theta$ of the model M represent a parameterization $M^{\theta}$, and it is the object of the training system TSS to optimize and hence update the parameters $\theta$ based on the training data ($s'_k$, $c_k$) pairs, to improve the objective function F as per any of eqs (1a-b), (2a-b).

For example, as per eq (1b) in explicit modeling for supervised learning, cost function F measures the aggregated residue(s), that is, the error incurred between data $M^{\theta}(s_k)$ estimated by the model, and the target as per some or all of the training data pairs k:

In supervised training of a NN-type model, the training input data $x_k$ of a training pair is propagated through the initialized network M. Specifically, the training input $s'_k$ for a k-th pair is received at an input IL, passed through the model and is then output at output OL as output training data $M^{\theta}(s')$. A suitable similarity measure ||.|| is used by the cost function, such as cross-entropy to measure a difference between $M^{\theta}(s'_k)$ produced by the model M, and the desired target $c_k$.

After one or more iterations in a first, inner, loop in which the parameters $\theta$ of the model are updated by updater UP for the current pair ($s'_k$, $c_k$), the training system TSS enters a second, an outer, loop where a next training data pair $s'_{k+1}$, $c_{k+1}$ is processed accordingly. The structure of updater UP depends on the optimization scheme used. For example, the inner loop as administered by updater UP may be implemented by one or more forward and backward passes in a forward/backpropagation algorithm. While adapting the parameters, the aggregated, for example summed, residues of all the training pairs are considered up to the current pair, to improve the objective function. The aggregated residue can be formed by configuring the objective function F as a sum of squared residues such as in eq. (1b) of some or all considered residues for each pair. Other algebraic combinations instead of sums of squares are also envisaged. Instead of proceeding per training data item as described above, batchwise training is done where iteration if over sets (batches) of training data items. As an extreme case, all training data items are considered and processed at once. Batchwise training is preferred herein.

The training system as shown in FIG. 9 can be considered for all learning schemes, in particular supervised schemes, including clustering, where the objective function F is configured to measure some objective in relation to the training partition into subsets of the training data set S', as in cluster-type algorithm, eq (2a-b). The number of clusters may or may not be known a priori.

Unsupervised learning schemes may also be envisaged herein in alternative embodiments. In unsupervised schemes, there is no ground truth data $y_k$, and the updater UP may update, in one or more iteration cycles, the objective function F. The objective function F is configured to measure some other objective in relation to the training data, such as an optimal reconstruction of the training data from a reduced dimension representation of the training data.

GPUs or TPUs may be used to implement the training system TSS.

The trained machine learning module M may be stored in one or more memories MEM or databases and can be made available as pre-trained machine learning models for use in system C-SYS. The trained model M may be made available in a cloud service. Access can either be offered free of charge or their use can be granted via license-pay or pay-per-use scheme.

Figure 10:
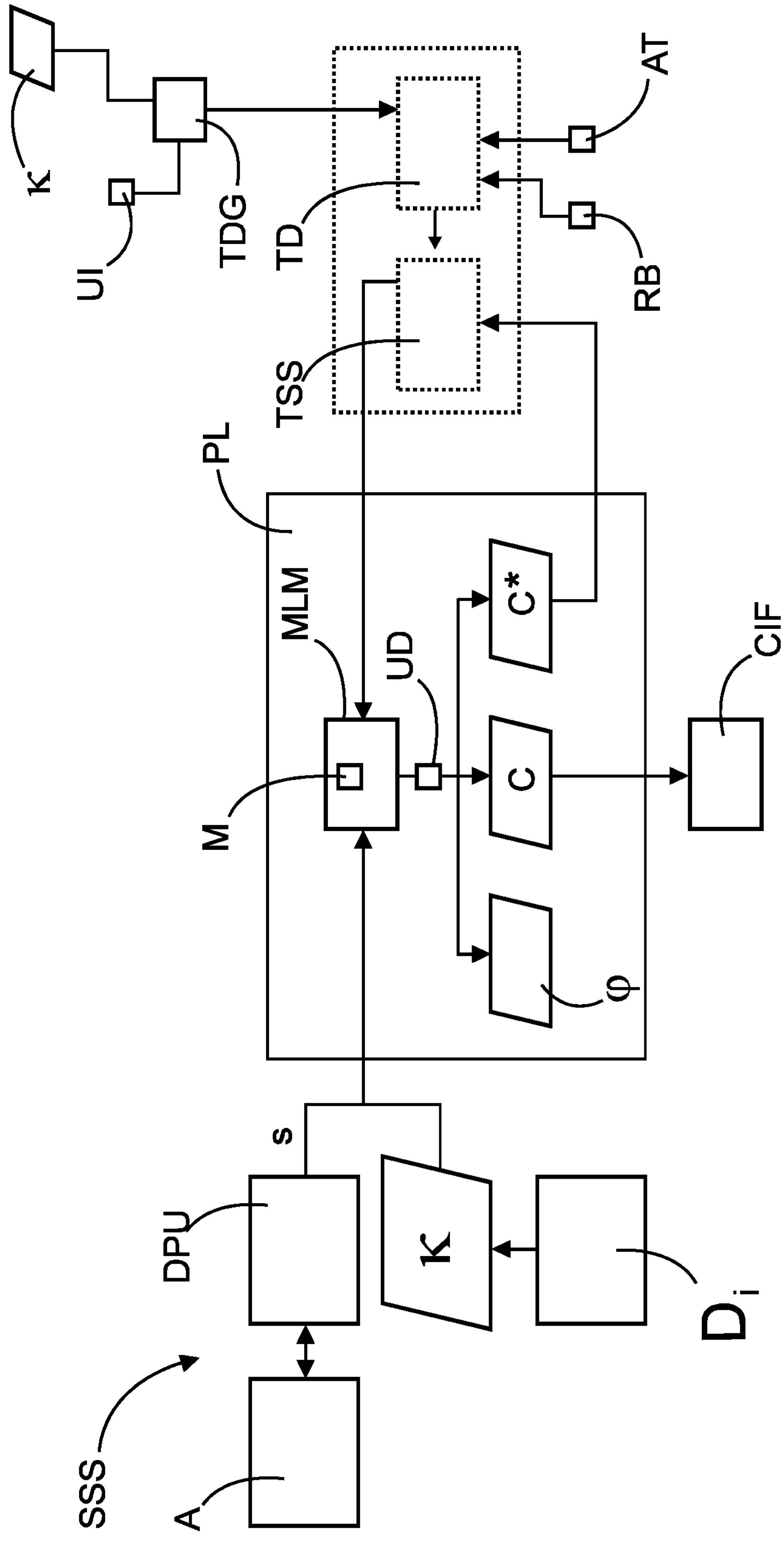
FIG. 10 illustrates an embodiment of the control system with dynamic learning capability.

Continued reference is now made to the block diagram in FIG. 10 which illustrates an operational mode of the prediction logic PL. The operational mode is one of dynamic learning. Contextual data k may be used in conjunction with the shape measurements as received from the distributing sensing system SSS. The use of such contextual data k however is optional.

As earlier explained, a given shape measurement s is processed by the machine learning module MLM. Its trained model M is applied to the shape measurement s received during deployment to compute a current categorization result c. The result c may be a classification result obtained by a classifier according to any of the above-described embodiments, or the category represents a cluster obtained in a clustering setup. The category $c_j$ is associated with a respective anatomical location $AL_j$. The predicted result c can be used to control one or more of the earlier mentioned devices/systems Dj through one or more control interfaces CIS.

It may however happen that the logic PL encounters during deployment a shape measurement $s^+$ that is representative of a new category, not previously assigned by the training system TSS. If logic PL encounters such a new specimen, this may trigger re-entering the training phase to adapt the model M in light of the new data. This repeated re-entering triggered by the quality of the received measurements s during training may be referred to herein as dynamic learning. In this way, during deployment, the current training data set S' is supplemented by data specimens $s^+$ representative of such new category. The prediction logic hence becomes more reliable and learns to better generalize over time as it encounters new data $S^+$. The re-entering into re-training in dynamic learning may be triggered on a per measurement datum base or may be triggered in batches. More particularly, in the per datum processing, for each received shape measurement, it is decided whether it constitutes a new shape measurement category $c^+$ or not. If it does, process flow passes to the training system TSS and re-training is triggered. Alternatively, instead of triggering re-training on a per datum base, a lower retraining rate may be chosen, such as re-training is only triggered once a certain number of shape measurements $s^+$ representative of new categories $c^+$ are received. In other words, shape measurements of new categories are stored in a buffer and training TS re-trains the model once a critical number has been reached which can be user set or is otherwise pre-defined.

Re-training may include re-running the training algorithm previously used to train the model but taking into account the new data. For example, in explicit modelling, parameters of the neural network type model, or of any other classifier, may be adjusted for example by re-running backpropagation training algorithm. Alternatively, if a clustering type machine learning approach was used, the training data $S'^+$ is updated to now include the new measurement $s^+$ representative of the new category $c^+$/cluster. Depending on the type of clustering algorithm used (2b), this may need to be re-run. Alternatively, such as in k-NN schemes, merely updating the training set is sufficient. In particular, the new training specimen $s^+$ may define a new category or cluster representative of a new anatomical location. When re-running the training algorithm, it may appear that some of the hitherto thought new specimens s+ do in fact fall under one or more of the previously known category and no new category may need to be opened.

The triggering of the re-training may be based on the earlier mentioned uncertainty value Δ which is computed by the u-determiner UD during deployment. As mentioned earlier, the uncertainty values Δ may be based on Bayesian analysis and may be computed by the uncertainty determiner UD based on current set of internal parameters θ* of the trained model M. However, such dedicated, supplemental uncertainty calculation may not necessarily be required. The predictions themselves may be used to quantify the uncertainty. The categorization results if provided in terms of classification are usually output as a vector with entries, each representing a respective probability for the respective class. The final classification output is usually provided as the category that attracted the highest probability. However, if none of the categories attracts a probability higher than a certain critical threshold $\Delta_0$, such as 50%, this, in itself, can be indicative of an uncertainty as the probability mass is distributed about equally across most or all of the clusters/categories. In this embodiment, the u-determiner UD acts a thresholder. Re-training is then triggered if the uncertainty so computed or ascertained in none of the class probabilities is above the critical threshold value $\Delta_0$. The critical threshold value $\Delta_0$ can be user adjusted. The uncertainty determiner UD may be a component of the prediction logic PL. The fact that a shape measurement specimen of high uncertainty has been found may be flagged by a flag Φ which can trigger issuance of a message. The message may be brought to user's attention visually, by audio signal or any other means. A similar uncertainty determination may also be done for clustering algorithms.

Another embodiment for triggering re-training in light of new data is data centered, as briefly mentioned above in connection with FIG. 8B). In this or similar approaches, a similarity measure is used to measure a distance/similarity between a given newly received shape measurement S* and already categorized, for example clustered, shape measurements in the training data base TD. Re-training is triggered if the new shape measurement S* exceeds the distance for any pre-defined cluster.

Further to the dynamically updating of the training data set S, once the procedure starts and the arm A is navigated through the anatomy, the shape data s is quasi-continuously, at a reasonable frame rate either pre-set or user triggered, processed by the logic PL. In some embodiments, such as in clustering, the predictor logic PL determines whether currently measured shape s matches a cluster in the training data set S'. The match or not is established based on a similarity metric or a certainty score eq (2c) between the current shape and the prior clusters.

Computing similarity may be facilitated by the transformer state TS' and the similarity is computed based on the so transformed data. As explained earlier, the training data s' is projected to a reduced dimensional space constructed by performing principal component analysis PCA. Principal components or modes may then be used by the training system TSS to cluster the data via K-means for example.

Since each cluster contains similar shapes, one can expect mode weights of the shapes within each cluster to be similar. A statistical similarity may be defined and used by the logic PL in addition or instead to computing the category such as cluster based on the trained model. To this end, one may assume that variance in the data within a cluster should be within $\pm c\sigma$, where σ is the variance or square root of the eigenvalue, for each mode. c is a constant that defines how much variance away from the mean is acceptable. For instance, if c=2, one accounts for 95.45% of data sampleable by the distribution associated with the cluster. If a new shape is assigned to this cluster by logic PL, but the mode weights for this shape fall outside the allowed $\pm 2\sigma$ range, this can indicate that the new shape may require a new cluster. This similarity measure, statistical or otherwise, may be used in addition to the trained model used for predicting the cluster. The similarity measure is hence another embodiment of the earlier mentioned uncertainty quantifier UD.

Further, if the new shape is dissimilar to the shapes currently held in the database and on which bases the model M was built, then reconstructing the new shape using only mode weights produced by projecting the new shape on the PCA modes will result in a poor reconstruction. A difference between the original and reconstructed shapes can also indicate the similarity or dissimilarity between a new shape and the shapes in a cluster and can be used to indicate whether a new cluster is required.

As an alternative to PCA, the transformer stage TS, TS' may be configured to use ML in its own right, such as VAEs as earlier mentioned. VAEs can also be used to learn another low dimensional representation of shape data. The drawback in PCA is that it requires point-wise correspondence between shapes to be able to successfully interpret the variance in the data. This correspondence may not always be available, e.g., when the user operates the training data generator TDG (FIG. 11) to draw a shape in-image during pre-planning. In such, or similar cases, VAEs may be used instead to automatically learn both, representative corresponding features as well as the low dimensional latent representation of the shape via the encoder $g_e$ of the VAE. The VAE may also learn a distribution over the latent space of shapes. Therefore, similarly as above, a range of acceptable variance within that distribution may be defined in order to accept or reject a new shape that is assigned to a cluster.

Further, the latent representation of a shape can be used by the decoder $g_d$ to reconstruct the new shape using only the low dimensional representation of the input shape. If the shape is not well represented by the training data, the difference between the original and reconstructed shape will be large. This difference, as above, can also be used to indicate whether a new cluster is required for the new shape. A simple thresholding of this difference may be used by the logic PL to decide whether or not to open a new category such as a cluster.

If the similarity metric is below a threshold (i.e. not similar) then either the current shape is "in between clusters", so represents a transition region, or the pre-built database TD did not capture all types of relevant shape data for the procedure at hand.

An over-frames based similarity observation may be performed to distinguish such a transition. To ensure that current shape is not in-between-clusters, shapes acquired over several frames (time points) can be expected to attract low similarity with prior clusters/categories. If the number of subsequent frames that attract low similarity is below a threshold, a decision may be made that the shape was indeed transitioning from one cluster to another. This transition-telltale-threshold may be learned retrospectively from past patient data. However, if the number of frames attracting low similarity is above a threshold, this could indicate that the shape does represent a new, as yet undefined cluster.

If such a new cluster is found, the controller C-SYS may provide an alert to the system or user. The current shape s may be saved in the database TD as a new cluster. Any new shape measurement s, acquired after the current one, that better matches this shape than any other cluster, may be added to the new cluster as a representative. The opening of a new shape cluster may be flagged to training system TSS, that a re-clustering/re-learning should be triggered. Re-training may happen intra-procedurally, or post-procedurally as required.

It is also possible that it is known before the procedure that the new patient is atypical or may have complex anatomy, thus increasing the likelihood of observing shapes that may require new clusters to be built on the fly. This information may be known from preoperative 3D imaging. In such cases, instead of forming new clusters on the fly, a different approach may be taken where shape data that is used to generate the pre-built clusters is simulated. The simulation can be performed by segmenting the vasculature that will be traversed and extracting a 3D mesh. Known mechanical properties of the devices ID to be used (e.g., thickness, flexibility, tip shape, etc.) may be fed into the training data generator to simulate the path from the access point to the target location within the 3D mesh. Simulated shapes can be saved and clustered as described above. The step of FIG. 11 may be used for this purpose. Since the data is simulated, several variations can be generated (e.g., by tweaking the parameters that control the device simulation) leading to a larger amount of data. During the procedure, shapes generated by devices in the procedure are assigned to clusters built from the simulated data, thus decreasing the likelihood for opening new clusters or categories on the fly as this may likely consume CPU resources.

As an alternative, the simulated shapes can be combined with shapes from past patient data (or the data from the patients similar to the current patient) and clusters may be formed from the combined data. In this case, some clusters may include both shapes from past patient data and simulated shapes, while some clusters (representing atypical anatomy) may only contain simulated shapes. The ratio of device shapes from the procedure that are clustered into typical clusters (with both real and simulated shapes) and shapes clustered into atypical clusters (clusters with only/mostly simulated data) may be used to quantify how atypical the patient is.

It is not only for the dynamic learning approach, but also for any one of the previously described embodiments, where it has been found useful to train the model not only on the shape measurements S, but also jointly on the earlier mentioned contextual data κ. Thus, the input for training and/or deployment is comprised of enriched measurements (s, κ). In other words, a new dimension is added to the shape measurement data as such. This enriched data (s, κ) can be represented by higher dimensional matrices and can be processed by the training system when training the model as separate channels to jointly train the model on the actual shape measurements s and the contextual data k. The contextual data may be indicative of acquisition time or of characteristics of the patient, or of any other suitable type of contextual data that describes or relates to the intervention or patient. The contextual data is encoded in numbers and may be represented as vector(s) or matrix/matrices, or tensors. The contextual data k may comprise data generated by any device $D_j$ or system used or operated in the medical procedure. The contextual data may include 2D or 3D imagery, such as X-ray imagery, of the patient. The imagery may be intra-procedural or inter-procedural. Other modalities such MRI, PET, US, etc., are also envisaged. Context data may be usefully leveraged herein to correctly categorize outlier shape measurements, that cannot be categorized into existing categories.

The context data portion κ, which may not necessarily be intrinsically numerical, may suffer from sparsity which is undesirable. Embedding algorithms based on autoencoders for example, may be used to find a denser representation and it is this denser representation of the contextual data κ which is then used when processing together with the shape measurements to train the model M.

The above-described dynamic learning is training on the fly where an existing training data set is supplemented, and the model adapted accordingly. However, the additional data may not necessarily emerge during deployment, but can be generated instead synthetically. This can happen automatically, or it can be user assisted. Generating additional training data on which the system TS may train the model is implemented by the training data generator TDG.

The training data generator TDG may include a user interface UI such as a touch screen, a pointer tool such as a stylus, mouse etc., through which the user can provide input to assist in the training data generation. Optionally, shape measurements are generated by using contextual data κ. In embodiments, the contextual data k may include pre-operative or inter-operative medical imagery in 2D or 3D. This imagery may be used to generate the synthetic measurements including their respective category such as a cluster or classification label.

Figure 11:
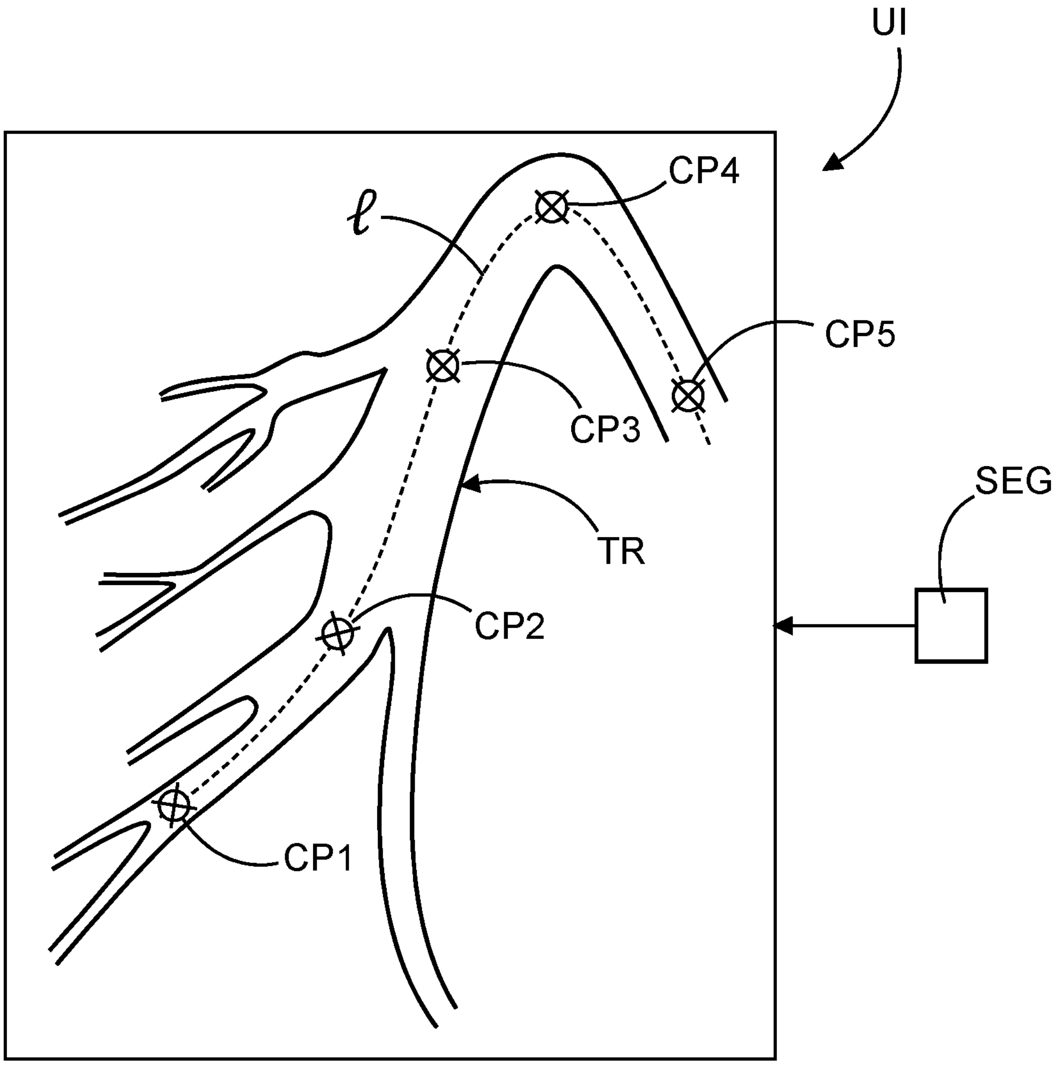
FIG. 11 shows image-based generation of synthetic training data for use in training a machine learning model.

One such user assisted example is shown in FIG. 11. Specifically, FIG. 11 shows a 2D or 3D x-ray image or an image from any other modality, such as MRI, PET etc.

For example, 3D imaging data may be reconstructed in a way to represent a particular aspect of the anatomy such as the airways or vessels. Identifying one or more target locations, such as a tumor or portion of the vessel needing repair, a 3D path can be drawn from a starting point to the target. These 3D shapes, or paths, can be extracted from the imaging data. The whole path/shape or a segment of the path/shape may then define a single shape cluster respectively. 2D projection data, such as in X-ray radiography, may be used instead of 3D image data.

In more detail, a segmentation algorithm SEG may be used to define the vessel tree VT with which the user can interact through the user interface UI. For example, the user may use a free-hand drawing tool to draw shapes into the vessel tree representing an anatomical location of interest such as a certain part of the vessel. Alternatively, a discrete number of control points CP1-5 are set by the user through the interface in the vessel tree, and a spline algorithm is used to compute a curve passing through those control points and conforming in shape with the relevant part of the segmented vessel tree. Based on the shape, curvature or strain, stress values may be computed as desired, or alternatively the 3D (X,Y,Z) or 2D (X,Y) coordinates are used to define the shape s. In order to compute the stress and or strain, material properties of the arm A to be used may be required. The shapes may be automatically generated by the segmenter SEG using centerlines of the vessel tree.

Because the so generated synthetic shape data $S^+$ are drawn by the user, who is aware of the anatomy represented by the underlying imagery, categorization is implicit. The user tool may be used to tag the drawn shape accordingly by an identifier for the respective anatomical location. In this manner, by drawing shapes in a set of imagery or in different portions thereof, a large number of categorized training data can be generated synthetically and added to an existing set of training data S'. This allows for instance topping up a poorly stocked training data base or it assists in setting up a new system at a new locality using local imagery which are likely to be representative of characteristics of the patients attending the medical facility. It may also be possible to build up an entire training data set S' from scratch, wholly comprising such artificially generated specimens.

If a clustering algorithm is used for training, the so generated artificial shapes S+ with their respective category attached can be grouped according to their categories to define clusters which can then be immediately used during deployment to assign new shape measurements to the existing clusters. A linguistic analyzer component may be used that analyzes the user generated tags for grouping into the clusters. Alternatively, the training algorithm is re-run to adjust the parameters of the neural network or other classifier model thereby accounting for the newly added synesthetic training data specimens $S^+$. The previous (old) training data already stored may be used in addition to newly generated ones to retrain the model. The generation of the synthetic shape measurements $S^+$ may not necessarily rely on user support through the user interface UI as described above in FIG. 11 but may be done fully automatically. In this embodiment, the imagery is segmented as before, and portions of the vessel tree are labelled for the anatomical locations. Spline curves are then run across the anatomies to obtain the artificial shape measurements $S^+$.

Another embodiment of generating training data may be based on biophysical modeling algorithms to define the most likely path the interventional device ID (such as a guidewire or catheter) would take, based on vessel shape and device mechanical properties. The path, from which the synthetically generated shape measurement may be generated as above, may be defined based on this prediction driven by said biophysical modeling algorithm. In addition, or instead, in embodiments past device ID data, such as provided by the shape sensing system or other tracking technology), is used to learn the most likely path taken by devices during successful navigation to the target. Variational autoencoders may be used for this ML task. Optionally, uncertainty values for each path are provided, such as standard deviation or other as obtainable by the encoder stage of the variational autoencoder.

Thus, imaging data may be used therein to define shapes/lines that can then be used to define respective clusters and their anatomical location tags/annotation. The image of the anatomy of interest may be acquired at the beginning of a procedure or during a procedure. The image may be a 2D X-ray image. With the proposed training data generator TDG. The user can "draw" lines to create his/her own clusters that are meaningful, such as a path to a target branching vessel or a point where a stent graft should be deployed for example.

Once the user draws expected shapes (e.g., left renal, etc.) on an X-ray image, these drawn shapes may be used to identify which clusters are expected to be seen during the procedure. The training data generator TDG may include a visualization component. A distribution of possible shapes from each cluster may be so displayed using the shapes that already belong to these clusters.

The new 2D or 3D shapes/paths/lines may be used to create clusters from scratch which are specific to the current patient. Alternatively, and in addition, the synthetically generated shapes could be used to create additional clusters if the existing training data set does include (yet) a fitting cluster.

Figure 12:
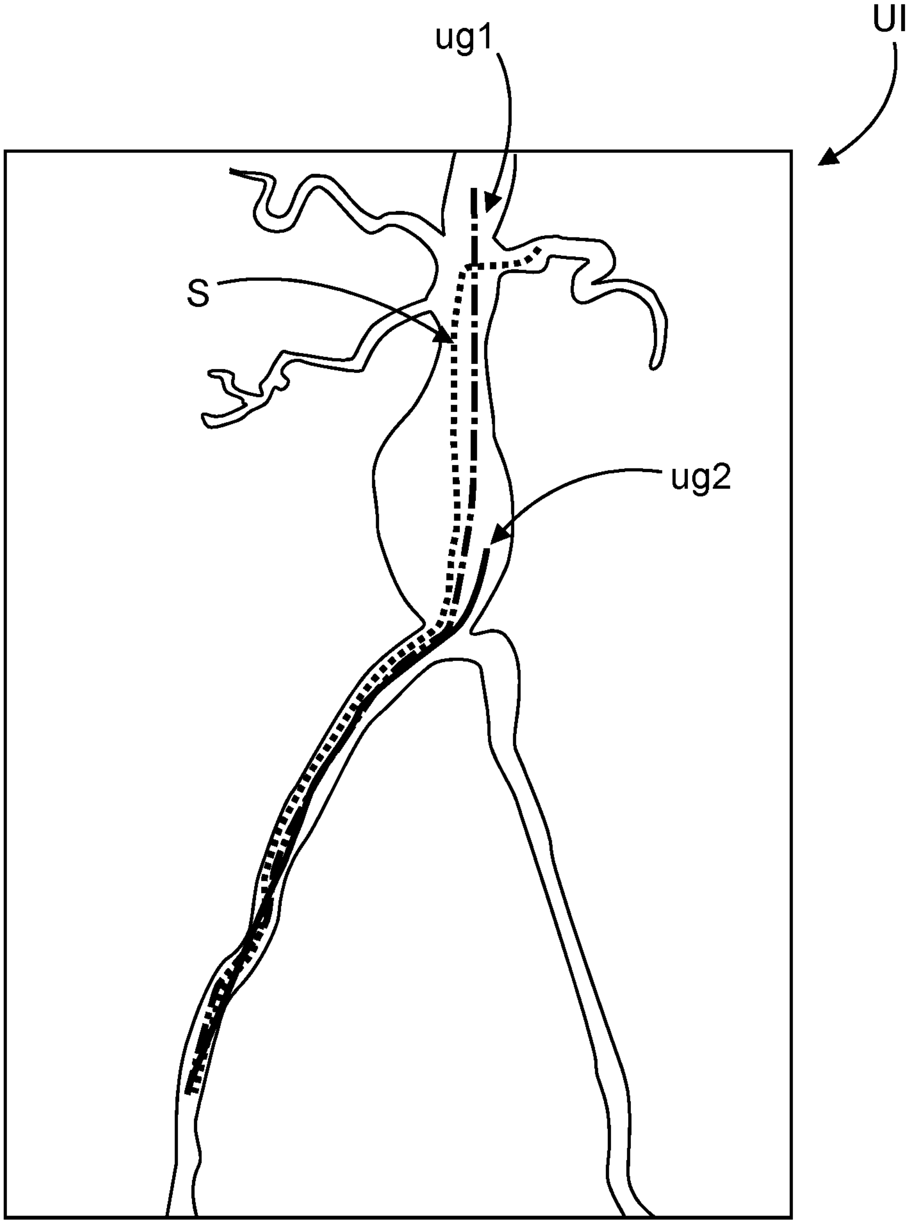
FIG. 12 shows image-based generation of training data using registration.

Another embodiment of generating training data by user assisted means is shown in FIG. 12. This embodiment uses shape measurements which are registered on occasionally required imagery during the procedure. The continuous line shows the shape measurement registered onto the structure of the current image. The user can define additional, artificially generated, shape measurement data $s^+$ as shown by the dashed and dashed-dotted lines ug1,ug2. The user may use a suitable user interface, such as computer mouse, stylus, touch screen, in conjunction with a drawing software, to generate the artificial shape measurement data $s^+$. Categorization/labeling is implicit due to the registration. For example, if the arm A is in the renal artery the user could tag the then acquired shape as a 'renal artery'. The 3D shape measurement returned by the arm A is saved along with the 'renal artery' tag defined by the user from a 2D x-ray for example.

However, such user assisted input is not necessarily required herein. Alternatively, the tags/annotations may also be obtained automatically by registering a 3D vessel atlas to 3D pre-op data. Some or each respective tagged location and shape measurement s would then be stored as a respective cluster. Optionally, natural language processing and/or shape analysis could be utilized to group similar tags/clusters from the annotations if the user or system generates too many clusters. Any of the above-mentioned embodiments for generating synthetic training data $S^+$ may be used instead of, or in conjunction with, "real" historic data. Training data augmentation techniques may be used to enhance the variability of the training data to so facilitate better training outcomes.

Shape measurement data in conjunction with image-type contextual data such as X-ray provides a way to label the categories found during learning. That is, the shape data provided by the arm A may be used to automatically find meaningful clusters or categories more generally, while the contextual image data, such as X-ray imaging data, may be used to automatically infer where, with respect to anatomy, the shape data was acquired in each of the categories. Shape measurements without contextual image data may be used to add more data to the training set S', by categorizing this data into the pre-existing categories, or by forming new clusters as mentioned earlier in dynamic learning. In this way, anatomical location labels can be assigned to shape measurements, even without ground truth from X-ray images. Furthermore, the shape data that is acquired around the time of X-ray image acquisition causes more natural variation to the shapes, and can be used herein to estimate cluster properties, such as mean, more robustly. That can help detecting the cluster correctly, for example when the respective location is visited again later in the procedure.

In order to correlate anatomical location tags with categories found by machine learning, the auto-labeler ALL may implement an image processing algorithm to produce labels for respective parts of the image. For example, if the kidneys are identified in the image by the image processing algorithm, and then the vessels that connect to the identified kidneys are found, the auto-labeler ALL assign these with the label "renal artery" as an example for an appropriate anatomical label. However, if an aneurysm is identified, then the main artery on either side of the aneurysm could be labeled "aorta", etc. The arm A may be registered with the X-ray image (i.e. in the same coordinate system as the x-ray image) to pick-up the labels from the processed image. A user interface may be provided instead, that allows the user to manually label the data.

Image-type contextual data may be used by the predictor logic PL alongside the predicted categories to determine the phase of the procedure. For example, the fact that a stent is detectable in an inter-operative x-ray image in combination with the predicted current category, may provide sufficient clues on the current phase of the procedure.

In another way, the system C-SYS may utilize the current predicted category information and any current information such as imaging parameters received from the imaging system (e.g., C-arm position, table position, or other) to facilitate the procedure. For example, the combined information may be used to determine if the current position of the c-arm will result in an optimal image of the device (no foreshortening or bad angle views) and anatomy, should the user decide to request image acquisition in this instant. The system C-SYS could then flag the user to change the imaging geometry for a better FoV before acquiring the image.

In addition or instead, the system C-SYS may use the combined information to determine if and when the arm A should be re-registered to the imaging system, such as an X-ray imager IA. For example, re-registration should preferably not be attempted while the user is deploying a stent graft as there is likely to be fair amount of motion imminent. However, if the interventional device ID/arm A is parked in the upper aorta, this fact may indicate that the device may remain stable for some time, as it is unlikely to be moved soon, and would thus present a good instant to re-register, thus improving accuracy of the registration and hence the arm's A visualization with respect to the image. The combined information may thus be harnessed herein to identify static phases of the procedure conducive to (re-)registration attempts.

Another type or component of contextual data $\kappa$, as opposed to image-type contextual data considered above, is time. It is also, or instead, time data that may be usefully harnessed herein for generating new shape measurements and/or for boosting performance during training and/or for annotation, or more accurately predict current phase or type of the medical procedure. The time component may be a time stamp that represents when the given shape measurement was acquired by the shape sensing system SSS. Thus it is understood that he predictor logic operates in a dynamic manner, in that it computes a stream or sequence of predicted categories in response to the stream of shape measurements provided by the shape sensing system SSS as its arm A is being moved during the procedure. The time component may be used by the conversion unit CV to convert the shape measurements not only into an anatomical location but alternatively or in addition to a type of medical procedure or phase of the medical procedure in which the arm A, and hence the associated device ID, is used. The time component may be the prediction time, that is, the absolute or the particular chronological order, in which the logic PL predicts a given category in response to a measured shape datum s during an on-going procedure. Thus, the time, and in particular the time point at which a given category is identified by the logic PL during the procedure may represent useful information for helping determine automatically the current phase of the procedure. This information can then be used to control any one or more of a variety of systems or sub-processes in the procedure and/or related to hospital operations.

Timing information issued by the shape sensing system SSS, imaging system IA, or any other of the systems/devices Dj may be used herein to facilitate the procedure.

In one embodiment, the timing information is used by the training system TSS in dynamic learning mode. For example, when running the clustering algorithm on a current training data set S' which utilizes the shape of the arm A, the timing information may be used to disambiguate partitioning into clusters. For example, if the training data set S' is only made up of the shape of the arm A then a clustering algorithm may categorize shapes that are similar into only one cluster (or category more generally). However, similar shapes may in fact come from different time points during the procedure and therefore may in fact represent a different stage of the procedure. Therefore, the timing information about when the shape was acquired can be used to separate the training data set S' into two or more categories (with similar shape) instead of just a single one.

For example, clusters that are based on shape of the arm A and a time stamp may be used for determining the phase of a procedure which can be used to control other systems Dj. For example, for a procedure where a stent is placed in a renal artery, a catheter must be navigated from the femoral artery, into the aorta, and then into the renal artery before deploying the stent. The clusters that are encountered during this navigation may be represented (See FIG. 5) as A) (shape aa, 0-30 minutes), B) (shape bb, 30-35 minutes), C) (shape aa, 35-45 minutes), D) (shape cc, 45-50 minutes) and E) (shape bb, 50-75 minutes), in that particular order. If A) and B) clusters have occurred then the system recognizes that cluster C) is coming next and may inform other systems Dj that the upcoming phase of the procedure is cluster C). By reaching cluster C), the imaging system may require a different imaging protocol to be set, or a hospital system may alert the nursing staff to prepare the next patient because the current procedure is nearing the end based on the phase of the procedure.

In another embodiment, using the same example above where the clusters encountered are expected in a particular order (in our example of FIG. 5, this is A), B), C), D), then E), if the procedure is taking longer than expected and the physician was in cluster a) for 45 minutes instead of up to 30 minutes, then the timing of the remaining clusters may be dynamically updated with a new time prediction. The above-described time-order based approach may be used with categories more generally, and is not confined to the clustering embodiments.

Referring to the training data generator TDG with user input, when the user draws a shape that is expected to be predicted during a given procedure, the drawn shape can be not only used to identify the cluster that is expected to come up, but also "when" in which order the drawn shape is expected to be predicted during the procedure. Thus, with time dimension added, the logic PL can use this deterministic "temporal trail" defined by the order tags assigned to the shape categories as prior knowledge when predicting categories for measured shapes in deployment. The logic PL may in addition or instead suggest categories to be predicted leading up to the drawn shape. The suggestions may be fine-tuned or updated as user draws more expected shapes.

If the categories as predicted during the procedure are not following this order, then this may be an indication that the new sequence defines a different type of procedure. This new sequence of clusters may then be saved back into the pre-defined database TD as defining the said new procedure. In this manner, the system can learn new procedures during clinical practice.

A deviation from expected category prediction order may also indicate a complication or difficulty in the procedure, which could affect procedure time or may require assistance from additional users with different qualifications.

The category prediction order and/or timing information could be used by the system C-SYS to inform the control system IS, and suggest procedure cards to use, enable a particular software (such as Vessel Navigator) or other tool, use alternative imaging protocols, or alert user to alternative approaches that could be attempted during the procedure.

The timing information may also be used by system C-SYS to distinguish different types of users. For example, novice users may take more time to complete steps than experienced users or may struggle with particular device manipulations resulting in new categories being formed or categories that are out of sequence compared to those held in the pre-defined database TD.

If the user is completing the procedure correctly and thus the categories are predicted in the expected order, but slower than expected, then the controller C-SYS may flag the current user as a "novice" user. Any subsequent prediction times, further down the line or in a next procedure, could then be extended by a novice-margin for that user.

If the "novice" user is flagged, then the sequence of clusters and/or new clusters may be saved by the controller C-SYS for review after the procedure. This may help to educate the novice user in areas where he/she may be struggling to perform the procedure correctly or optimally.

A navigation plan or visualization scheme displayed on in-lab display device DD for the user may be adapted by controller C-SYS, based on when the respective category is predicted during the procedure. For example, a renal artery view is displayed, instead of an iliac view. Thus, by taking into account prediction time, visual support schemes are live synchronized with the stream of predicted categories.

The prediction order may be used to flag φ or trigger useful event(s) in relation to the shape sensing system SSS. For example, the logic PL may trigger (or may suggest doing so) that the device ID be re-registered with the imaging system if the device is in a single cluster/category for an extended (pre-defined) period of time, as may be indicated by repeated predictions of the same category. For example, if the device ID is "parked" in the aorta and the physician is working on preparing another device, the "parked" device ID is stable and not being used which would be a suitable time to re-register to the imaging system. Occasional re-registration will ensure that the accuracy of the device ID with respect to the fluoroscopy images is good.

Alternatively, or in addition to any of the above, contextual data k may include patient demographics/bio-characteristics of the patient, such as sex, weight, age, BMI, etc.

Shape categories can be predicted to fit better to a current patient by utilizing patient demographic and/or procedural information. Using any one of age, BMI, anatomical target, or procedure type may improve the robustness and accuracy of predicted categories by filtering existing training data set S' and using information only from patients with similar patient characteristics when predicting the category. The training data set S' can thus be stratified according to patient characteristic. The system C-SYS queries from user the characteristics from the current patient, to then use only the subset of training data specimens that correspond to the patient characteristic.

For example, during training, the training system SYS may operate to perform an cross-validation (possibly n-fold, n>1) to improve the trained model's ability to generalize. on cross-validation, the training data is partitioned into groups, and the groups may then be used in different combination for training and validation. The training data is partitioned based on BMI, etc. Using the same data, the training system may thus generate not one universal model M (although this is still envisaged in some embodiments) but different models tuned to a particular type of patient.

In deployment, the logic PL obtains patient characteristics of new patient, to dynamically access and use the correct model that best corresponds to the obtained patient characteristics.

Alternatively, the system TS partitions your raw data S' based on patient characteristics. However, the model is still trained on all data, but the training may be tuned based on the data partitions which are based on patient characteristics. For a new patient who falls under certain patient characteristics, the logic PL accesses the model tuned to that patient sub-population dynamically.

Alternatively, a comparison of the 3D anatomy of the current patient can be made with prior patients. This comparison may be based on image data, such as 3D image data such as CBCT, CT or MRI. A similarity in the structure of interest for the procedure, such as vascular structures could be quantified. Models may then be chosen based on similar anatomical patterns.

In yet another embodiment, the patient characteristics can be used to "normalize" the data S. For instance, shapes from pediatric cases may be smaller but should appear similar to shapes from adult cases. Pediatric and adult cases may be used together to train the model, such as in clustering, but a respective "scaling" factor that were used to normalize each shape is taken into account. The scaling factors can then be associated with time spent in a given category (the time the logic returns predictions for the same category), as this may be different for different patient characteristics.

The Patient information/characteristics mentioned above be used in addition or instead to correct data imbalance, and/or as an extension to test for bias.

Referring back to the block diagram in FIG. 10, the fact that a current shape measurement $s^+$ of a new category has been detected can be flagged by the control logic PL issuing a corresponding flag φ. The new category alert flag φ may be used to influence the manner in which the control logic PL controls one or more of the various devices or systems $D_j$.

For example, once so flagged, the prediction logic PL may instruct the control interface CIF to issue a signal to influence or change certain imaging parameters of the imaging apparatus IA. For instance, an imaging geometry may be changed by moving the gantry GT, etc. In addition, or instead, operation/setting of the arm A itself may be changed, or operation/setting of the interventional device may be changed.

Figure 13:
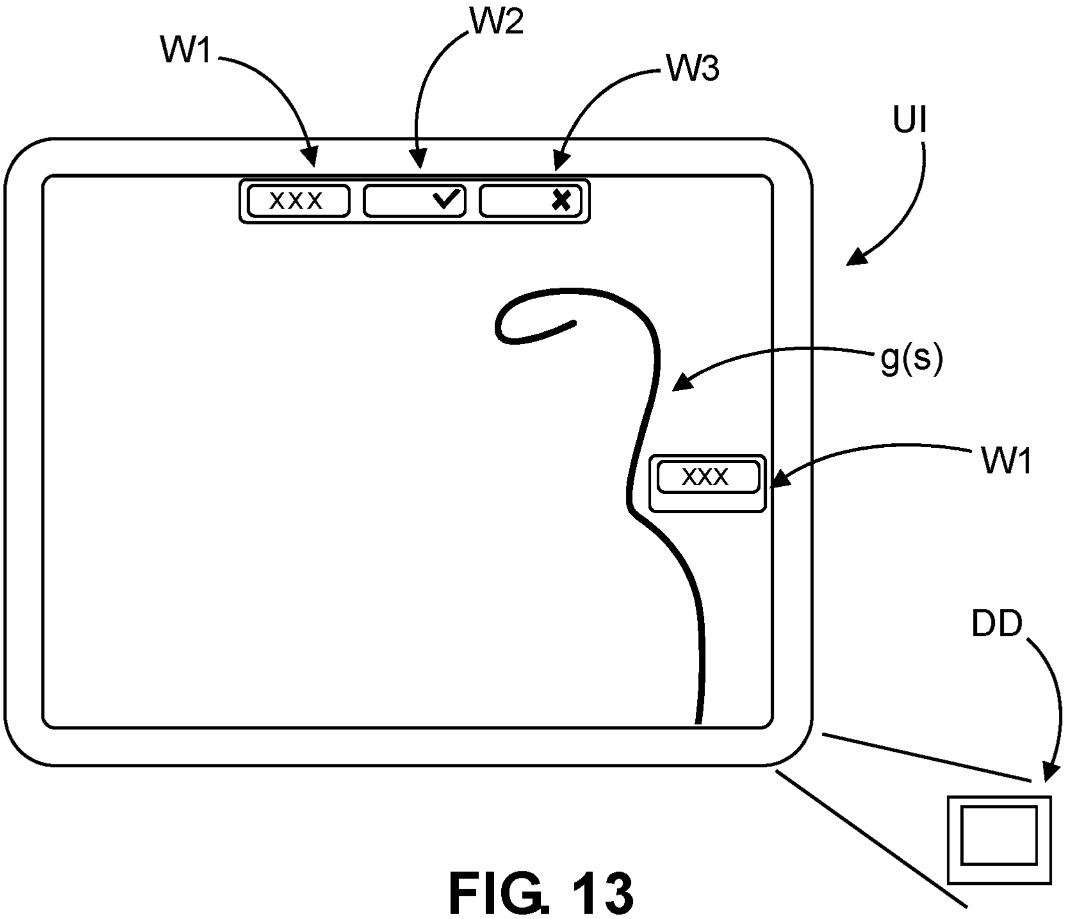
FIG. 13 shows a verification module for verifying categorizations of shape measurements.

Referring now to FIG. 13, this shows a verification module WM including a user interface UI that may be configured to allow user verifying a certain prediction category c predicted by the prediction logic PL, especially for one of high uncertainty (or equivalently of low confidence). The user interface UI is preferably but not necessarily arranged as a graphical user interface (as shown in FIG. 13) including plural graphical widgets Wj configured for human interaction.

Once such widget W1 may include an identifier for the category predicted for a received shape measurement S as collected by arm A. The shape measurement s itself may be graphically rendered by a visualization module as 3D or 2D curve for example g(s). The user can visually assess whether the proposed categorization, that is the predicted anatomical location as represented by the identifier widget, tallies with the shape g(s) as displayed on the, or on another, display device DD. Further one or more control widgets W1, W2 may be provided that allow the user to either confirm the W2 prediction or reject same. Preferably, a new identifier can be provided by the user that, in their view, would correctly represent the current location that corresponds to the current shape measurement as displayed. The correct identifier may be input via keyboard or touchscreen action into a textbox into which widget W1 changes upon reject button W3 actuation. The user may then replace the incorrect machine-proposed identifier for the anatomical location. Other input option to capture the user provided correction are also contemplated, the above being merely one embodiment of many, in terms of how this functionality may be implemented. Also, whilst touch screen interactions as shown in FIG. 13 are preferred, this is not a necessarily requirement herein, and other means of interaction include using a pointer tool such as a stylus or mouse and it is also keyboard-based interaction that is by no means excluded herein. The new identifier then either serves as label for a new category, or the measurement s is assigned to an existing category as per the training set S'. A natural language analyzer may analyze the newly provided identifier and attempt to establish a correspondence to the existing categories, if any. The need of such a natural language (NL)-processing based reconciliation may be obviated by using controlled vocabulary. The input widget for the user to provide the correct identifier may take the form of a list or drop-down menu, with proposed identifiers for the user to choose from. The proposed list may be informed by the type of medical procedure, for example the type of intervention, in the context of which the to-be-verified measurement s was taken.

The deployed system C-SYS capable of associating shape clusters with anatomical labels could display the predicted labels onscreen DD. If the user accepts the label, then the current shape is added to the labeled cluster database along with the confirmed label. If the user rejects the label and provides a correct label, then the shape is saved along with the corrected label. However, if the user rejects the label without providing the correct label, then the shape data is either discarded or set aside for labeling retrospectively. The embodiment of FIG. 11 and similar may be used along with preoperative CT or live fluoroscopy images. In such application scenarios, the predicted labels can automatically be cross checked by the module WM with anatomical labels from preoperative or intraoperative images (which may be available from automatic segmentation, etc.). If the predicted and image labels are consistently mismatched, the system may trigger a suggestion to re-compute the registration.

Often, however, the user may not confirm or reject labels. In this case, the acceptance or rejection of a label may be based on the system's confidence in the predicted label as quantified by the uncertainty determiner computing uncertainty value Δ or using a similarity measure as described above earlier. If the system has high confidence/high similarity with current categories, then the label may be added to the database without confirmation from the user. However, if confidence is low/similarity is low, then the shape data and predicted label are not added to the database TD in the absence of confirmation from the user. Below a certain confidence threshold, predicted labels are not shown to the user. As an example, the shape measurements s may be due to a current navigation through a highly tortuous iliac artery. This anatomical context may not be available to the system in the absence of imaging data. Due to a possibly unusual tortuosity of the artery, the measured shapes s may not be well represented in the labeled cluster database. However, the predictor logic PL may still infer that the arm A is in the iliac artery based on the using time context κ as described above. The logic may use the order of clusters (or steps) that the arm A/device ID went through leading up to the current, ambiguous shape measurement s. In this scenario, the confidence of the system in this label may be low. Therefore, if the user does not accept the predicted label via the verification module (e.g., by using a pop-up widget w1), the shape and label are not included in the current labeled cluster database/memory TD. The ambiguous, unassignable measurement s may be added to a separate shape database/memory or "rogue" category, and may be labeled by experts manually and retrospectively.

Figure 14:
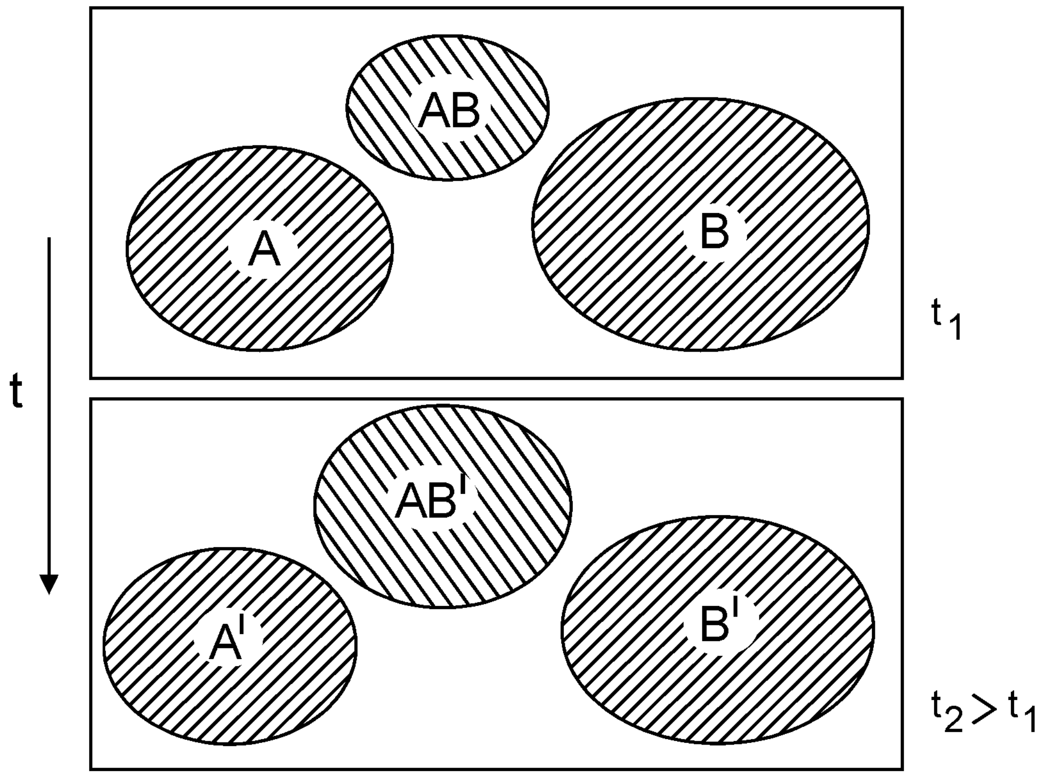
FIG. 14 illustrates operation of a rebalancer module to change sizes of clusters in training data.

Reference is now made to FIG. 14 which is an illustration of operation of the earlier mentioned re-balancer RB module. Especially in the context of dynamic learning where the training data base TD is updated by adding new data, a situation may arise, particularly for clustering-based machine learning algorithms, where clusters with different sizes are established at a certain time t1. The different size, that is the number of representatives in each cluster, is diagrammatically shown by ellipses of different sizes in the upper portion of FIG. 14. As an example, three clusters are shown designated as A, B, and AB. A situation may emerge where some of the clusters include only a small number of representatives whilst others include a large number. Such a situation may lead to inefficient operation and accuracy or consistency degradation of the predictor logic PL performance. It is desirable to have the clusters comprise a comparable number of representatives or at least to ensure that no cluster includes less than a critical number of only very few representatives as this could make performance of the predictor logic PL unstable. Operation of the re-balancer RB increases small clusters, possibly at the expense of the size of some of the large clusters. This situation is shown schematically in FIG. 14 in its lower part for a later time t2>t1, where an earlier small cluster AB has grown to become cluster AB', whilst the earlier one or more larger clusters A, B have now shrunk into smaller clusters A' and B' as they leaked some representatives into the newly enlarged cluster AB'. It is, in particular clusters built on the fly that may be imbalanced (i.e., containing very few data samples). To rebalance clusters and/or to accommodate un-clustered data, the shape data may be re-clustered (or the clustering model may be retrained). Most shapes should be reassigned to similar clusters. For instance, in FIG. 14, most data samples belonging to cluster A and B before re-clustering will still belong to clusters A' and B', respectively, after re-clustering. On the other hand, cluster AB' is now bigger than cluster AB, which was built on the fly to capture shapes that were in between clusters A and B. Cluster AB' should now include data samples that were near the tail of the data distribution in clusters A and B.

The new clusters can be assigned anatomical labels based on the labels associated with the majority (or some percentage) of data samples within those clusters. If the majority group falls below some threshold percent, then the cluster must be reviewed by an expert before an anatomical label can be assigned to it. The previous clusters may be retained until the new cluster is validated. If accuracy of the system decreases upon re-clustering, the system can revert to the old cluster. Alternatively, outlier data samples can be identified within each cluster (for example as explained above based on the similarity measure), and progressively removed from the clusters until the system performance matches or is better than with previous clusters. Alternatively, any new clusters generated from previously un-clustered data that show high contribution to error may be removed.

The illustration in FIG. 14 is not only conceptual however, as similar such graphical rendering displayed on the, or on a different display device DD for the current clustering situation are envisaged herein in embodiments. In the rendering, colors or graphical/geometrical shapes or symbols may code for cluster size, as done in FIG. 14 by using ellipses. This provides a graphical feedback for the user on the current state of the training data set S'.

Figure 15:
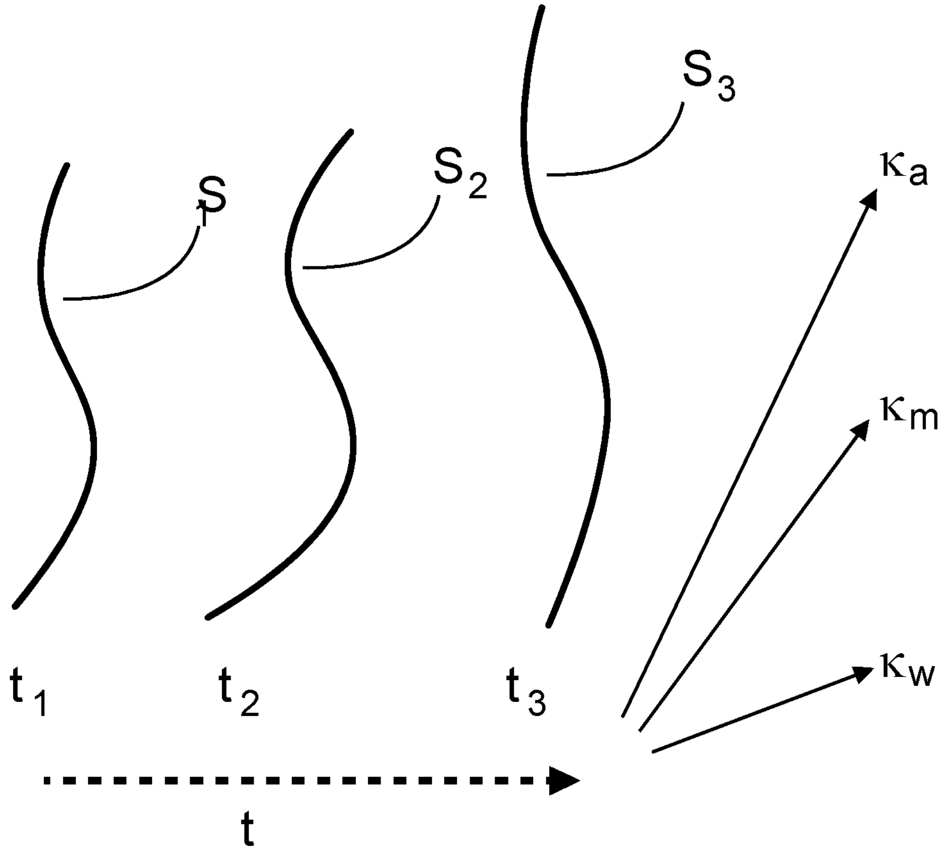
FIG. 15 illustrates evolution over time of shape measurements and their annotation with contextual data.

Reference is now made to FIG. 15 which illustrates operation of the annotator AT. In general, annotation and the related annotation tool AT is used herein to facilitate assigning tags for anatomical location to a respective category. This allows associating cluster or classification to a respective anatomical location, phase or type of medical procedure. Whilst in the above the ML models predicted categories that may be mapped to phase or to type of the medical procedure, the ML may be trained to so predict natively end-to-end, without post-convertor CV.

Broadly, the annotator is operable to annotate the shape measurement data in the training data base TD and/or newly acquired shape measurements s with tag, such as a time tag t or certain time-derived contextual data $\kappa$, such as any one or more of anatomical annotations $\kappa_a$, meta-data annotation $\kappa_m$, and/or system or workflow annotations $\kappa_w$. All three classes of those contextual annotations $\kappa_a$. $\kappa_m$, $\kappa_w$ are ultimately time derived. FIG. 15 illustrates an example of the shape data $s_j$, as it might change or deform through time, with a time axis drawn horizontally (the spatial plane parallel to the image plane).

The annotator AT may be integrated into the shape sensing/measurement system SSS and may be implemented as a time stamp that assigns a time stamp for time tagging, each time tag encoding the time at which the respective shape s(t) has been measured by arm A. Another useful tagging is the prediction time earlier discussed. The annotator may be used in deployment or in training, to annotate/tag new shape measurement data or instances of training data.

Turning now first in more detail to the anatomical annotations/context $\kappa_a$, as the procedure starts and proceeds, the chronological order of traversed anatomical context or encountered events w may be used for annotation, as mentioned earlier in connection with example cluster/category order a)-f) of FIG. 5. For example, suppose from time $t_0$ to $t_1$ the arm A entered the vascular system via an introducer. Such discrete time intervals can be used to tag and annotate clustering of 3D shape data s, time data, and 3D shape+time data within a procedure as well as between multiple procedure datasets.

Shape category evolution based on anatomical context within procedure and between procedures will be explored in more detail further below at FIG. 16, where inherent variance within a cluster may be associated with temporal characteristics.

As to_meta-data annotation $\kappa_m$, this could be used with EMR intra-procedural records to tag meta-data associated with respective steps of the procedure, such as time clusters and shape data clusters. This allows identifying or annotating critical steps during the procedure as well as help identifying adverse events. Data from intra-procedural telemetry (system and device) may be annotated with anatomical context.

Meta-data annotation $\kappa_m$ allows developing algorithms which can provide context for intra-procedural steps for patient management. For example, in procedures that target the heart (like mitral valve repair), a slowdown of heart/respiration rate may be advised if navigation in the heart is proving challenging in certain patient population.

Meta-data annotation $\kappa_m$ may further allow for association of particular clusters with known complications and other adverse effects. For instance, if the cannulation of a particular vessel is complicated, then the fact that a current shape measurement is predicted to be associated with that vessel may trigger a message alerting the user that the upcoming step may be more complex or associated with higher likelihood of adverse events. This may in turn trigger suggestions being brought to the user's attention, such as recommendation for the user to slow down tool manipulation, or suggestion that a more senior user takes over if current user was identified as novice, as explained earlier.

As to system or workflow annotations $\kappa_w$, this relates to annotating intra-procedural telemetry (system and device) data with time derived anatomical context. This can help develop predictive optimization to system parameters based on events during clustering/categorization of data. In addition, time-based event context between procedures can help create presets based on patient population.

For example, imaging geometry settings, such as C-arm settings, may be provided, based on clustering if a procedure step is proving to be complicated. The current C-arm setting may be based on the C-arm settings (or mean, or median of such settings) associated with the particular cluster/category currently predicted. A single category may also be associated with different C-arm settings. For example, different such settings may be associated with different prediction times such as the chronological order of predictions for that category. In more detail, a setting associated with a category predicted earlier, may be different from a setting associated with the same category predicted later. The system can suggest these settings as the categories are predicted over time, thus representing an evolution of categories.

The system C-SYS may provide user instructions to prepare for an upcoming category prediction at an appropriate time given a current cluster prediction. This may streamline the procedure. For instance, if the procedure remains in the current category on average 6 minutes, and a shape evolution proceeds at an average pace, an alert may be shown to take particular actions at minute 4. These actions may include preparing certain tools or imaging devices (position, dose, etc.) that may be required in the upcoming location, dimming lights in the OR, etc. However, if the shape is evolving through the current category faster than average, then the alert is shown earlier (e.g., 2 minutes before the expected end of the cluster).

Other patient or system contextual data k that may be used to create tags or annotations that further help to make shape categorizing by logic PL more robust.

In general, the predictor logic PL may take tags produced by devices Dj (other than the arm A) into account for computing the category prediction. For example, a certain device Dj, such as a contrast injector, produces a data tag which tags the shape data s with a "contrast-ON" tag. The predictor logic processes the so tagged shape data. The shape may be ambiguous so it could belong to two different categories (A or B). However, with the tag of "contrast-ON" the B cluster is assigned because contrast injection would not normally happen at the point in the procedure where cluster A can be expected to be predicted based on the a priori known chronological order of locations LAj to be traversed.

Other types of tags that may be useful for disambiguating shapes could be any one or more of: Xray-ON/OFF, CBCT-ON/OFF, amount of contrast injected, amount of medication given to patient, patient's heart rate, size of shape, patient size, etc. Often there may be correlations between these tags which can help estimate missing tags during system use. For instance, the size of the shape is correlated with the size of the patient. Therefore, when new data is assigned a category based on device shape and size of shape, the average patient size associated with that cluster can be inferred as patient size. The shape s may be transformed by transformer stage TS into the new representation, and it is features of this representation that allows association with patient size. Determination of patient size is useful for many applications (e.g., modulating keV settings for dual energy X-ray imaging, amount of contrast to inject, etc.).

Data tags produced by device Dj may also be useful post-prediction. For example, assume that the tagged data has been processed by logic PL to predict category A and assume that controller C-SYS would normally initiate a control operation in a particular way in response predicting category A. However, in this scenario a category A result and additional information about, for example, how much time the device ID has been in the said category A may produce a "Complication" or "Novice-User" tag. If one of such tags is generated, then the controller C-SYS may effect a different control operation. For example, if such a "Complication" tag issues, the predictor logic PL may instruct the system interface CIF to effect any one or more of: rotating c-arm to a new angle for better anatomical viewing, or setup contrast injector with new dose because user will need to acquire a contrast image, or provide feedback to user to select a different device. For a "Novice-User" tag, the system C-SYS may suggest imaging views or protocols that are different from what "Advanced-Users" would typically use in the given scenario.

The "Complication" tag or other tags may be used to create new clusters. For example, if a "Complication" tag is assigned and category A is predicted based on the shape measurement s and on possibly additional data from a device Dj, a new category may be defined "category A+complication" which can then be fed back into the training system TSS. Existing categories may hence be refined to form new categories. When this new category "cluster A+complication" is predicted in new procedures, the complication tag and hence type of cluster can be found faster and the appropriate control operation can be effected faster.

A "Complication" tag may be assigned based on any one or more of: amount of time spent in a cluster; amount of contrast used in a particular time period. Other conditions may apply for other devices.

Contrast injection results in a change in the axial strain as captured in the shape measurement. Contrast injection may be detected by the logic PL based on changes in measurement characteristic. It can thus be derived from the measurement data when contrast is injected, and for how long. Alternatively or additionally, the contrast injector itself may provide information about amount of contrast to the logic PL in form of data tags as described above.

Another clue that may trigger awarding a complication tag is the number of x-ray images or CBCT's acquired.

Repetitive motion may also warrant awarding such a complication tag. Respective motion of the arm A may be defined by the amount of time spent in given category, or the number of times/frequency the arm A is moved back and forth/in and out of a given anatomical location(s). This erratic motion behavior will be reflected in a corresponding sequence of oscillating category predictions.

Another indication that may trigger a complication tag award is the number of times or frequency with which axial strain at the tip of the arm A increases, as this may indicate that the tip of arm A collides with a vessel wall or implant for example.

Yet another indication that may trigger the complication tag award is the amount of medication administered to the patient, for example a drug to slow down the heart rate for structural heart repair procedures may be needed if deploying an implant is going unsuccessfully.

Figure 16:
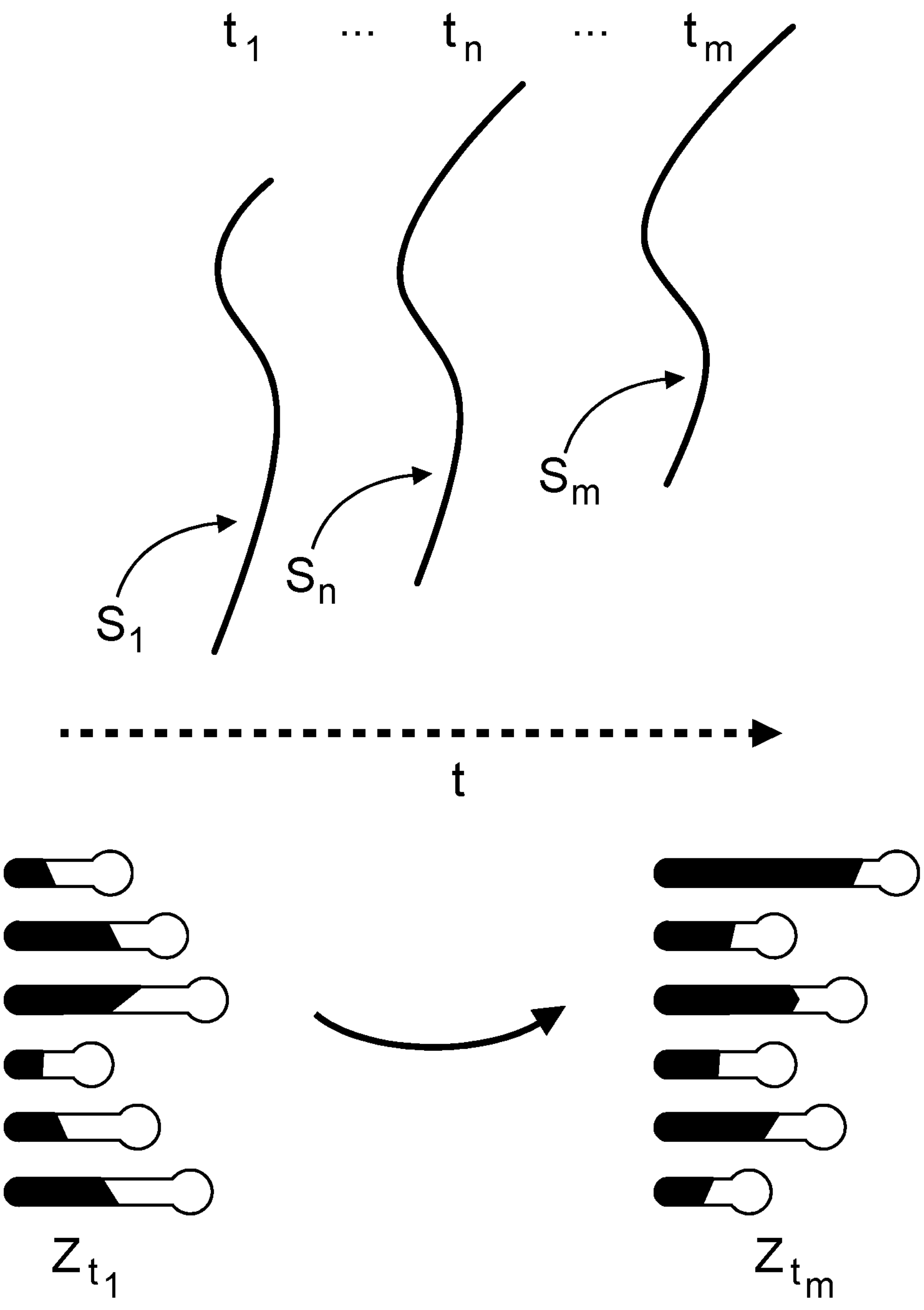
FIG. 16 shows an illustration of the evolution of representations of shape measurements over time.

FIG. 16 is an illustration of the dynamics of shape data acquired over time periods $t_1$-$t_m$ whose varying characteristics represent the earlier mentioned transition regions between anatomical locations that may give rise to new and different clusters/categories or classes, if the training data initially included only clusters of the anatomical locations of interest $LA_j$. At time $t_1$ for example there is shown a shape measurement $s_1$ acquired where the shape sensing arm A is about to enter a new anatomical location. At a later time $t_n$, the arm A measurement $s_n$ now captures the anatomical location fully, whilst at a yet later time $t_m$ tail data is generated by arm A as it keeps advancing on its path. The tail data acquired at time $t_m$ is now indictive of the departure of the arm A from the current anatomical location. The three phases as per time $t_1$, $t_m$, $t_n$ above may be thus referred to as the "shape entering a category", as "being within a category", or "leaving a category", respectively. This type of suggestive language may be used herein at times as shorthand.

The shape measurement dynamics with passage through the transition regions may be understood, for example in the context of clustering-based machine learning algorithms, by a change of clusters. Conceptually, this may be understood as a virtual movement of shape measurements in cluster space, with shape data entering a cluster at $t_1$, residing in a cluster at $t_n$, and then leaving the cluster at $t_m$.

The lower portion of FIG. 16 indicates a similar dynamic over time for the latent representations $z_{t_j}$, j: 1→m, that may be derived by operation on the shape data s of a suitable transformation stage TS, TS', such as a variational autoencoder or other as explained above.

Specifically, for time-tagged/time-stamped shape measurements data s(t), a probabilistic approach may be used by transformer stage TS, TS' to transform into a suitable representation. More particularly, in some embodiments, the encoder stage of a variational autoencoder encodes the received shape measurements into a representation in terms of parameters of probability distributions. The probability distributions represent the distribution of the shapes that may be encountered, and hence a distribution over cluster or categories more generally.

Using such a latent space representation $z_{t_j}$ obtained by the variational auto encoder embodiments of transformer stage(s) TS, TS' allows not only for a compact useful representation of the initial shape data in terms of probability distributions, but it further allows sampling from those distributions to generate an arbitrary number of synthetically generatable shapes. Indeed, such variational autoencoder-based embodiments are particularly envisaged for the training data generator TDG.

The dynamics over time of latent space representations $z_{t_j}$ may be used to distinguish novice users from expert users, and a corresponding tag may be assigned to encourage more practice.

Thus, in embodiments variational autoencoders (VAEs) of the transformer stage TS' may be used herein to learn the probability distribution over the latent representation of shapes, associations between the latent representation, z, of each shape, and the time stamp for that shape can be learned. For instance, shapes recorded prior to prediction of a given cluster ("shape entering cluster/category"), are likely to be different and are associated with different latent variables z, than shape measurements s recorded after the logic predicts the given cluster ("shape leaving the cluster/category") such shown in the lower part of FIG. 16. Such shapes can thus be said to be measured when entering the cluster, when within the cluster, and when leaving the cluster, respectively. In FIG. 16, $z_{t_1}$ shows a configuration of the latent space for a shape entering the cluster. The shaded overlay shows the range of z values produced by shapes that had entered this cluster. Similarly, $z_{t_m}$ shows this information for about to leave the cluster. The shaded region shows the distribution over the configurations of z that are associated with shapes at particular time-related states. By defining configurations of latent space representations z in this way from data with known time stamps, new data without time stamps can be automatically linked not only to the appropriate category, but also to where the device is currently located. These categories can also be broken up into subcategory. For example, if a cluster becomes sufficiently large or shows sufficient variance, the cluster may be broken up into separate clusters.

The above-described latent space-based observations may be used to provide anatomical context to subcluster data based on shape/data statistics in challenging or torturous anatomy for example.

It will be understood that the observations herein on shape dynamics in latent space Z as per FIG. 16 above is also applicable to the other ML categorizations in terms of classes for binary or multi-class classifiers, and are not unique to clustering algorithms.

The type of device Dj used during the procedure is a further source of contextual data κ. As with the inclusion of the time component during data acquisition, device type or device characteristics associated with the arm A can also be included along with shape data s. If device shapes have significant differences even when navigating the same anatomy (e.g., a very flexible device vs. a very stiff device), these shapes may result in separate categories being predicted by logic PL. The labels associated with these categories may include both anatomical context as well as the device type or some other distinguishing device characteristics. Yet another source of contextual data is EHR/medication data used during procedure.

Additionally, as explained above with respect to time, variance in shapes within a cluster can also be attributed to device characteristics. For instance, differences that may not be significant enough to generate separate/new cluster or categories more generally could still be isolated by observing differences in configurations of the latent representation, z, produced by different device types/characteristics within the same category. New data assigned to a particular category can then also be associated with device characteristics associated with the z configuration it produces. Additionally, if new data is generated in relation to a known device type, then clusters associated with other device types can be filtered out of the clustering algorithm, allowing the system to only assign to the new data clusters associated with the appropriate device type. This can reduce errors in clustering as well as in predicting which clusters to expect next. Again, the same distinction as to device type may be used for classifier ML algorithms also.

Figure 17:
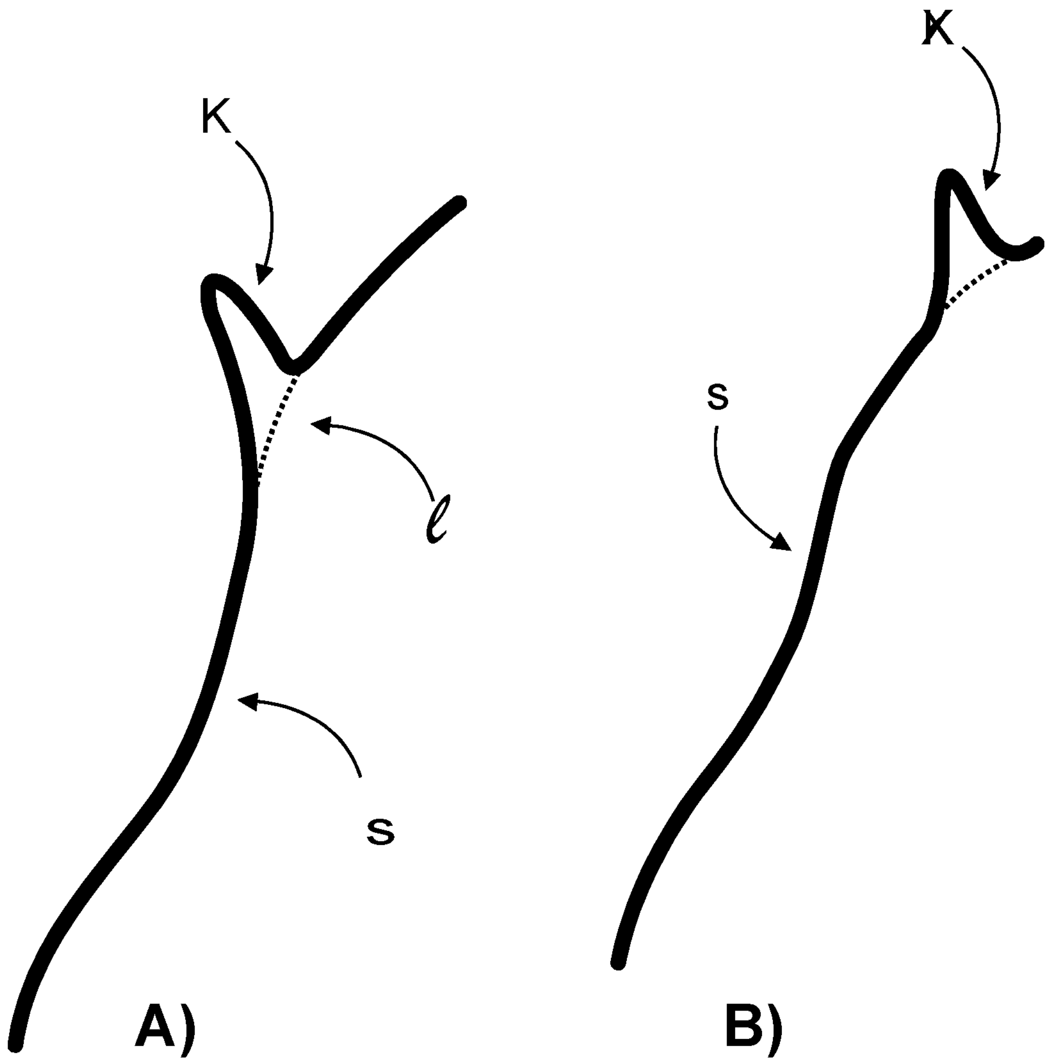
FIG. 17 illustrates shape measurements that are representative of undesirable buckling events.

Reference is now made to FIG. 17 that illustrates an operation of a sanity checker SC. Generally, the shape measurements s are generated in response to the deformable arm A dynamically attempting to conforming to the surrounding anatomy, for example whilst the user or robot advances the arm A through the anatomy such as the vessel system. The arm A is thus normally forced to assume the curvature of the vessel portions through which it is being advanced and surrounded.

However, whilst advancing the arm A, friction effects may occur that may lead to buckling of the arm A as shown in FIGS. 17A) and 17B). A kink K may emerge and cause spurious shape measurement readings which in turn may result in the predictor logic wrongly categorizing the current shape measurements. In fact, those buckling events may cause a situation where no proper categorization can occur at all and where the computed categorizations attract high uncertainty values Δ or once where the probability mass does concentrate sufficiently in any one category. The machine learning module MLL can be trained to recognize such buckling events as a particular, additional non-anatomy category.

Hence, in such embodiments, the classification or cluster does not only represent anatomical locations, procedure type or phases thereof, but may include in addition one more categories that indicate a buckling event. In some such embodiments, once a bulking event is categorized, this fact may be flagged in the system with a flag b being set. An alert message may be sent through the interface CIF to the user, such as their phone, tablet, pager, laptop computer, desktop computer or other user terminal device. Alternatively, or in addition, an alert light is energized in the operating theater/Cath Lab, a message is being displayed on the display device DD, or an alert sound is sounded out, or any other suitable sensory output is provided to alert user.

In embodiments, the sanity checker SC may be configured to attempt to correct the spurious shape reading s distorted by the buckling event K. As can be seen in FIGS. 17A) and 17B), an interpolating line l (shown in dotted style) may be cast to eliminate the kink portion. The kink portion is "cut out" and replaced by a tangential interpolating line portion as shown in FIG. 17B). By this line, local measurements for a proximal part of the arm A are connected to measurements for the distal part of arm A. The shape measurement reading so corrected/reconstructed is then re-submitted by sanity checker SC to the machine learning module MLM of logic PL, and is re-categorized to now output a better category c. This reconstructed shape could be generated from the shape measurement s alone, or based on additional information from the segmented image, such as a 3D-image (a CT image for example). The so reconstructed shape can then be tagged based on the anatomical cluster which it matches most closely.

To avoid mis-categorization due to buckling, a device shape that is detected as having buckling can be automatically tagged in a variety of ways.

Such "buckled shapes" can be tagged as "non-anatomical" shapes such that they are not saved in the clustering database. Buckled shapes can be tagged as their own cluster. If a shape is detected to relate to a buckling arm A, the system can prompt the user to accept a proposed tag or input their own tag.

Figure 18:
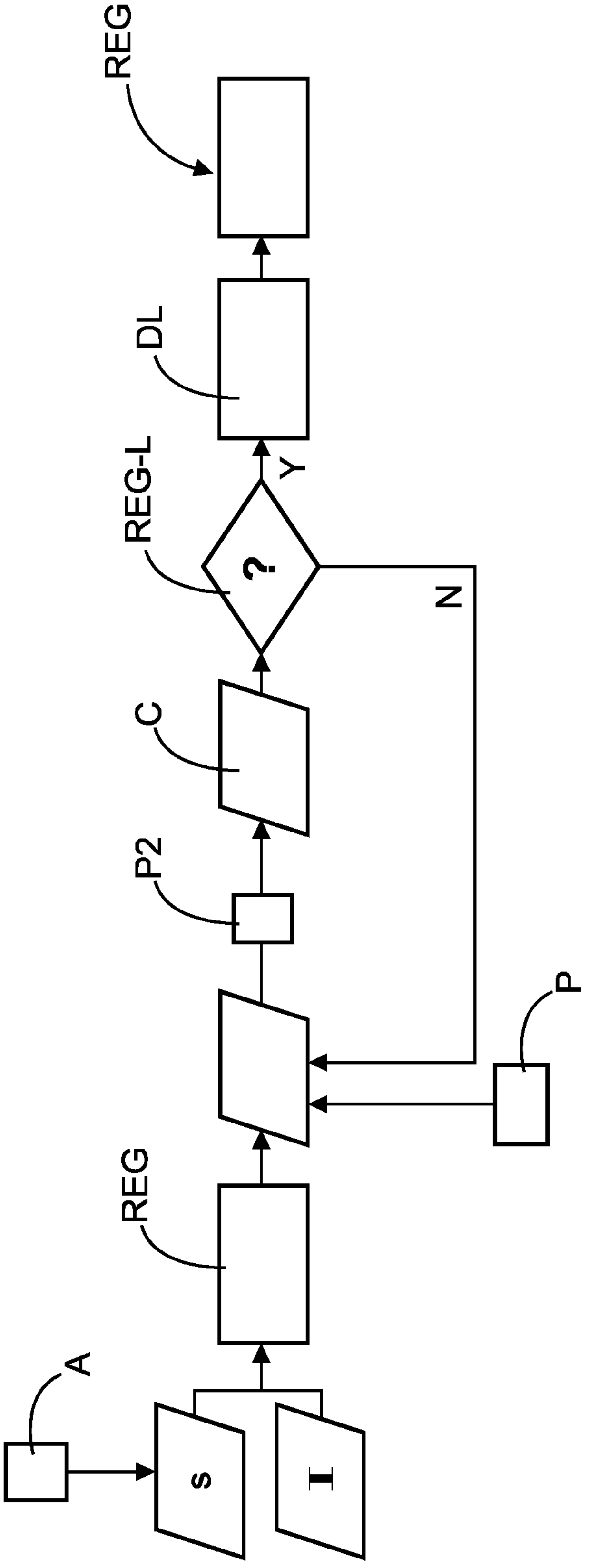
FIG. 18 shows a control operation of a registration component based on predicted categories.

Turning now in more detail to the different manners in which the control interface CIF is using the predicted categorization c and/or tags to control the various devices earlier mentioned, reference is now made to FIG. 18.

One such controllable device may include a registration module which may be run on the same computing unit as the predictor logic or may be run on a different one. The registration module may be configured to predict the time for when to perform a (next) registration, as described above.

Whilst the proposed system C-SYS may be used to replace imaging entirely, it is more preferable herein that the prediction logic PL is used alongside imaging, and imaging apparatus IA can be thus used at a reduced rate and instants where imaging may be advantageous for visualizing anatomical or device features, such as when delivering the actual therapy. The system C-SYS may thus cause fewer images be acquired during the intervention because the categorized shape measurements computed by predictor logic PL already provides sufficient indication of where in the body the arm A resides, and hence where the associated interventional device ID, is located.

The few images that are taken during the intervention may still be useful and may serve to provide additional information to the user. In such embodiments, where the prediction logic is together with the imaging apparatus, it may be desirable to occasionally register the measured shape s with the acquired image. To this end, the registration module REG runs a registration algorithm. Generally, registration algorithms establish a correspondence between respective points in two data sets, in this case a 3D curve identified in the image and the shape measurement. Elastic or rigid registration algorithms are envisaged herein in different embodiments.

With continued reference to FIG. 18, this shows a block diagram to illustrate how the registration component REG can be controlled by the computed categorizations of the logic PL. It has been observed that registration is most useful when the shape measurement does not represent a transition but is in fact indicative of the arm A residing at an anatomical location of interest. It may be a waste of computational resources to attempt registering a currently acquired image by shape measurement that represents a mere transition between anatomical locations. FIG. 18 illustrates the synchronization between registration operation and categorization result c. At a certain initial time $t_0$, shape measurements $s(t_0)$, for example in form of (X,Y,Z)-coordinates of 3D curve is captured by arm A whilst at substantially the same time, an x-ray image is acquired. The shape data and the imagery are then registered by registration module REG. The footprint of the device ID may be readily identified by a segmentation to better focus the registration.

At a later time $t>t_0$, a new shape measurement s(t) is captured by arm A. Predictor logic PL then operates on the measurement s(t) to produce a prediction of the anatomical location in terms of the category c as described above. A registration logic REG-L then checks whether the current location as per the current category is suitable for registration. The registration logic REG-L may check for example, if the category c found is indicative of transition period or anatomical location of interest. The above described time contextual data may be used for this. If the current category is not suitable for registration as it happened to represent a transition, a waiting loop is entered into. Once a next image is acquired, the registration logic REG-L rechecks whether registration is advisable at this time. If it is, that is, if the measurement is now indicative of an anatomical location of interest rather than of a transition, a synchro-delay loop is triggered and entered in, in order to ensure that the next image captured is then registered with the current shape measurement.

The delay component takes advantage of the fact that once a measurement is indicative of an anatomic location rather than of a transition region in between such locations, there is plateau event as earlier described in FIG. 2. That is, a certain number of follow-up measurements are likely to still pertain to the same anatomical location as the arm A moves slowly in increments through the anatomical location with many such measurements indicative of the same location, hence the plateau event discernable in the time vs shape measurements diagram as explained in FIG. 2*c*).

In other words, once it has been established that the measurement represents an anatomical location of interest, it is then a good strategy to wait until a next image has been acquired and to register this next image with the current shape measurement s or with the next shape measurements still likely indicative of the same anatomical location.

Other control operations based on the category as computed by predictor logic are now described for different devices or systems $D_j$.

In embodiments, it is the arm A or the shape sensing system SSS that is so controlled. For example, an automatic data saving routine may be initiated to save some shape measurements s. The shape sensing system SSS may be controlled in several possible ways using the predicted shape category c. One type of control is to enable automatic saving of certain shape measurements s. Although each frame of shape measurement s is in itself not a significantly large quantum of data, with a frame rate around 60 Hz and procedures that can take several hours, it may be a resource consuming endeavor to save all shape measurements s for entire procedures, although this may still be done if required. Instead, it is preferred herein that the shape sensing system SSS triggers to automatically save shape measurements s when moving from one category to another or when significant change in shape within a given category has been detected. Likely, data of interest worthy of memory real estate is those representing a transition region between categories, as compared to when the device is idly sitting in one place. In addition to auto-saving the shape measurements, any other procedure related data may also be saved.

Another control operation envisaged is controlling the imager IA, D2. For example, image acquisition parameters may be set in dependence on the detected category c.

Any one or more of image acquisition parameters may be set via the system controller C-SYS. These parameters for over-the-wire devices include but are not limited to frame rate, field of view, imaging depth, pullback speed, X-ray source voltage or amperage, image angle, etc. For external imaging systems, these may include but are not limited to collimation, windowing, x-ray dose, etc. For over-the-wire imaging devices like ICE, IVUS, or OCT catheters, the type of vessel the imaging device is located within, is important for setting the acquisition parameters to obtain a high-quality image. For instance, if the category prediction returns superior aorta versus renal artery, the acquisition parameters for imaging depth or frame rate may be vastly different. Here a set of predefined image acquisition parameters can be assigned to the various categories. When the category prediction is sent to the control interface CIF, the appropriate image acquisition parameters for that category are retrieved and set on the imaging system IA.

Another control option envisaged is triggering of automatic image_acquisition. For example, moving from one category to another may trigger the system controller C-SYS to automatically capture a new image or alert the physician that they have entered a new category and should acquire a new image.

IVUS catheters are capable to measure flow which is important at certain stages of a procedure. The flow imaging mode can be automatically turned on by monitoring the predicted category or sequence of categories and/or changes the IVUS catheter have undergone. For example, flow should be measured after a stent is placed. But in order to place the stent, the arm A/device ID would have gone through a particular sequence of navigation steps. These various navigation steps can be determined based on the categories that are identified throughout the procedure. After the right sequence of categories predicted, the System Controller C-SYS could then automatically turn on flow imaging.

Specific shape categories when predicted may be used to enable the system IA to change its own parameters (e.g. a PID controller, or temperature compensation method) or other.

Instead of, or in addition to, controlling an imaging device, a therapy deliver apparatus may be controlled by setting therapy delivery parameters. Such therapy delivery parameters may include any one or more of power, therapy dwell time, or others still.

Another control operation envisaged is that of changing mechanical_properties of the interventional device ID, D3. In some devices ID there is an option to change their mechanical properties (e.g., stiffness), like in some type of colonoscopes. For example, a catheter may normally be floppy but when activated it can become more rigid. In this case, the mechanical property of the device can be set or be triggered to be set by the control system C-SYS in response to the predicted category c. When the device ID is within a particular category or plural such categories, the stiffness may be reduced (set to floppy) and when in other categories the stiffness may be more rigid. This type of control may be useful for CTO crossing or maintaining a rigid rail over which an EVAR or FEVAR graft can be deployed.

Another control operation envisaged is robotic control. Robotic devices D3 are continuously being introduced into interventional procedures. If a robot is used in the procedure, any one or more of the following control options may be enabled for robotic control:

The control interface CIF may effect a change in maximum and minimum speed/applied force/curvature of the robotic device D3, based on current category, and/or transition to a new category. E.g., if a distal end of the device ID is approaching a tortuous vasculature category, then a lower maximum allowable advancement speed is requested.

The control interface CIF may effect a change force gain on haptic user interface depending on the type of vessel where the arm A currently resides as per the predicted category. For example, if the arm A is in a big vessel with little haptic feedback, the sensitivity may be set higher in the robotic system or haptic hub. The set sensitivity may be set to a lower value in smaller vessels.

The control interface CIF may effect a change in the user interface layout, such as joystick buttons, for robot control when device enters a particular category. Automatic advancement of the device between categories, which are used as way points, may be envisaged herein in some embodiments.

The control interface CIF may effect selecting automatic (robotic) navigation control schemes depending on predicted category e.g., direct steering may be used to turn into a large vessel. A more probabilistic approach for navigating into a branch with small diameter may be used, for example: advance-rotate-retract-advance, repeat until branch cannulated, etc.

Another control operation envisaged herein is storing data in a database/memory. This may be used for automatic annotation and documentation. Procedures are usually annotated and documented by user after the procedure. Predicted shape category could be used to help in automatically annotating or documenting certain aspects of the procedure, and automatically saving the appropriate data. For example, utilizing the information about the time point during a procedure and the anatomical location identified by the category, the stent placement zone could be automatically labelled. This may be done by first identifying the anatomical location, then the time point in the procedure (when the prediction occurred, in which chronology etc.), and further utilizing movement information from the guidewire or other device ID to determine which over-the-wire device was deploying a stent for example.

In another example, the number of vessel interactions is calculated in a certain region (based on category). The percentage of time spent in the procedure may be automatically documented for reporting purposes.

Another documentation envisaged is to correlate the usage of contrast with certain regions and predict potential for reaching limit in later stages of the procedure.

Control in relation to patient-specific planning is also envisaged in some embodiments. For example, in unusual cases where patient's anatomy is uncommon (e.g., from traumatic injury or prior surgery), the shape database TD can be tuned to be patient specific using that patient's pre-operative and intra-operative 3D vascular images and simulation methods as mentioned earlier above. For example, the vessels are segmented and a Monte Carlo-like simulation of "virtual" arms A traversing the patient vasculature is used to generate a possibly large number of measurements s, which are then added to the database TD to make the training data S' more patient specific.

Another control operation envisaged in controlling is providing user feedback. Ideally, users are aware of a number of factors during the procedure and change methods or approaches based on the information they are interpreting or receiving. The predicted shape category could be utilized to provide user feedback during the procedure. For example, based on the predicted category, a user message is issued, stating when the user should be cautious or could be more liberal/aggressive in their approach. More specially, if the interventional device ID is at an anatomical location or time point during the procedure where fine manipulation of the devices is critical for safety or accuracy, the user may be provided with a signal to slow down. Alternatively, when in a low risk area, the user could increase their speed of device manipulation.

As further example, based in the predicted category, the system may be able to detect if the user has the devices on the wrong side (i.e., "wrong-side surgery").

Anatomical anomalies/outliers may be detected. A portion of the population has anomalies that may not be known ahead of time, making procedures more challenging. Detecting such anomalies allows for better user guidance.

The system may automatically determine which user is using the system based on their workflow and which categories are being predicted, and in which order/sequence. Personalization parameters may be set on the system. This allows a better understanding of patient risk post-procedure or operator skill based on how long users spend in different regions (as per the predicted categories). Surgical training may be facilitated; using the predicted categories, their order and time spent in each category allows assessing how far off they are from a more experienced user. One may ascertain where category overlap is good (no more training needed) and where category overlap is bad (the trainee needs additional time or practice).

Another control operation envisaged is controlling in relation to patient monitoring. For example, based on the predicted category, alerts on blood pressure monitors may be adjusted, as to be more or less sensitive based on the device location. For example, if a catheter ID is found to be located in the heart, alarm sensitivity to changes in blood pressure may be decreased, or else the alarm may be activated too frequently. The predicted category may also be used to determine when to do baseline blood pressure measurements.

Another control operation envisaged is controlling clinical workflow. The following describe various examples of how shape category could be used to improve clinical workflow. An aspect is procedure workflow. For example, given a target that the catheter must reach, and sequence of categories predicted, a next series of one or more categories is predicted and the user is informed accordingly, for example by displaying a flow chart to show to the user what lies ahead in course of reaching the target. The user may be altered by signal or message if the specified target cannot be attained without backtracking for example.

In another example, the user is alerted once a certain point in the procedure is reached. The user may thus be informed how much time is left due to categories already covered. The user is thus informed on the phase of the procedure and optionally and automatically how much time was spent on each category. This way the next patient can be better prepared, and the medical team can be alerted for better time resourcing.

Most of the examples above utilize category information based on the shape measurements s. However, categories could also be formed based on device speed or time at certain positions, or any other reasonable parameter.

As mentioned, uncertainties A of categories may be computed. Shapes that do not fall into specific category or have high uncertainty to a category may be so flagged and could result in different settings being selected on the shape sensing system SSS, imaging system, device, etc. Two possible examples of alternative settings applied to a device or shape sensing system SSS are to lower the power on an atherectomy device if category, and hence anatomical location, is uncertain. In addition, or instead, a shape sensing system SSS diagnostic check is triggered to ensure device is not malfunctioning.

Any of the above-described category dependent control options can be used singly, in any combination or sub-combination, including using all control options.

Figure 19:
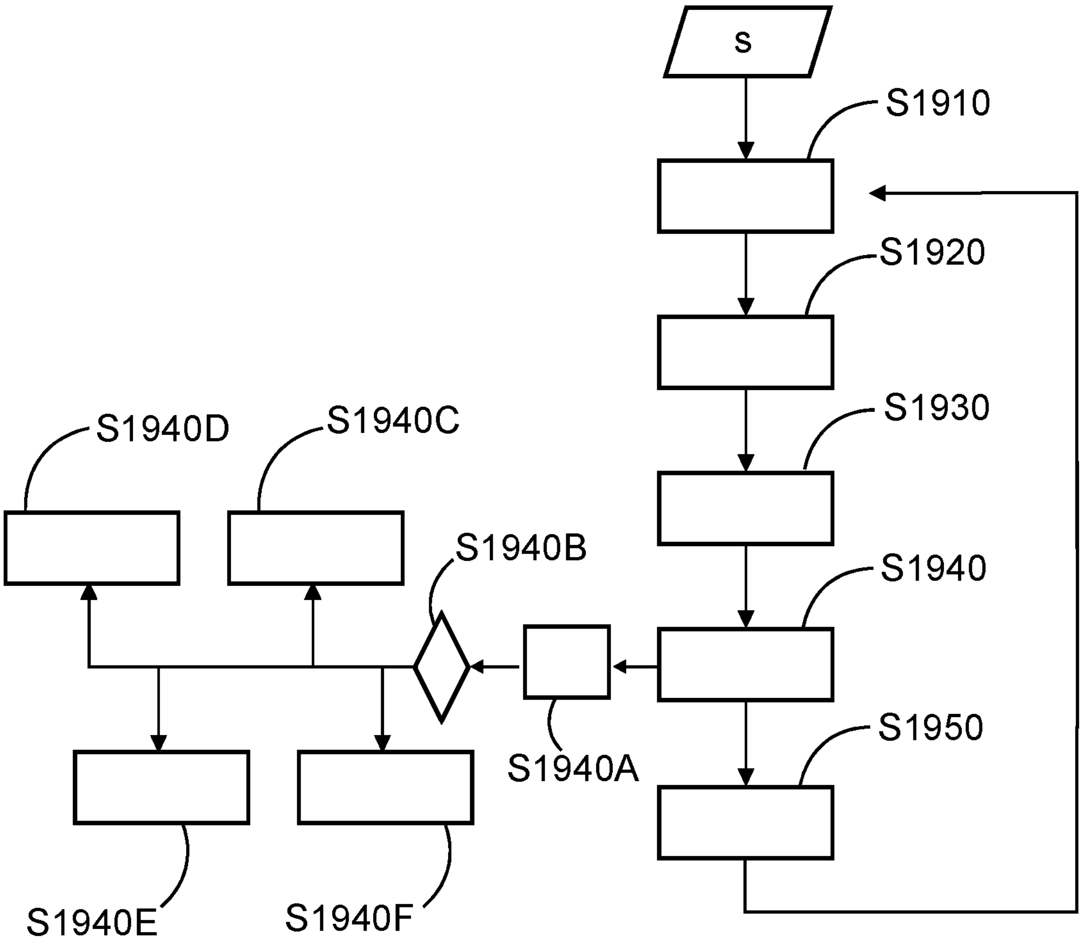
FIG. 19 shows a flow chart of a computer implemented method of controlling medical devices.
Figure 20:
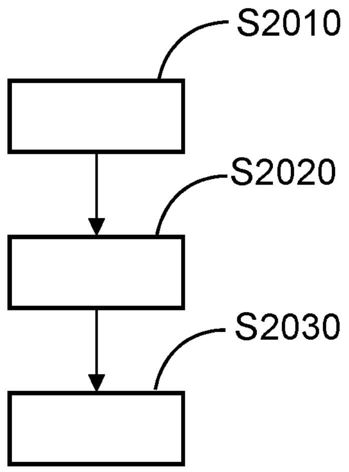
FIG. 20 shows a computer implemented method of generating training data.
Figure 21:
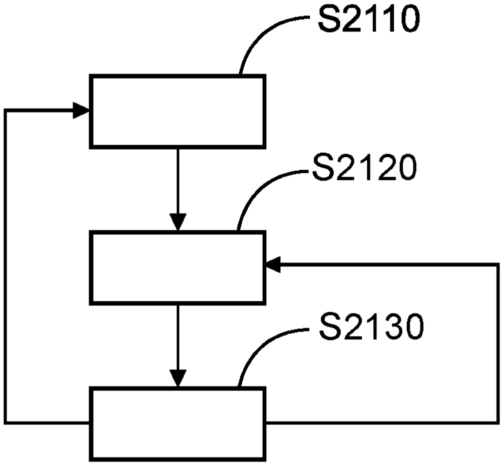
FIG. 21 shows a computer implemented of training a machine learning model.

Reference is now made to the flow charts in FIGS. 19-21. The flow charts illustrate steps of methods implementable by the above-described control system C-SYS, training system TSS and training data generator TGS. However, it will be understood that the methods to be described below are not necessarily tied to the architectures described above, and may also be understood as teachings in their own right.

Turning first to FIG. 19, this shows a flow chart of a computer-implemented method of controlling operation of one or more devices/system in a medical procedure to facilitate the procedure.

The medical procedure is performed in relation to a patient. The medical procedure may include an intervention, such as a vascular intervention where an interventional implement, tool, instrument, or device is at least partly introduced into the patient in the medical procedure.

It is envisaged herein to use shape sensing either jointly with the device so introduced, or on its own. The shape sensing system may include a deformable arm A as described above. The arm A is at least partly introduced into the patient and deforms by physical interactions with anatomies surrounding the part of the arm A so introduced. The arm A may be coupled to the interventional device ID, so both are expected to deform in the same manner. In response to such deformations or physical interaction of the arm A, the shape sensing system generates during use in the procedure shape measurement data s. The shape measurement data s has been found herein to be correlatable to shapes of the anatomical surroundings in which the device is introduced, and can thus provide an indication on the anatomical location where the device and/or the arm A current resides. As the device procedure is expected to visit certain anatomies at certain phases of the procedure, the shape measurements are also correlatable to the type of procedure or phase thereof.

Preferably, machine learning is used herein to process the shape measurements to predict the anatomical location for given shape measurement data. The procedure type or phase thereof may also be so predicted. However in the following, we will mainly focus on prediction of anatomical locations, it being understood that prediction of procedure type and phase thereof is also envisaged in embodiments, The predictions may be updated preferably in real time as the arm A is being moved inside the patient towards a target. The predictions are in the form of a category into which the shape measurement is categorized. The category may be one of a class such as in a machine learning classifier, or the category is a cluster as in clustering-based machine learning or other modeling approaches. The category is associated with a respective anatomical location of interest/procedure type or phase. Computing the category thus reveals the anatomical location of interest where the arm A currently resides, or the procedure type or procedure phase currently in.

The predicted category or indications derivable therefrom may be used to control one or more of the devices/systems used during the medical procedure.

In more detail, at step S1910 a shape measurement datum or data s acquired by a shape sensing system of the types described above in FIG. 2 is received. Any type of shape sensing is envisaged herein. The shape measurements can be acquired by the shape sensing system without use of contrast agents. Also, the shape measurements are acquired by the shape sensing system without causing or using any ionizing or other radiation harmful to the patient and/or staff operating the device ID or arm A. No imagery of any kind, optical or otherwise, causable by exposure of patient tissue to radiation is required herein for acquiring the shape measurement data. It is understood that at least apart of the shape sensing system's arm A resides partially inside the patient, and different shape measurements are generated in response to deformations by the arm A as the arm A is moved, advanced or experiences any pose change as requested by the user and/or a robot that may perform or assist in the intervention.

The shape measurement data may be visualized as 3D curves in spatial (X,Y,Z) coordinates as shown in FIG. 5, but may also be represented instead by other quantities, such stress, strain or curvature values/coordinates, preferably in 3D. 2D shape measurements are also envisaged herein.

A stream of such shape measurements may be received for different time instants at step S1910, or a single shape measurement datum is so received and processed herein.

At an optional step S1920, the raw shape measurement data is subjected to a data preparation algorithm that filters, normalizes or otherwise pre-processes the shape measurements to facilitate efficient downstream processing. Shape measurements can be reconstructed or in a raw format. A calibration matrix can be applied to shape measurements or uncalibrated shape data can be provided.

At optional step S1930, the raw shape measurement data s, or such data prepared in optional step S1920, is transformed into a more suitable representation that facilitates downstream processing, in particular reduces time and or processing requirements downstream. In particular, a dimensional reduction operation is performed in this step. A principal component analysis or any factor analytical method to transform the shape measurements into representations of lower dimension may be used in step S1930. Other types of transformation that perform other than dimension reductions are also envisaged herein, either jointly with dimension reduction or without. For example, sparsity reduction algorithms that produce more dense representations are also envisaged herein, should the shape measurement data be inflicted with sparsity. Alternatively, it may be desirable to transform into a sparser representation. The step at S1930 may include instead of any of the above or in addition, transformation into frequency domain by Fourier-type, Wavelet, or other transformational processing. Preferably FFT may be used. Step S1930 may be distinguished from pre-processing at step S1920 in that the transformation brings about in general new, more favorable representation, such as in a lower dimension or in a different space whilst such is not expected in mere pre-processing S1920. The order of steps S9130, if both are indeed applied, may be reversed.

At step S1940, a machine learning based prediction algorithm is applied to the shape measurement data s (possibly pre-processed and/or transformed as per one or both of steps S1920,S1930) to produce/predict as output the said category c that is indicative of an anatomical location where the arm A of the distributing sensing system currently resides in the patient.

Optionally, this anatomy location indicative category c may be converted into an indication for the type of medical procedure to be performed or and/or a phase of that procedure. Alternatively, the machine learning prediction algorithm is configured to provide the indication on procedure type or phase thereof, end-to-end. Because the order in which the shape measurements are acquired during time already hold clues on what the next shape measurement may indicate, it may be advantageous to feed into the prediction algorithm not only the last (current) shape measurement s, but also one or more of the previously acquired measurements as may be held in a buffer. The input during deployment in step S9140 is hence not a single shape measurement datum, but is a vector or block ($s, s_1 \ldots s_n$), that includes the latest measurement s, and the n-(n>0) (not necessarily consecutive) earlier measurements $s_j$ j=1 . . . n. This "block-wise" processing may lead to better performance.

The category c may be a classification result produced by a machine learning based classifier model, such as a neural network being one example of explicit ML modelling, Such neural network may include as an output layer a classification layer. The classification layer includes classification bins that represent in number the different types of anatomical location of interest expected to be encountered during the intervention. An additional classification bucket/class may be provided that is indicative of false readings caused by buckling of the shape sensing arm A. Instead of neural networks, other models may be used such as SVM, or others still as elsewhere described herein.

Alternatively, the machine learning algorithm used at step S1940 is one of implicit modeling, such as clustering algorithms, where the currently received shape measurement s is assigned to a pre-defined plurality of clusters where each cluster represents a different type of anatomical location, medical procedure type or phase thereof. Whichever type of machine learning algorithm is used, this may be based on training data and the model adapted or derived from such previous training data. The training data may comprise historic shape measurements previously acquired and/or may include synthetically/artificially generated shape measurement specimens. The historic shape measurements or the artificially generated ones may relate to the same patient subject to the on-going medical procedure, or may relate to one or more other patients. In clustering or other implicit modelling ML schemes, the training data itself forms part of the model.

As has been mentioned earlier, the predicting operation S1940 may be done solely on such shape measurement data.

No other data is required herein. That is not to say however that no such other data is used in all embodiments. Contextual data may be used in some embodiments together with the shape measurement data. Indeed, said contextual may still include image data for yet better robustness. The image data may comprise data representative of anatomical features, locations, phase or type or procedure. Some of the contextual data may include user input that associates the shape sensing data with an anatomical location, feature, phase or type of procedure. The user input may be provided as one or tags. Such user information may be generated as described below at FIG. 20 or in other way.

At step S1950 the computed category c is used to control a medical device. The medical device is used in the procedure. The medical device may be an imaging device, the shape sensing system itself or any of the earlier mentioned interventional instrument device ID. Step S1950 may include issuing an appropriate control signal, based on the computed category, either on the current one or in combination with one or more earlier computed categories.

Controlling of other devices/systems for supporting the intervention based on the computed category is also envisaged herein. The so controlled systems/devices may include instead of, or in addition to the foregoing, any one or more of: a clinical work-flow management system, a registration module, a vital sign measurement device, and others still. A single one of the above mentioned devices/system, a plurality of any combination of all such devices, or all such devices and beyond may be so controlled. A LUT or associative array or other mechanism may be used to map the predicted category to a desired control command which may then based used to effect the one or various control operations.

For example the device controlled at step S1950 is the imaging apparatus (IA). The control signal may be used to change an image acquisition setting, such as collimation, tube voltage/amperage, or any other as described above.

In addition or instead, the controlled device may include the display device (DD). The control signal is to causing displaying on the display device of a graphics display. The graphics display may include a graphical or textual indication any one or more of a) the predicted result, b) the current input shape measurement, c) the one or more category of the previous shape measurement data. This allows assisting the user in navigation of the interventional device/shape sensing arm A.

In addition or instead, the controlled device may include the interventional device ID itself or any other instrument used in the procedure. The control signal may be configured to adapt an operation mode of the interventional device, such as energy settings, or other settings that affect operation.

In addition of instead, the controlled system may include the shape sensing system. The control signal caused by the predicted category may be operable to adapt an operation mode of the shape sensing system (SSS), such as light intensity, sampling rate, etc.

In addition of instead, the controlled system may include a robot configured to facilitate at least a part of the procedure. The control signal is to control the said robot, for example speed of robot's end-effector that is operating the interventional device.

In addition of instead, the controlled system may include a workflow management system. The control signal is to control operation of the workflow management system, such as scheduling follow up interventions, booking of therapy or imaging sessions, etc.

In addition of instead, the controlled system may include a database or memory system. The control signal is to control whether the current input shape measurement data is to be stored for example.

At an optional step S1940A, an uncertainty value in relation to the prediction result C is computed.

Broadly, the uncertainty value measures how well the newly received measurement s at step S1910 fits or corresponds to characteristic(s) of the previous (training) data. The characteristics may include the set of current categories (class(es) or cluster(s)), if any, pre-defined for such data in an earlier training phase, prior to the current deployment phase of the ML module used in step S1940A.

This uncertainty value may be used at step S1940B to trigger other processing steps S1940C-F, depending on the magnitude of the uncertainty value. The step at S19040B may thus implement as a decision logic. In embodiments, a thresholding is issued to trigger the one or more following steps. If the uncertainty value is within a critically threshold $\Delta_0$, no steps are triggered. If the value violates the critical threshold $\Delta_0$, any one of the following processing steps S1940C-F may be triggered. Alternatively, the computing of the uncertainty value is merely for logging purposes or the Δ-value is merely displayed on a display device to the user for information purposes. The uncertainty value is thus not necessarily embedded in the said decision logic. In general, the steps S1940B-F may coordinate interaction with the training system, to trigger retraining the model and/or store new training data to build up larger training data set of shape measurements, possibly tagged with the earlier mentioned contextual data.

It should be further noted that the following additional processing steps S1940C-F may be triggered by other events, such as by receiving a user request. For example, the control operation at step S1950 may include as described above, displaying a visualization of the current measurement s in terms of a 3D or 2D curves, in response of which the user decides to trigger any of the following processing steps by using an input interface, such as a GUI or other. The earlier described verification module at FIG. 13 is one embodiment through which any one of the below processing steps S1940C-F may be triggered. Automatic triggering based on other than conditions than the magnitude of the uncertainty value are also envisaged.

Turning now in more detail to the said processing steps S1940C-F, some of these are largely an implementation of the earlier mentioned dynamic learning paradigm.

For instance, in one embodiment, at step S1940C a high uncertainty value Δ (or equivalently a low confidence value) of the prediction result c may be used as an indication for the current shape measurement being related to a hitherto unknown category of anatomic location.

In one embodiment of step S1940C, the current shape measurement s may be added to the current set of existing training data to enlarge and update same. A new category (different from the currently one or more defined categories as per the learning phase completed latest) may be opened for the current shape measurement s that attracted the high uncertainty value.

For example, the high uncertainty value may indicate that the measurement s may relate to a transition region $T_i$ where the arm A is deemed to currently reside, in between two known anatomical locations $AL_j$, $AL_{j+k}$, k≥1, the index k relating to an index for the order in which the arm A is expected to traverse the anatomical locations in a given procedure. If there is merely one known anatomical location, or the anatomical location is the first or last such location on the arm A's path, the transition region may relate to a location of the arm A before reaching the known single or first anatomical location, or to a location beyond the single or last such location, passed by the arm A on its passage. "Known anatomical location" as used herein means that there is already a category for this location, previously defined in the training phase.

If the ML setup used is one of clustering, the current measurement is recorded as a representative of this new category. If the ML setup is one of classification and the prediction algorithm is based on a classifier model, then the current measurement that attracted the high uncertainty is labelled with a new label. The model may then be retrained once a sufficient number of shape measurements for this new category have been recorded.

Because the order in which the anatomical locations are to be traversed for a given procedure is known, the transition region for the two neighboring anatomical locations is well defined and can be automatically established and included into the label or cluster semantics.

In general, the exact semantics of the newly opened category at S9140C may be defined by the user. To this end, the method may further include an additional step S1940D in which a tag or annotation is received. The tag may be assigned by the user using a suitable user interface, such as GUI. The annotation or tag is assigned to the current shape measurement. The tag value may be representative of any one of an acquisition time or any other contextual data as described above. The tag may indicate the semantics for the newly opened category. The tag may include an identifier of the new anatomical location or transition region, or may otherwise specify the semantics or purpose of the new category. It may also be possible for the user to assign at least initially a mere generic placeholder tag such as string "NEW CAT_k" or similar, with "k" a counter index. The user may then revisit the newly opened category once more representatives have accumulated under this category during the current or follow up medical procedures. The user may then be in a better position to award a more aptly named tag for this (now no longer new) category.

At step S1940E an ML training algorithm is re-run to retrain the machine learning module as used in step S1940A, but now based on this enlarged training data set with the current measurement(s) having been added at step S1940C.

For example, in clustering type machine learning algorithms, the new cluster may be defined by the newly added shape measurement, and this new cluster may then be taken into account for future predictions. That is, in cluster-based or similar implicit training ML setups, the training may amount to no or little more than storing the new measurement as a new cluster. A new descriptor D(s) such as a centroid may need to be initialized, which is trivial if the new measurement is the sole representative, but the descriptor D may need to be recomputed as more representatives are being added in the future.

If the modeling is explicit, the training algorithm may need to be re-run by newly adjusting the parameters of the model, such as the weights of a neural network, based on the new training data set, now including the new measurement. It may be useful to trigger this step only once a certain number of new measurements have been added as briefly mentioned earlier. Federated-learning, or reinforcement learning may be used. Before the model is newly deployed, one or more tests with test data applied to the retrained model may need to be run. In the meantime, user may continue to use the earlier trained model.

In an optional step S1940E, existing one or more sizes of one or more categories such as clusters may be re-balanced. This may involve changing a size of some one or more clusters to increase efficiency of the prediction algorithm.

At step S1940F the shape measurement that attracted the high uncertainty value may relate to a buckling event of the arm A, or to another fault with the shape sensing system. A new category for such a fault event may be opened and the training algorithm rerun in a new instance of the training phase to train the model to correctly recognize such faults in the feature. The shape measurement may be corrected to remove the buckling contribution in the shape measurement data, and the so corrected shape measurement data is then re-submitted for prediction at step S1940A.

It can thus be seen that the uncertainty value evaluation can be usefully harnessed for dynamic learning. By deciding to add new categories with new semantics and/or by updating the model by additional runs of the learning algorithm to account for the new categories, the model is being refined over time, with new categories being added to the model. Over time, the model thus becomes able to categorize a broader range of categories than before. Over time then, the number of categories are expected to dynamically grow and not only include the initial categories for the anatomical locations a priori of interest, but also categories for any one or more of: one or more in-between anatomical locations (transition region), fault events such as buckling and others still.

It should be noted that the updating of the training data set by adding new data at step S1940C may include instead adding new, synthetically generated training data specimens/instances, and the opening of new one or more categories may relate to such newly added training data. The generating of new data will be explained in more detail below at FIG. 20. The newly added training data may relate to new anatomical locations that only later turned out to be of interest or of which there were too few training data specimens, or none at all. Any other categories of medical or procedural interest may be added and the model so refined at step S1940D.

Reference is now made to FIG. 20, which shows a flow chart of a computer implemented method for synthetic generation of training data. This data allows enlarging an existing training data set of shape measurements to boost performance of the system C-SYS. Generating data synthetically rather than sourcing existing data from medical data repositories from same or other patients generated in previous procedures may be useful if there is a shortage of such existing historic measurement data in general or for specific anatomies or patient types.

In one such embodiment of data generation the method is image based. It may include at step S2010 displaying a current image or a previous image of an anatomy of interest for a given patient.

At step S2020 user input is received that defines a geometric path drawn on the image.

At step S2030 the said geometric path is then converted into shape measurement data, for instance by computing a series of local curvature values. Alternatively, stress or strain values may be computed, given a specification of material characteristics of the deformed arm to be used in future interventions. However, the conversion step S2030 is optional or may be an identity operation, as the shape measurements may be provided direct in spatial, preferably 3D coordinates (X,Y,Z), as specified by the user in step S2020.

In step S2020 the specification of the path may be provided by a discrete number of control points set into a section of the vessel tree as represented in the image, or into other portions of the image that represent the body portion/anatomy/anatomies of interest. A spline algorithm may be used to pass a curve through the control points to obtain the shape data. The underlying imagery may be obtained from an X-ray imaging apparatus. Imagery of an a bi-plane X-ray imaging apparatus may be used.

The tree structure indicative in the image may relate to other cavity systems not necessarily to the vessel system, such as to the biliary ducts or the network of bifurcations in a lung. The tree structure, such as the vessel tree, may be obtained by segmenting the image and displaying the segmented image at step S2010.

Reference is now made to the flow chart in FIG. 21 which shows steps of a computer implemented method of training a machine learning model as used in the above embodiments. The model is to be trained to be able to predict from shape measurements a category representative of an anatomical location in which the shape measurement was taken.

At step S2110 training data of a current training data set is received. The training data include shape measurements, either generated as per FIG. 20 or other, or sourced from earlier interventions where shape sensing data has been collected and stored.

At step S2120 a training algorithm is applied based on the training data. In embodiments, parameters of a model are adapted based on the training data such as in explicit modeling. In other embodiments, such as in implicit modeling, a data centric model is used, such as in clustering where the training data is stored and optionally descriptors are computed that represent characteristics of the training data clusters, such as centroids describing each cluster. The training data shape measurements s' may be applied in training for a given acquisition time, or in blocks (s', $s'_1, \ldots s'_n$), n≥1 of the current one, and one or more earlier measurements as described above. Training can be improved as the time context 1−n includes clues on the correct category.

At step S2130 the model so adapted is then made available for deployment.

In step S2140 it is checked whether new training data has been received and, if yes, the training phase can be restarted at step S2120 to account for the newly received training data.

The training algorithm at step S2120 may itself be iterative and the parameters of the model are adapted in one or more iteration steps for a given training data specimen/instance. Such is the case for example, in backpropagation type algorithms, or more generally for other gradient based algorithms. Such iterative training algorithm may be used for neural network type models as envisaged herein. Instead of training instance-by-instance, a set of training instances are processed at once and training proceeds set-by-set, such as in batchwise-learning, preferably envisaged herein.

However, any other training algorithm may be used based on the respective model such a support vector machines, decision trees, random forests etc. Any other type of training for categorization purposes (that is clustering or classification) is envisaged herein.

The training scheme may also be used for ML implementations of the transformation stage, such as for encoder-decoder type transformation stages, in particular of the variational autoencoder type or other autoencoder implementations and others still.

The components of system C-SYS may be implemented as one or more software modules, run on one or more general-purpose processing units PU such as a workstation associated with the imager IA, or on a server computer associated with a group of imagers.

Alternatively, some or all components of the system C-SYS may be arranged in hardware such as a suitably programmed microcontroller or microprocessor, such an FPGA (field-programmable-gate-array) or as a hardwired IC chip, an application specific integrated circuitry (ASIC), integrated into the imaging system IA. In a further embodiment still, any one of systems TS, SYS may be implemented in both, partly in software and partly in hardware.

The different components of any one or system C-SYS may be implemented on a single data processing unit PU. Alternatively, some or more components are implemented on different processing units PU, possibly remotely arranged in a distributed architecture and connectable in a suitable communication network such as in a cloud setting or client-server setup, etc.

One or more features described herein can be configured or implemented as or with circuitry encoded within a computer-readable medium, and/or combinations thereof. Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for controlling operation of at least one device in a medical procedure performable in relation to a patient, comprising:

an input interface for receiving optical shape measurement data of a deformable elongated optical shape sensing device positioned at least partly within the patient;

a predictor logic configured, based on previous optical shape measurement data, to determine from the optical shape measurement data of the deformable elongated optical shape sensing device a predictor result comprising an indication of at least one of an anatomical location inside the patient, a phase of the medical procedure being performed, and a type of the medical procedure being performed; and a control interface to issue a control signal for the at least one device, based on the at least one determined predictor result.

2. The system of claim 1, wherein the predictor logic based on previous optical shape measurement data is configured to categorize received optical shape measurement data into a category from a plurality of categories, wherein each category of the plurality of categories is associated with a categorization result.

3. The system of claim 2, wherein the predictor logic is further configured to determine an uncertainty measure associated with the predictor result, and when the uncertainty measure exceeds a threshold, to define a new category distinct from the plurality of categories and categorize the received shape measurement data into the new category.

4. The system of claim 2, further comprising a re-balancer configured, in response to determining that a size of at least one of the plurality of categories does not satisfy a size criterion, to rebalance the plurality of categories by modifying the categorization of the received optical shape measurement data among the plurality of categories.

5. The system of claim 1, wherein the predictor logic comprises a machine-learning model trained on the previous optical shape measurement data.

6. The system of claim 5, wherein the machine-learning model is trained on training data comprising at least one of:

i) historic shape measurements data of any deformable elongated optical shape sensing device collected in previous medical procedures, ii) user generated data, and iii) image-based computer-generated data.

7. The system of claim 5, wherein the optical shape measurement data and the predictor result are stored in a memory for retraining the machine-learning model, the predictor logic and the system being arranged to implement the retraining.

8. The system of claim 1, wherein the deformable elongated optical shape sensing device is configured to conform to surrounding anatomy.

9. The system of claim 1, wherein the input interface is further configured to receive contextual data associated with the optical shape measurement data, and the predictor logic is configured to determine the predictor result based on the previous optical shape measurement data and the contextual data, wherein the contextual data comprises any one or more of:

i) time data including shape measurement acquisition time or data derived from such time data, ii) chronological data of previous shape measurements, iii) meta-data including patient data, iv) data pertaining to, or generated by, any device used, or to be used, during the procedure, v) previous predictor results, and vi) 2D or 3D image data pertaining to the medical procedure.

10. The system of claim 9, wherein the contextual data is obtained by operation of an annotator configured to tag the optical shape measurement data or the previous optical shape measurement data, each tag indicative of the contextual data.

11. The system of claim 1, wherein the at least one device is, or includes, one or more of:

i) an imaging apparatus, and the control signal is to effect a change of an image acquisition setting;

ii) a display device, and the control signal is to effect displaying on the display device a graphics display including a graphical or textual indication of any one or more of a) the predicted result, b) the current input shape measurement, c) the one or more category of the previous shape measurement data; d) a virtual image of a reconstructed shape of the shape sensing device, together with a virtual and/or imaged representation of the anatomical location; e) a virtual and/or imaged representation of a next anatomical location likely to be passed by the shape sensing device in a navigation path of the shape sensing device; f) a representation of a planned path of navigation based on the result; g) an indication of a newly predicted anatomical location associated with a new associated organ is entered into by the shape sensing device;

iii) the, or an, interventional device usable in the procedure, and the control signal is to adapt an operation mode or parameter of the interventional device;

iv) the shape sensing system, and the control signal is to adapt an operation mode or a parameter of the shape sensing system;

v) a robot configured to drive the shape sensing device, and the control signal is to control the said robot;

vi) a workflow management system that integrates, uses or process the predicted result together with other data, and the control signal is to control operation of the workflow management system;

vii) a database or memory system, and the control signal to control whether or not the current input shape measurement data is to be stored, and viii) a registration module configured to register an interventional device and/or shape sensing device with imagery, and wherein the control signal is to control whether interventional device and/or shape sensing device is to be registered or re-registered with a given image.

12. The system of claim 1, wherein the predictor logic is capable of predicting the result without using acquired image data of the patient.

13. The system of claim 2, wherein the category is at least one of an anatomical location inside the patient, a phase of procedure, or a type of procedure.

14. The system of claim 8, wherein the predictor logic configured with anatomical-based characteristics to output the result including the indication is further configured to:

determine whether the received input shape measurement data of the deformable elongated optical shape sensing device is faulted by the optical shape sensing device conforming to the surround anatomy.

* * * * *